US007485415B2

(12) United States Patent
Buonagurio et al.

(10) Patent No.: US 7,485,415 B2
(45) Date of Patent: Feb. 3, 2009

(54) SEQUENCE ANALYSIS OF THE TETRAVALENT ROTAVIRUS VACCINE

(75) Inventors: Deborah A. Buonagurio, Rye, NY (US); Alice F. Georgiu, Montgomery, NY (US); Robert A. Lerch, New Hempstead, NY (US); Bruce B. Mason, Downington, PA (US); Shridhara C. Murthy, Ann Arbor, MI (US); Ruth S. Rappaport, Strafford, PA (US); Mohinder S. Sidhu, New City, NY (US); Stephen A. Udem, New York, NY (US); Timothy J. Zamb, Nyack, NJ (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 466 days.

(21) Appl. No.: 10/505,818

(22) PCT Filed: Feb. 19, 2003

(86) PCT No.: PCT/US03/05172

§ 371 (c)(1), (2), (4) Date: Jan. 18, 2005

(87) PCT Pub. No.: WO03/072716

PCT Pub. Date: Sep. 4, 2003

(65) Prior Publication Data

US 2005/0119471 A1 Jun. 2, 2005

Related U.S. Application Data

(60) Provisional application No. 60/359,960, filed on Feb. 27, 2002.

(51) Int. Cl.
*C12Q 1/70* (2006.01)
*C12N 15/46* (2006.01)
*C12N 15/63* (2006.01)
*C12N 1/21* (2006.01)
*C12N 5/10* (2006.01)
*A61K 39/15* (2006.01)

(52) U.S. Cl. .................. 435/5; 435/320.1; 435/69.3; 435/325; 435/252.3; 435/254.11; 424/215.1

(58) Field of Classification Search .................... None
See application file for complete search history.

(56) References Cited

U.S. PATENT DOCUMENTS 5,186,933 A 2/1993 Estes

OTHER PUBLICATIONS

Mitchell et al (Virology 177: 324-331, 1990).*
Cohen J., et al., "Nucleotide sequence of bovine rotavirus gene 1 and expression of the gene product in baculovirus," *Virology*, 171:131-140 (Jul. 1989).
Dharakul T., et al., "Immunization with baculovirus-expressed recombinant rotavirus proteins VP1, VP4, VP6, and VP7 induces CD8+T lymphocytes that mediate clearance of chronic rotavirus infection in SCID mice," *J. Virol.*, 1:5928-5932 (Nov. 1991).
Gentsch, et al., "Review of G and P typing results from a global collection of rotavirus strains: Implications for vaccine development," *J. Infect. Dis.*, 174:S30-S36 (Sep. 1996).
Ito H., et al., "Complete nucleotide sequence of a group A avian rotavirus genome and a comparison with its counterparts of mammalian rotaviruses," *Virus Res.*, 75:123-138 (2001).
Masendycz P. and Palombo E., "Genetic relatedness of VP1 genes of Australian and Taiwanese rotavirus isolates," *FEMS Microbiol. Lett.*, 198:147-150 (2001).
Midthun K., et al., "Rotavirus vaccines: An overview," *Clin. Micorbiol. Rev.*, 9:423-434 (Jul. 1996).
Nielsen P., et al., "Sequence-selective recognition of DNA by strand displacement with a thymine-substituted polyamide," *Science*, 254:1497-1500 (Dec. 6, 1991).

* cited by examiner

*Primary Examiner*—Mary E Mosher
(74) *Attorney, Agent, or Firm*—Townsend and Townsend and Crew LLP

(57) ABSTRACT

Isolated nucleic acid molecules comprising a gene segment from a rhesus rotavirus (RRV) or from one of three rhesus: human reassortant viruses are disclosed, including isolated nucleic acid molecules having a sequence selected from the group consisting of: SEQ ID NO: 1-14, inclusive, and isolated nucleic acid molecules encoding a protein having a sequence selected from the group consisting of SEQ ID NO: 15-28, inclusive, as well as variants of the isolated nucleic acid molecules.

12 Claims, No Drawings

```
                         SEQUENCE LISTING

<160> NUMBER OF SEQ ID NOS: 187

<210> SEQ ID NO 1
<211> LENGTH: 3302
<212> TYPE: DNA
<213> ORGANISM: Rotavirus

<400> SEQUENCE: 1
ggctattaaa gctatacaat ggggaagtat aatctaatct tgtcagaata tttatcattc      60
atatataact cacaatccgc agttcaaatt ccaatttact attcttccaa tagtgaatta     120
gagaatagat gtattgaatt tcattctaaa tgcttagaaa actcaaagaa tggactatca     180
ttgaaaaagc tctttgttga atatagcgat gttatagaga atgccacact gttgtcaata     240
ttatcgtact cttatgataa atataacgct gttgaaagga aattagtaaa atatgcaaaa     300
ggtaagccgc tagaagcaga tttgacagtg aatgagttgg attatgaaaa taacaagata     360
```

-continued

```
acatctgaac tattcccaac ggcagaggaa tatactgatt tattgatgga tccagcaatt      420
ttaacttcat tatcatcgaa tttaaatgca gttatgttct ggttggaaaa acatgaaaat      480
gacgttgctg aaaaactcaa aatttacaaa aggagattag acttatttac tatagtagct      540
tcaacagtaa ataaatatgg tgtaccaagg cacaatgcga aatatagata tgaatatgaa      600
gtaatgaaag ataagccgta ctacttggtg acatgggcaa attcttcaat tgaaatgctg      660
atgtcagttt tttctcatga agattattta attgcgagag aactgatagt actgtcatat      720
tctaatagat cgactctggc aaaactggtg tcatcaccaa tgtcaattct ggtagcttta      780
gtggatataa acgaacgtt cattacgaat gaagaactag agctagagtt ttcaaacaaa       840
tatgtacgag caatagttcc tgaccaaaca tttgatgaat taaaacaaat gcttgacaat      900
atgagaaaag ctgggttaac tgacatacct aagatgatac aggactggtt ggtcgattgc      960
tctattgaaa aatttccatt gatggctaaa atatattcgt ggtcatttca tgtcggattc      1020
aggaaacaga aaatgttgga cgccgcacta gatcaattga aaactgagta tacagaagat      1080
gtagatgacg aaatgtatcg agaatacaca atgctaataa gagatgaagt tgtgaaaatg      1140
cttgaggaac cagtaaagca tgatgaccat ttgttacagg attctgaatt agctggttta      1200
ctatcaatgt catcagcgtc gaatggtgaa tcaagacaac taaaatttgg tagaaagaca      1260
attttttcga ctaaaaagaa tatgcatgta atggatgaca tggctaatgg aagatacacg      1320
ccaggcataa taccaccagt gaatgtcgat aaaccgatac cattaggaag gagagatgta      1380
ccaggaagac ggactagaat aatatttatt ttaccatatg aatatttcat agcacaaacat     1440 gctgtagttg aaaaaatgct aatttatgcg aaacatacta gagaatatgc tgaattctac     1500
tcacagtcaa atcagttatt gtcttatggt gatgttacac gcttttatc taataactct      1560 atggtactat atacagacgt gtcccagtgg gactcatctc aacacaatac gcagccattt     1620
aggaaaggga taattatggg attggacatg ctagccaata tgactaatga tgctagagtt     1680
atacagacgc taaacttgta taaacagacg caaattaatc taatggattc atacgttcaa     1740
ataccagatg gtaatgttat taagaagata caatatgggg ctgtagcgtc aggagagaaa     1800
cagacgaaag cagcgaattc aatagcaaat ttagcactga ttaaaacggt tttatcacgc     1860
atttctaaca atatttcatt cgcgacgaag ataataagag ttgacggaga tgacaattac     1920
gcagtattgc aattcaatac agaagtaact aaacaaatgg ttcaagatgt gtcaaacgac     1980
gtgagagaaa catatgcgcg aatgaatact aaagttaaag ccttagtatc tacagtggga     2040
atagaaatag ctaaaaggta tattgcaggt gggaaaatat tctttagggc tggaataaat     2100
ttactgaata atgaaaaaaa aggacaaagc acacagtggg accaagcagc tgtcctatat     2160
tcgaactata ttgtgaatag acttcgagga tttgaaactg acagagagtt catttaact     2220 aaaataatgc aaatgacgtc agttgctatt accggatcgc taagactctt tccttctgaa     2280
cgcgtgttaa ccacgaactc tacatttaaa gtatttgact cggaggactt tattatagag     2340
tatgggacaa ctgacgatga agtatacata caaagagcgt tcatgtcttt atctagtcag     2400
aagtcaggaa tagctgatga gatagctgca tcatcgacgt ttaagaatta tgtgtctaga     2460
ttatctgagc agctgttgtt ttcaaagaat aatatagtgt ctagaggaat agcattgact     2520
gaaaaggcaa agttgaactc atacgcacca atatcacttg agaaaagacg tgcgcaaata     2580
tcagctttgc tgactatgct acaaaaaaccg gttactttta aatcaagtaa aataacaata     2640
aatgatatac ttagagatat aaagccattt ttcactgtaa acgaagcaca tttgccgata     2700
```

-continued

| | |
|---|---|
| caatatcaaa aatttatgcc aactttacca gacaatgtgc agtatataat tcagtgtata | 2760 |
| ggatccagaa cctaccaaat tgaagacgac ggttcaaagt cagcaatatc tcgactaata | 2820 |
| tcaaagtatt cagtttacaa accgtcaatc gaagagttat acaaagtaat ttcactacac | 2880 |
| gagaatgaaa tacaactata tttgatctca ctaggcatac cgaaaataga cgctgatacg | 2940 |
| tacgtcggat cgaaaattta ttctcaagat aaatacagga tattagagtc gtatgtatat | 3000 |
| aacttattat ctattaatta tggatgttat caactattcg actttaattc accagatcta | 3060 |
| gaaaagttga tcagaatacc gtttaaagga aagataccag ctgtcacttt tatattgcat | 3120 |
| ttatacgcta agctagaagt tataaatcat gccatcaaaa atggctcatg gataagctta | 3180 |
| ttctgcaact acccaaaatc agaaatgata aaattatgga agaaaatgtg gaacattaca | 3240 |
| tcactacgtt caccgtatac caatgcaaac ttctttcaag attagagcgc ttagatgtga | 3300 |
| cc | 3302 |

<210> SEQ ID NO 2
<211> LENGTH: 2708
<212> TYPE: DNA
<213> ORGANISM: Rotavirus

<400> SEQUENCE: 2

| | |
|---|---|
| ggctattaaa ggctcaatgg cgtacagaaa gcgtggagcg cgtcgtgaga cgaatttaaa | 60 |
| acaagatgat cgaatgcaag aaaaagaaga aaataaaaac gtaaatacta atagtgaaaa | 120 |
| taaaaatgct acaaaacctc aattatcaga gaaagtgcta tctcaaaagg aagaggtgat | 180 |
| tacagataat caagaagaaa ttaaaatagc tgatgaagtt aaaaaatcta ataaagagga | 240 |
| atcaaaacaa ctattagagg ttctaaaaac taaggaagaa catcaaaaag aagttcaata | 300 |
| cgaaatacta cagaaaacaa tacctacttt tgaaccaaaa gaatctatac taaagaaatt | 360 |
| agaagatatt aaaccagagc aagttaaaaa gcaaaccaaa ttattcagaa tatttgaacc | 420 |
| taggcaacta ccagtataca gagcaaacgg agagaaagaa ctacgcaaca gatggtattg | 480 |
| gaagttaaaa cgagacacct tgcccgatgg agattatgat gtgagagaat atttttttaaa | 540 |
| tttgtatgat caagtactaa ctgaaatgcc agattattta ctacttaaag acatggctgt | 600 |
| tgaaaacaag aattctagag atgcaggcaa agttgttgac tctgaaactg cagcccatttg | 660 |
| cgatgcgatt ttccaagatg aagaaaccga aggtgtagta agaagattca tagcagaaat | 720 |
| gaggcaaaga gtacaagctg atcgaaatgt agttaattac ccatcaatat tgcatccaat | 780 |
| tgatcatgcc tttaatgagt attttttaca gcatcagtta gttgaaccat tgaataatga | 840 |
| tataatattc aattacatac ctgaaagaat acggaatgac gtaaactata tactgaacat | 900 |
| ggatcgaaat ttaccttcaa cagctagata cattagacca aatttacttc aagatagact | 960 |
| caatttgcat gataacttcg aatccttatg ggatactata actacatcaa actacatctt | 1020 |
| agctagatca gttgtgccag accttaagga actagtgtcc accgaggctc aaatacaaaa | 1080 |
| aatgtcacag gatttgcaat tagaggcgct gacaattcaa tcagaaacac aatttttaac | 1140 |
| aggtatcaat tcacaggcag ctaatgactg ctttaagacg ttaattgccg ctatgcttag | 1200 |
| tcaacgtact atgtctttag atttcgtcac tacaaactac atgtcattaa tttcagggat | 1260 |
| gtggttatta acagttgtac ctaatgatat gttcatacgt gaatccctag tagcatgtca | 1320 |
| attggcaata attaatacca tcatatatcc agcctttgga atgcagagaa tgcattacag | 1380 |
| aaatggtgac ccccaaactc cttttcgat cgctgaacaa caaattcaga actttcaggt | 1440 |
| ggccaattgg ctacatttg ttaacaataa tcaatttaga caagtagtaa ttgatggagt | 1500 |

```
attaaaccaa gttctgaatg ataatataag aaatggacat gtagttaatc aattgatgga    1560
agctttaatg caattgtcac gacaacaatt cccaaccatg ccagtagatt ataaaagatc    1620
aatacagaga ggaatattac ttctatcgaa tagattagga caattggttg acctaactag    1680
gctattggca tataattatg aaactctgat ggcgtgcatt accatgaaca tgcaacatgt    1740
acaaactcta actactgaaa agttgcaatt aacatcagtt acttccttat gtatgttaat    1800
aggaaatgct acagttatac caagtccaca acattattt cattattata cgtcaacgt     1860 caattttcat tcaaattaca atgaaagaat aaatgacgca gtagcaatca taaccgccgc    1920
aaatagattg aatttgtatc agaaaaagat gaagtcgata gttgaagatt tcttaaagag    1980
actacaaata ttcgacattt ctagagttcc agatgatcaa atgtacagac tcagggatag    2040
attgagatta ctcccagttg aaattagaag attagatata tttaatttaa tattgatgaa    2100
tatggagcag attgaacgcg catcggataa aattgcccag ggagtgatta tagcttatag    2160
agacatgcag ttagagagag atgaaatgta tggctacgtt aacatagctc gtaatttaga    2220
cggttttcag cagataaatt tagaggagtt gatgagaacg ggagattatg cacaaattac    2280
taatatgcta ctaaataatc agccagtggc attagtagga gcactaccat ttataacaga    2340
ctcatcagtt atctcattgg tagctaaatt agacgctact gtctttgcac aaattgttaa    2400
gctcaggaag gttgatactt taaagccaat cctgtataaa ataaattctg attcaaatga    2460 ttttttatctt gtagcgaatt atgactgggt tccaacgtct acaacaaaag tttataaaca    2520
aataccacaa caatttgatt ttagagcatc tatgcatatg ttaacgtcta atttgacttt    2580
cactgtatat tccgaccttc ttgcattcgt ttcagcagac actgttgaac caattaatgc    2640
tgttgcattt gacaatatgc gcatcatgaa cgaactgtaa acgccaaccc cactgtggag    2700
atatgacc                                                              2708
```

<210> SEQ ID NO 3
<211> LENGTH: 2591
<212> TYPE: DNA
<213> ORGANISM: Rotavirus

<400> SEQUENCE: 3

```
ggctattaaa gcagtacgag tagtgtgttt tacctctaat ggtgtaaaca tgaaagtact      60
agctttaaga cacggtgtgg ctcaggtgta tgcagacacc caaatctata tcatgatga     120 tactaaagac agttacgaga atgcatttct tatatctaat cttacaacgc ataacatctt    180
atatttaaat tacagtatca aaacgcttga atattgaat aaatcaggaa ttgcagctgt     240
tgagattcaa tctcttgaag aattattcac tttaattaga tgtaattta cttatgatta    300 tgaaaacaat ataatttact tgcatgacta ctcatactac actaataatg aaataagaac    360
tgatcaacat tgggttacaa agactgatat tgaggaatac ttgttaccag atgtgaaatt    420
aacatacgta ggatataatg ggagtgatac tagaggacat tataacttct cattcacatg    480
ccagaatgct gcaaccgatg atgacttaat aatagaatac attttattccg aagcattgga    540 ctttcagaat ttcatgttaa agaaaattaa agaaagaatg actacttctt taccgatagc     600
acgtttatca aatagagttt ttagagataa attatttcca ttactaagtg aaaaacatca    660
gcgtatagtg aacattggac cgagaaatga atcaatgttt accttcttaa attttccatc    720
aattaagcaa ttttcaaatg gaccatattt agttaaagat actattaaat tgaagcaaga    780
aagatggttg gggaaaagag tgtctcagtt cgacattgga caatacaaga acatgatgaa    840
```

```
cgtcataaca actgtatatt attattataa cttatatcag aaaaaaccta ttatatatat    900
ggttggttca gctccttcat actggattta tgatgtcaaa caatattctg attttatgtt    960
tgagacttgg gacccacttg acactccata ttcatcagtg catcataaag aattattttt   1020
tgagaaggac ataactagat taaaggatga ttcaatattg tatattgata tcaggactga   1080
tcgtggaaac acggattgga agaatggag gaaaatagtt gaggcgcaaa ctattagtaa   1140
ccttaaactt gcataccgat acttatctgg tggtaagtcg aaggtatgtt gtgttaaaat   1200
gactgctatg gatttagagc ttcccatatc tgcaaagtta ttgcatcatc caactactga   1260
aatccgatca gagttttatc ttcttctgga catctgggac attagtaatg tcaaaagatt   1320
tattccaaag ggagtattat attcattcat aaataacgtt actactgaaa atgtattcat   1380
acaaccgccg ttcaaaatca aaccgtttaa gaatgattat attgtggcat tatacgcatt   1440
atcaaatgat tttaatgata gaacggatgt aattaactta attaacaatc agaaacaatc   1500
gctcattact gtaagaatta ataacacatt taaagatgaa ccaaaggtag ggtttaagaa   1560
tatatatgat tggacctttc taccaacaga ttttactaca actgatgcca taataaccte   1620
atacgatgga tgtttaggta tatttggatt atcaatatcc ttagcttcaa agcctacggg   1680
aaataatcac ttgtttatct taaatggaac cgataagtat tataaattgg atcaattcgc   1740
aaaccatact ggcatttcca gaagatcaca ccaaattaga ttttcagaat ccgcaacatc   1800
gtattcagga tacatattca gagatttatc taacaacaat tttaacttga ttgggacaaa   1860
tgtagaaaat tcagtttcag gacatgtata taatgcgtta atttattata gatataacta   1920
ctctttttgac ttaaaaagat ggatatactt acactcgata gaaaaagctg atatagaagg   1980
tggaaagtat tatgaacatg ctccgataga attgatttat gcctgtagat cagcaaaaga   2040
attcgcttta ttacaagatg atcttactgt attacgttat gctaatgaaa tcgagagcta   2100
tataaataaa gtatatagta taacatatgc agatgatcca aattacttta taggtattaa   2160
attcagacac attccctatg aatatgatgt taaaattcca catttgacat ttggagtatt   2220
atttatttca gataatatga ttccagatgt agtggagatc atgaaaatta tgaaaaagga   2280
attatttgaa atggatataa ccactagtta cacatatatg ttatctgatg aatatatgt    2340
agcaaacgtt agtggagttc tagcgacata ttttaaaatg tataatttat tttataagag   2400
tcagattaca ttcggtcaat ctagaatgtt tattccacat ataacactaa gttttagtaa   2460
taataaaaca gtaagaatag aaagtactag gttaaagatt agctcaatat atttaagaaa   2520
gattaaagga gatacggtgt ttgatatgtc tgagtgagct agaaacttaa cacactagtc   2580
atgatgtgac c                                                        2591
```

<210> SEQ ID NO 4
<211> LENGTH: 2362
<212> TYPE: DNA
<213> ORGANISM: Rotavirus

<400> SEQUENCE: 4

```
ggctataaaa tggcttcgct catttataga caattgctta caaattcata taccgttgac    60
ttatctgatg aaatacaaga aattggatct acaaaaacgc aaaatgtcac tattaatcta   120
ggtcctttg ctcaaacagg ttatgctcca gttaactggg gtcctggtga aactaatgat    180
tctactactg tagaaccggt acttgatggt ccttatcaac caacaacgtt caatccacca   240
gtagattatt ggatgctatt agcacctaca gcagctggag tagtagtaga aggtactaat   300
aatacagacc gatggctagc tacaatttta gttgagccaa acgtaacatc agaaaccaga   360
```

| | |
|---|---|
| agttatacgc tatttggaac gcaagagcaa attacaatag ctaatgcttc ccaaacacaa | 420 |
| tggaaattta ttgatgtcgt taaaactaca caaaatggaa gctattcaca atacggacca | 480 |
| ttacaatcta ctccaaaact ctatgccgtg atgaaacata atggtaaaat ttatacatat | 540 |
| aatggagaaa ctccgaatgt gaccactaag tactactcaa ctacaaatta tgattcagta | 600 |
| aacatgacag cattttgtga cttttatatt ataccctagag aagaagaatc aacatgtacc | 660 |
| gagtacatta ataacgggtt acctccgatt cagaatacac gaaacattgt tccattggcg | 720 |
| ctttcagcta gaaatataat atcacataga gctcaagcga atgaagatat cgttgtgtca | 780 |
| aagacatcac tttggaaaga gatgcaatac aatagagaca tcacaattcg atttaaattc | 840 |
| gcaagttcaa ttgttaaatc cggtgggcta ggttataaat ggtcagagat ttcatttaaa | 900 |
| ccagcaaact atcaatatac gtatacacga gatggagagg aggtgacagc tcacacgacg | 960 |
| tgctccgtaa acggaatgaa cgatttaat ttcaatgggg gatcgttacc aacggatttt | 1020 |
| gtaatatcaa gatatgaagt aattaaagag aattcttatg tttatgttga ttactgggat | 1080 |
| gattcacaag ccttcaggaa catggtttat gtaaggtcat tagctgctaa tttaaactct | 1140 |
| gttatatgta ctgggggtga ttatagcttt gcattaccgg ttggtcaatg gccagtaatg | 1200 |
| actggcggag cagtgtcatt gcattcagct ggtgttacgc tatccacaca gttcacagat | 1260 |
| tttgtatcat taaattcttt aaggttcagg tttagactaa ctgttgaaga gccatcattc | 1320 |
| tcgatcacca gaactagagt tagtagattg tatgggttac ctgcagctaa cccaaataat | 1380 |
| ggaaaagaat attatgaagt ggctggcaga ttctcactaa tatcattggt accatctaat | 1440 |
| gacgattacc agacaccaat aactaattca gttacagtca gacaagattt agaacgacag | 1500 |
| ttgggtgaac ttagagaaga attcaacgct ctctcacaag agatagccat gtcgcagcta | 1560 |
| attgatttgg cattacttcc attggatatg ttttcgatgt ttttccggtat taagagcacc | 1620 |
| atagatgcag ctaaatcaat ggctactagt gtaatgaaga aatttaagaa atcaggttta | 1680 |
| gctaactctg tatctacatt aacagactca ctgtccgacg cagcttcttc aatttcaaga | 1740 |
| ggagcatcta ttcgttcagt tggatcatca gcatcagcat ggacggatgt ctcaacacaa | 1800 |
| atcactgatg tttcttcatc tgtcagttcg atctcgacac agacttcaac tattagtaga | 1860 |
| cggctacgac taaagaaat ggctacgcaa acagaaggga tgaatttcga tgatatatct | 1920 |
| gctgcagtat tgaagactaa aattgatcga tccactcaaa tatctccaaa cacattacca | 1980 |
| gatatagtca ctgaagcttc agagaagttc attcctaata gagcgtacag agtaataaat | 2040 |
| aatgatgaag tctttgaagc gggaacagat ggaagatttt ttgcgtatcg tgttgaaacg | 2100 |
| ttcgatgaaa tacctttga tgtgcaaaag tttgcagatc tagtaactga ctctccggtc | 2160 |
| atctcagcca taatagactt taagacacta aagaatctaa acgacaatta tggtattagt | 2220 |
| aggcaacaag catttaatct gctaagatcc gatccaagag tattacgtga atttatcaat | 2280 |
| caagacaatc caataattcg taacagaatt gaacagttaa taatgcagtg tagactgtaa | 2340 |
| gcaatttcta gaggatgtga cc | 2362 |

<210> SEQ ID NO 5
<211> LENGTH: 1599
<212> TYPE: DNA
<213> ORGANISM: Rotavirus
<400> SEQUENCE: 5

| | |
|---|---|
| ggcttttttt tgaaaagtct tgtgttagcc atggcaacct ttaaggatgc ttgctttcat | 60 |

-continued

```
tatagaaggg ttacaaaact aaacagagaa ttgctgagaa ttggagcaaa ttcagtatgg      120
actccagtct cttcgaataa aattaaaatt aaagggtggt gcattgagtg ttgtcaatta      180
actggattga cttttttgtca cggatgttcg ctagctcatg tttgtcagtg gtgcatccaa    240
aacaaacgtt gcttcttgga caatgaacca catcttttaa aattaagaac ttttgaatct     300
ccaataacga aggaaaaatt acaatgcatt attaatttat atgaattact atttccaatt     360
aatcatgggg ttatcaataa atttaaaaaa acaataaaac agaggaaatg tagaaatgag     420
tttgacaaat catggtataa tcagctactg cttccaatta ctttaaatgc tgcagttttc     480
aagtttcact caagggatgt ttatgttttt ggatttatg aaggatcatc accatgcata     540
gatttgccat atagacttgt aaattgcatt gatttatatg ataaactatt gttagatcaa     600
gtaaactttg aaaggatgag ttctcttcca gataatttac aatccatcta tgcaaacaaa     660
tacttcaaat taagtagact tccttcaatg aagctaaaac gaatctatta ctcagatttc     720
tccaaacaga atttgattaa taagtacaag actaaaagtc gcatagttct taggaatctt    780
actgaattca cctgggattc tcaaactgat ttacatcatg atctgattaa tgataaagat    840
aaaatacttg ccgcattatc aacatcatca ttaaaacaat ttgaaacaca tgatttaaat    900
ttggggagaa taaaagctga cattttgaa cttggacatc actgcaaacc aaattacatc    960
tcatcaaatc attggcaacc agcatcaaaa atttctaaat gtaaatggtg taatgtaaaa   1020
tatgcattca gagacatgga ttggaagatg gaatcaatgt acaatgaact tttaagcttt    1080
atccaatctt gctataaaag taatgttaat gtaggacatt gtagttcaat tgaaaaagct    1140
tatccattag ttaaagatat actttggcat tcaattactg aatatattga tcaaactgtt    1200
gagaaattgt ttaatacaat gaatccagtg caagtaaatg aacagcaggt aataaagttc    1260
tgttggcaaa tagatatcgc attatatatg cacattaaaa tgatactgga aaccgaggct    1320
cttccattta ctttcacatt gaatcagttc aattctataa ttaaagggat tgtgaaccaa   1380
tggtgtgatg ttgctgaatt agatcacttg ccgttatgca ctgaacagac tgatgcattg   1440
gttaaattgg aagaagaagg aaaactatct gaagaatatg agcttctgat ctcggactct    1500
gaagatgacg actaatgatt gaattaacta tcaccacagt ttttgccatc acaagacctt    1560
ctggactaga gtagcgccta gccagcaaaa actgtgacc                          1599
```

<210> SEQ ID NO 6
<211> LENGTH: 1356
<212> TYPE: DNA
<213> ORGANISM: Rotavirus

<400> SEQUENCE: 6

```
ggcttttaaa cgaagtcttc aacatggatg tcctgtactc cttgtcaaaa actcttaaag      60
atgctagaga caaaattgtc gaaggcacat tatactccaa tgtaagtgat ctaattcaac     120
aatttaatca aatgataatt actatgaatg gaaatgaatt tcaaactgga ggaattggta     180
atctgccgat tagaaattgg aattttgatt ttggattact tggaacaact ctactaaatt     240
tagatgctaa ctatgtcgaa acggcccgta atacaattga ttattttgta gatttttgtag    300 ataatgtatg catggacgaa atggttagag aatcacaaag aaatggaatt gcaccacaat    360
cagactcact tagaaagttg tcaggcatta aatttaaaag aataaatttt gacaattcat    420
cagaatacat tgagaactgg aatttgcaaa acagaagaca agaacgggt tttacatttc     480 ataaaccaaa cattttccct tattcagctt cattcacact gaacagatca caaccggctc    540
atgataactt gatgggtacg atgtggctca atgcgggatc agaaattcag gtcgctggat    600
```

```
tcgactattc atgtgcaata aatgcgccag ctaatataca acaatttgag catattgtac     660
agcttcgaag ggtgttgact acagctacaa taactcttct accagatgca gaaagattta     720
gttttccaag agtgattaat tcagctgacg gagcggctac atggtacttt aatccagtga     780
ttcttagacc aaataacgtt gaagtagaat ttctactaaa cgggcagata ataaatactt     840
accaagcaag atttggaacg ataatagcca gaaattttga tacaattaga ttgtcatttc     900
agttaatgag accaccaaat atgacaccag cggtagcggc gttatttcca aatgcgcaac     960
catttgaaca tcatgcaaca gtaggactca cgcttagaat cgaatctgca gtttgtgaat    1020
cagtacttgc cgacgcaagc aaaacaatgc tagcgaacgt gacatctgtt agacaagaat    1080
acgcgatacc agttggacca gttttttccac caggtatgaa ttggactgat ttgatcacta    1140
actattcacc atctagagag gataacttgc agcgtgtatt tacagtggct tccattagaa    1200
gcatgcttgt caaatgagga ccaagctaac cacttggtat ccgactttga tgagtatgta    1260
gcttcgtcaa gctgtttgaa ctctgtaagt aaggatgcgt ccacgtattc gctacacaga    1320
gtaatcactc agatgacgta gtgagaggat gtgacc                              1356

<210> SEQ ID NO 7
<211> LENGTH: 1078
<212> TYPE: DNA
<213> ORGANISM: Rotavirus

<400> SEQUENCE: 7
ggcatttaat gcttttcagt ggttgatgct caagatggag tctactcagc agatggcttc      60
ttctattatt aattcttcat ttgaagctgc agtggttgct gcaacttcta ctcttgaatt     120
gatgggtatt caatatgact acaatgaggt atatactaga gtaaagagta aatttgattt     180
agttatggat gattctggtg taaaaaataa cttaataggt aaagcaatta ctattgatca     240
agctttgaat ggaaaattta gttcagcgat taggaataga aattggatga ctgactctcg     300
aactgtagct aaattagatg aggatgtaaa taaactaaga attatgctat catcaaaagg     360
aatcgatcag aaaatgagag tgcttaatgc ttgttttagt gtcaagagaa tacctgggaa     420
atcatcatct atagttaaat gtactagact gatgaaagac aaattagaac gtggtgaagt     480
tgaagttgat gattcctttg ttgaagagaa aatggaagta gatacaattg attggaaatc     540
aagatatgaa cagttagaaa agagatttga gtcactgaaa catcgggtta atgagaagta     600
taatcattgg gttcttaaag ctagaaaggt aaatgaaaat atgaattctc ttcaaaatgt     660
gatttctcaa caacaagcac acattaatga actacaaatg tataataata aattagaacg     720
tgatttgcaa tccaaaattg gatctgttgt gtcatcaata gaatggtatc taagatcgat     780
ggaattatct gatgatgtaa aatcagacat tgaacaacag ctgaattcaa tagatcaatt     840
aaatccagtt aatgcaatag atgattttga atcaatactt cgcaatttaa tttctgatta     900
tgataggcta tttataatgt ttaaaggatt attgcagcaa tgcaactaca cttatactta     960
tgagtaattg aatgaacaat tcaatactat taccatctac acgtaaccct ctatgagcac    1020
aatagttaaa agctaacact gtcaaaaacc taaatggcta tagggcgtt atgtgacc       1078

<210> SEQ ID NO 8
<211> LENGTH: 1059
<212> TYPE: DNA
<213> ORGANISM: Rotavirus

<400> SEQUENCE: 8
```

-continued

```
ggcttttaaa gcgtctcagt cgccgtttga gccttgcggt gtagccatgg ctgagctagc      60
ttgcttttgt tatccccatt tggagaacga tagctataga ttcattccat tcaatagttt     120
ggctataaaa tgtatgttga cagcaaaagt agataaaaaa gatcaggata aattttacaa     180
ttcaataatt tatggtatcg caccaccgcc acaattcaaa aaacgttata acacaaatga     240
caattcaaga ggaatgaatt atgaaactcc aatgtttaat aaagtggcgg tgttaatttg     300
tgaagcgttg aattcaatta agttactca atctgatgtt gcgaatgtac tttcaaaagt     360
agtttctgta agacatctag agaatttggt actgagaaga gagaatcatc aggacgtgct     420
ttttcattca aaagagttgt tgctgaaatc agtactaata gctattggtc actcaaaaga     480
aattgaaaca actgccaccg ctgaaggagg ggaaatagtt tttcaaaatg cagcttttac     540
aatgtggaaa ttgacatacc tggaacatag actaatgcca atttttggatc aaaatttat     600 tgaatataaa ataacagtga atgaagataa accgatttca gaatcacatg ttaaagaact     660
cattgctgag ttgcggtggc aatacaacaa atttgcagta attacacatg gtaaaggtca     720
ctacagagtt gtaaaatatt catcagttgc gaatcatgca gatagagttt acgctacttt     780
caagagcaat aataagaatg gtaatgtgct agagtttaat ctacttgatc aaagagtaat     840
atggcagaac tggtatgcgt ttacatcctc aatgaaacaa ggtaacactc ttgaaatatg     900
caagaaacta ctgttccaaa aaatgaagcg ggaaagtaat ccgtttaagg gactgtcaac     960
tgatagaaag atggatgagg tttctcaaat aggaattaa ttcgttatca atttgagagt    1020
gggtatgaca aagtaagaat agaaagcgct tatgtgacc                          1059
```

<210> SEQ ID NO 9
<211> LENGTH: 1062
<212> TYPE: DNA
<213> ORGANISM: Rotavirus

<400> SEQUENCE: 9

```
ggctttaaaa gcgagaattt ccgtttggct agcggttagc tccttttaat gtatggtatt      60
gaatatacca cagttctaac ctttctgata tcgctcattt tattgaatta tattttaaaa     120
tctttgacta gaatgatgga ctttattatt tacagatttc ttttattgt agttattttg     180 tcaccattac taaaagccca aaattatgga attaatctac caattactgg ttcaatggac     240
actgcatacg ctaactctac acaggaagag acttttctca catctacttt gtgtctatat     300
tatccaactg aagctgcaac agaaataaat gataattcgt ggaaggatac actctcacaa     360
ttattcttga ctaaaggatg gccaactgga tcagtttatt ttaaagaata cacgatatt      420 gcttcctttt cagttgatcc acaactatat tgtgattata acgtggtact aatgaaatat     480
gatgcgactt tgcagctgga catgtctgaa ctagctgatt taatactgaa tgaatggctg     540
tgcaatccaa tggatattac tctatattat tatcaacaaa cagacgaagc taacaaatgg     600
atttctatgg gatcttcctg tacaataaaa gtatgtccac ttaatacaca gactcttgga     660
attgggtgtt tgactactga tacggcaaca tttgaagaag tcgctacagc tgaaaaactg     720
gtgattactg acgttgtcga tggtgtgaat cataaacttg atgttacaac tgctacttgc     780
actatcagaa actgcaaaaa attaggacca agggaaaatg tagcagtaat tcaagttgga     840
ggttctgatg ttctcgacat aacgctgat ccaaccacag caccacaaac tgaacgaatg     900
atgcgcatta ttggaagaa atggtggcaa gttttttata ccgtagtcga ctatgtgaat     960
caaataattc aagcaatgtc caaaagatca cgatcactta actctgctgc attctattat    1020
agaatatagg tatagctttg gttagaattg tatgatgtga cc                       1062
```

-continued

<210> SEQ ID NO 10
<211> LENGTH: 750
<212> TYPE: DNA
<213> ORGANISM: Rotavirus

<400> SEQUENCE: 10
ggcttttaaa agttctgttc cgagagagcg cgtgcggaaa gatggaaaag cttaccgacc 60
tcaactacac attgagtgta gtcactctca tgaatgatac tttacatacc ataatggagg 120
atcctggaat ggcgtatttt ccatacattg cttctgtcct aactgtacta tttacattac 180
ataaggcctc ggttccaacc atgaagattg ctcttaaaac gtcaaagtgt tcatataaag 240
taatcaaata ctgcattgtg tcaattttta acactctatt gaaactggct ggatataaag 300
aacaaattac tactaaagat gaaattgaaa ggcaaatgga cagagttgta aaagaaatga 360
gacgtcagct ggaaatgatt gataagctaa ccactagaga gattgagcaa gtcgaactac 420
ttaaacgaat tcatgatatg ttgataatta aaccagttga caaaattgat atgtcacaag 480
aatttaatca gaaatatttc aaaacgctaa atgattgggc tgaaggtgaa aatccatatg 540
aaccaaaaga ggtgactgca tcattgtgag aggttgagct gccgtcgtct gtctgcggaa 600
gcggcggagt tcttaacagt aagccccatc ggacctgatg actggttgag aagccacaac 660
cagtcatatc gcgtgtgact cagtcttaat cccgtttaac caatccagcc agcgctggac 720
gttaatggaa ggaacggtct taatgtgacc 750

<210> SEQ ID NO 11
<211> LENGTH: 667
<212> TYPE: DNA
<213> ORGANISM: Rotavirus

<400> SEQUENCE: 11
ggcttttaaa gcgctacagt gatgtctctc agtattgacg tgacaagtct tccatctatt 60
tcctccagca tttataaaca tgaatcatct tcaacgacgt caactctttc tggaaaatct 120
attggtagga gtgaacagta cgtttcacca gatgcagaag cattcaataa gtacatgttg 180
tcgaagtctc cagaggatat tggaccatct gattctgctt caaacgaccc actcaccagt 240
ttttcgatta gatcgaatgc agttaagaca aatgcagacg ctggcgtgtc tatggattca 300
tcgacacaat cacgaccttc aagtaacgtt ggatgcgatc aagtggattt ctccttaagt 360
aaaggcatta aagtaaacgc taatttagat tcatctattt cagtatcaac agtttccaag 420
aaggagaaat ccaaatcaga tcataaaaat aggaaacact acccgagaat tgaagcagat 480
tccgattcag acgaatatgt acttgatgat tcagatagtg atgatggtaa gtgtaaaaac 540
tgtaaatata agaaaaagta tttcgcactt agaatgagaa tgaagcaagt cgcaatgcag 600
ttgattgaag atttgtaagt ctaacctgag gactcactag gaagctcccc acttccgttt 660
tgtgacc 667

<210> SEQ ID NO 12
<211> LENGTH: 1062
<212> TYPE: DNA
<213> ORGANISM: Rotavirus

<400> SEQUENCE: 12
ggctttaaaa gagagaattt ccgtctggct aacggttagc tccttttaat gtatggtatt 60
gaatatacca caattctaat ctttttgata tcaatcattc tactcaacta tatattaaaa 120

| | |
|---|---|
| tcagtgactc gaataatgga ctacattata tatagatttt tgttgattac tgtagcatta | 180 |
| tttgctttga caagagctca gaattatgga cttaacttac caataacagg atcaatggac | 240 |
| gctgtatata ctaactctac tcaagaagaa gtgtttctaa cttctacgtt atgtctgtat | 300 |
| tatccaactg aagcaagtac tcaaatcaat gatggtgact ggaaagactc attgtcgcaa | 360 |
| atgtttctta caagggttg gccaacagga tctgtttact ttaaagagta ctcaagtatt | 420 |
| gttgattttt ctgttgaccc acagctgtat tgtgactata atttagtact tatgaaatat | 480 |
| gaccaaagtc ttgaattaga tatgtcggag ttagctgatt taatattgaa tgaatggtta | 540 |
| tgtaacccaa tggatgtaac attatactat tatcaacaat cgggagaatc aaataagtgg | 600 |
| atatcgatgg gatcatcatg taccgtgaaa gtgtgtccgc taaatacaca acgttaggg | 660 |
| ataggttgtc aaacaacaaa cgtagactca tttgaaatga ttgctgagaa tgagaaatta | 720 |
| gctatagtgg atgtcgttga tgggataaat cataaaataa atttaacaac tacgacatgt | 780 |
| actattcgaa attgtaagaa attaggtcca agagaaaatg tagctgtaat acaagttggt | 840 |
| ggttctaatg tattagacat aacagcagat ccaacaacta atccacaaac tgagagaatg | 900 |
| atgagagtga attggaaaaa gtggtggcaa gtatttttata ctatagtaga ttatattaat | 960 |
| caaattgtac aggtaatgtc caagagatca agatcattaa attctgcagc ttttttattat | 1020 |
| agagtataga tatatcttag attagaattg ttcgatgtga cc | 1062 |

<210> SEQ ID NO 13
<211> LENGTH: 1062
<212> TYPE: DNA
<213> ORGANISM: Rotavirus

<400> SEQUENCE: 13

| | |
|---|---|
| ggctttaaaa acgagaattt ccgtctggct agcggttagc tcttttttaat gtatggtatt | 60 |
| gaatatacca caattctgac cattttaata tctatcatat tattgaatta tatattaaaa | 120 |
| actataacta atacgatgga ctacataatt ttcaggtttt tactactcat tgctttaata | 180 |
| tcaccatttg taaggacaca aaattatggt atgtatttac caataacggg gtcactagac | 240 |
| gctgtatata cgaattcgac tagtggagag ccatttttaa cttcgacgct atgtttatac | 300 |
| tatccagcag aagctaaaaa tgagatttca gatgatgaat gggaaaatac tctatcacaa | 360 |
| ttatttttaa ctaaaggatg gccaattgga tcagtttatt ttaaagacta caatgatatt | 420 |
| aacacatttt ctgtgaatcc acaactgtat tgtgattata atgtagtatt gatgagatat | 480 |
| gacaatacat ctgaattaga tgcatcagag ttagcagatc ttatattgaa tgaatggctg | 540 |
| tgcaatccta tggacatatc acttactat tatcaacaaa gtagcgaatc aaataaatgg | 600 |
| atatcgatgg gaacagactg cacgtaaaa gttgtccac tcaatacaca aaccttaggg | 660 |
| attggatgca aaactacgga cgtaaacaca tttgagattg ttgcgtcgtc tgaaaaatta | 720 |
| gtaattactg acgttgtaaa tggtgttaat cataagataa atatttccaat aaatacgtgc | 780 |
| actatacgta actgtaataa attaggacca cgagaaaatg ttgctataat tcaagttggt | 840 |
| ggaccgaacg cattagatat cactgctgat ccaacaacag tcccacaagt tcaaagaatc | 900 |
| atgcgaataa attggaaaaa atggtggcaa gtatttttata cagtagttga ctatattaac | 960 |
| caagttatac aagtcatgtc caacgatca agatcattag acgcagctgc tttttattat | 1020 |
| agaatttaga tatagatttg gtcagatttg tatgatgtga cc | 1062 |

<210> SEQ ID NO 14
<211> LENGTH: 1062

-continued

```
<212> TYPE: DNA
<213> ORGANISM: Rotavirus

<400> SEQUENCE: 14
ggctttaaaa gagagaattt ccgtttggct agcggatagc tccttttaat gtatggtatt      60
gaatatacca cagttctatt ttatttgata tcgttcgttc ttgtgagtta tattctgaaa     120
accataataa agataatgga ctatattatt tatagaataa catttgtaat tgtagtatta     180
tcagtattat cgaatgcaca aaattatgga ataaatttgc caattactgg atctatggat     240
acagcatatg ctaactcaac acaagacaat aatttttat tttcaacttt atgtctatat      300
tatccatcag aagctccaac tcaaattagt gacactgaat ggaaagatac actatctcag     360 ctgttttta ccaaaggatg gccgacaggt tcagtttatt ttaatgaata ttcaaacgtt      420
ttagaatttt ccatcgaccc aaagctatac tgtgattata atgttgtgct aattagattc     480
gtttctggtg aggagttgga catatctgaa ttagctgatc taatactgaa tgagtggtta     540
tgtaatccaa tggatataac attatattat taccaacaaa ctggagaggc aaacaaatgg     600
atatcaatgg gatcatcatg taccgttaaa gtgtgtccat aaatactca gacattagga      660 attggatgtc aaacgacaaa tacagctact tttgaaacag ttgctgatag cgaaaaattg     720
gcaataattg atgttgtcga cagcgtaaat cataaattaa atatcacatc tactacatgt     780
acaatacgga attgtaataa actaggaccg agagaaaatg tggctataat acaggttggc     840
ggttctaata tattagatat aacagctgat cccacaactt ctccacaaac agaacgaatg     900
atgcgcgtaa actggaaaaa atggtggcaa gtattctaca ctgtagttga ttacattgat     960
cagatagtac aagtaatgtc caaaagatca agatcgttag atttgtcatc tttctattat    1020
agagtgtaga tatatcctaa aatagaactg tttgatgtga cc                        1062

<210> SEQ ID NO 15
<211> LENGTH: 1078
<212> TYPE: PRT
<213> ORGANISM: Rotavirus

<400> SEQUENCE: 15

Met Gly Lys Tyr Asn Leu Ile Leu Ser Glu Tyr Leu Ser Phe Ile Tyr
 1               5                   10                  15

Asn Ser Gln Ser Ala Val Gln Ile Pro Ile Tyr Ser Ser Asn Ser
                 20                  25                  30

Glu Leu Glu Asn Arg Cys Ile Glu Phe His Ser Lys Cys Leu Glu Asn
             35                  40                  45

Ser Lys Asn Gly Leu Ser Leu Lys Lys Leu Phe Val Glu Tyr Ser Asp
         50                  55                  60

Val Ile Glu Asn Ala Thr Leu Leu Ser Ile Leu Ser Tyr Ser Tyr Asp
65                  70                  75                  80

Lys Tyr Asn Ala Val Glu Arg Lys Leu Val Lys Tyr Ala Lys Gly Lys
                 85                  90                  95

Pro Leu Glu Ala Asp Leu Thr Val Asn Glu Leu Asp Tyr Glu Asn Asn
            100                 105                 110

Lys Ile Thr Ser Glu Leu Phe Pro Thr Ala Glu Glu Tyr Thr Asp Leu
        115                 120                 125

Leu Met Asp Pro Ala Ile Leu Thr Ser Leu Ser Ser Asn Leu Asn Ala
    130                 135                 140

Val Met Phe Trp Leu Glu Lys His Glu Asn Asp Val Ala Glu Lys Leu
145                 150                 155                 160
```

-continued

```
Lys Ile Tyr Lys Arg Arg Leu Asp Leu Phe Thr Ile Val Ala Ser Thr
                165                 170                 175

Val Asn Lys Tyr Gly Val Pro Arg His Asn Ala Lys Tyr Arg Tyr Glu
            180                 185                 190

Tyr Glu Val Met Lys Asp Lys Pro Tyr Tyr Leu Val Thr Trp Ala Asn
        195                 200                 205

Ser Ser Ile Glu Met Leu Met Ser Val Phe Ser His Glu Asp Tyr Leu
    210                 215                 220

Ile Ala Arg Glu Leu Ile Val Leu Ser Tyr Ser Asn Arg Ser Thr Leu
225                 230                 235                 240

Ala Lys Leu Val Ser Ser Pro Met Ser Ile Leu Val Val Asp Ile Asn
                245                 250                 255

Gly Thr Phe Ile Thr Asn Glu Glu Leu Glu Leu Glu Phe Ser Asn Lys
            260                 265                 270

Tyr Val Arg Ala Ile Val Pro Asp Gln Thr Phe Asp Glu Leu Lys Gln
        275                 280                 285

Met Leu Asp Asn Met Arg Lys Ala Gly Leu Thr Asp Ile Pro Lys Met
    290                 295                 300

Ile Gln Asp Trp Leu Val Asp Cys Ser Ile Glu Lys Phe Pro Leu Met
305                 310                 315                 320

Ala Lys Ile Tyr Ser Trp Ser Phe His Val Gly Phe Arg Lys Gln Lys
                325                 330                 335

Met Leu Asp Ala Ala Leu Asp Gln Leu Lys Thr Glu Tyr Thr Glu Asp
            340                 345                 350

Val Asp Asp Glu Met Tyr Arg Glu Tyr Thr Met Leu Ile Arg Asp Glu
        355                 360                 365

Val Val Lys Met Leu Glu Glu Pro Val Lys His Asp Asp His Leu Leu
    370                 375                 380

Gln Asp Ser Glu Leu Ala Gly Leu Leu Ser Met Ser Ser Asn Gly Glu
385                 390                 395                 400

Ser Arg Gln Leu Lys Phe Gly Arg Lys Thr Ile Phe Ser Thr Lys Lys
                405                 410                 415

Asn Met His Val Met Asp Asp Met Ala Asn Gly Arg Tyr Thr Pro Gly
            420                 425                 430

Ile Ile Pro Pro Val Asn Val Asp Lys Pro Ile Pro Leu Gly Arg Arg
        435                 440                 445

Asp Val Pro Gly Arg Arg Thr Arg Ile Ile Phe Ile Leu Pro Tyr Glu
    450                 455                 460

Tyr Phe Ile Ala Gln His Ala Val Val Glu Lys Met Leu Ile Tyr Ala
465                 470                 475                 480

Lys His Thr Arg Glu Tyr Ala Glu Phe Tyr Ser Gln Ser Asn Gln Leu
                485                 490                 495

Leu Ser Tyr Gly Asp Val Thr Arg Phe Leu Ser Asn Asn Ser Met Val
            500                 505                 510

Leu Tyr Thr Asp Val Ser Gln Trp Asp Ser Ser Gln His Asn Thr Gln
        515                 520                 525

Pro Phe Arg Lys Gly Ile Ile Met Gly Leu Asp Met Leu Ala Asn Met
    530                 535                 540

Thr Asn Asp Ala Arg Val Ile Gln Thr Leu Asn Leu Tyr Lys Gln Thr
545                 550                 555                 560

Gln Ile Asn Leu Met Asp Ser Tyr Val Gln Ile Pro Asp Gly Asn Val
                565                 570                 575

Ile Lys Lys Ile Gln Tyr Gly Ala Val Ala Ser Gly Glu Lys Gln Thr
```

-continued

```
            580             585             590
Lys Ala Ala Asn Ser Ile Ala Asn Leu Ala Leu Ile Lys Thr Val Leu
            595             600             605
Ser Arg Ile Ser Asn Lys Tyr Ser Phe Ala Thr Lys Ile Ile Arg Val
            610             615             620
Asp Gly Asp Asp Asn Tyr Ala Val Leu Gln Phe Asn Thr Glu Val Thr
625             630             635             640
Lys Gln Met Val Gln Asp Val Ser Asn Asp Val Arg Glu Thr Tyr Ala
            645             650             655
Arg Met Asn Thr Lys Val Lys Ala Leu Val Ser Thr Val Gly Ile Glu
            660             665             670
Ile Ala Lys Arg Tyr Ile Ala Gly Gly Lys Ile Phe Phe Arg Ala Gly
            675             680             685
Ile Asn Leu Leu Asn Asn Glu Lys Lys Gly Gln Ser Thr Gln Trp Asp
            690             695             700
Gln Ala Ala Val Lys Asn Tyr Ile Val Asn Arg Leu Arg Gly Phe Glu
705             710             715             720
Thr Asp Arg Glu Phe Ile Leu Thr Lys Ile Met Gln Met Thr Ser Val
            725             730             735
Ala Ile Thr Gly Ser Leu Arg Leu Phe Pro Ser Val Leu Thr Thr Asn
            740             745             750
Ser Thr Phe Lys Val Phe Asp Ser Glu Asp Phe Ile Ile Glu Tyr Gly
            755             760             765
Thr Thr Asp Asp Glu Val Tyr Ile Gln Arg Ala Phe Met Ser Leu Ser
            770             775             780
Ser Gln Lys Ser Gly Ile Ala Asp Glu Ile Ala Ala Ser Ser Thr Phe
785             790             795             800
Lys Asn Tyr Val Ser Arg Leu Ser Glu Gln Leu Leu Phe Ser Lys Asn
            805             810             815
Asn Ile Val Ser Arg Gly Ile Ala Leu Thr Glu Lys Ala Lys Leu Asn
            820             825             830
Ser Tyr Ala Pro Ile Ser Leu Glu Lys Arg Arg Ala Gln Ile Ser Ala
            835             840             845
Leu Leu Thr Met Leu Gln Lys Pro Val Thr Phe Lys Ser Ser Lys Ile
            850             855             860
Thr Ile Asn Asp Ile Leu Arg Asp Ile Lys Pro Phe Phe Thr Val Asn
865             870             875             880
Glu Ala His Leu Pro Ile Gln Tyr Gln Lys Phe Met Pro Thr Leu Pro
            885             890             895
Asp Asn Val Gln Tyr Ile Ile Gln Cys Ile Gly Ser Arg Thr Tyr Gln
            900             905             910
Ile Glu Asp Asp Gly Ser Lys Ser Ala Ile Ser Arg Leu Ile Ser Lys
            915             920             925
Tyr Ser Val Tyr Lys Pro Ser Ile Glu Leu Tyr Lys Val Ile Ser
            930             935             940
Leu His Glu Asn Glu Ile Gln Leu Tyr Leu Ile Ser Leu Gly Ile Pro
945             950             955             960
Lys Ile Asp Ala Asp Thr Tyr Val Gly Ser Lys Ile Tyr Ser Gln Asp
            965             970             975
Lys Tyr Arg Ile Ser Tyr Val Tyr Asn Leu Leu Ser Ile Asn Tyr Gly
            980             985             990
Cys Tyr Gln Leu Phe Asp Phe Asn Ser Pro Asp Leu Glu Lys Leu Ile
            995             1000            1005
```

Arg Ile Pro Phe Lys Gly Lys Ile Pro Ala Val Thr Phe Ile Leu His
    1010                1015                1020

Leu Tyr Ala Lys Leu Glu Val Ile Asn His Ala Ile Lys Asn Gly Ser
1025                1030                1035                1040

Trp Ile Ser Leu Phe Cys Asn Tyr Pro Lys Ser Glu Met Ile Lys Leu
            1045                1050                1055

Trp Lys Lys Met Trp Asn Ile Thr Ser Leu Arg Ser Pro Tyr Thr Asn
            1060                1065                1070

Ala Asn Phe Phe Gln Asp
        1075

<210> SEQ ID NO 16
<211> LENGTH: 885
<212> TYPE: PRT
<213> ORGANISM: Rotavirus

<400> SEQUENCE: 16

Met Ala Tyr Arg Lys Arg Gly Ala Arg Arg Glu Thr Asn Leu Lys Gln
 1               5                  10                  15

Asp Asp Arg Met Gln Glu Lys Glu Glu Asn Lys Asn Val Asn Thr Asn
            20                  25                  30

Ser Glu Asn Lys Asn Ala Thr Lys Pro Gln Leu Ser Glu Lys Val Leu
        35                  40                  45

Ser Gln Lys Glu Glu Val Ile Thr Asp Asn Gln Glu Glu Ile Lys Ile
    50                  55                  60

Ala Asp Glu Val Lys Lys Ser Asn Lys Glu Glu Ser Lys Gln Leu Leu
65                  70                  75                  80

Glu Val Leu Lys Thr Lys Glu Glu His Gln Lys Glu Val Gln Tyr Glu
                85                  90                  95

Ile Leu Gln Lys Thr Ile Pro Thr Phe Glu Pro Lys Glu Ser Ile Leu
            100                 105                 110

Lys Lys Leu Glu Asp Ile Lys Pro Glu Gln Val Lys Lys Gln Thr Lys
        115                 120                 125

Leu Phe Arg Ile Phe Glu Pro Arg Gln Leu Pro Val Tyr Arg Ala Asn
    130                 135                 140

Gly Glu Lys Glu Leu Arg Asn Arg Trp Tyr Trp Lys Leu Lys Arg Asp
145                 150                 155                 160

Thr Leu Pro Asp Gly Asp Tyr Asp Val Arg Glu Tyr Phe Leu Asn Leu
                165                 170                 175

Tyr Asp Gln Val Leu Thr Glu Met Pro Asp Tyr Leu Leu Leu Lys Asp
            180                 185                 190

Met Ala Val Glu Asn Lys Asn Ser Arg Asp Ala Gly Lys Val Val Asp
        195                 200                 205

Ser Glu Thr Ala Ala Ile Cys Asp Ala Ile Phe Gln Asp Glu Glu Thr
    210                 215                 220

Glu Gly Val Val Arg Arg Phe Ile Ala Glu Met Arg Gln Arg Val Gln
225                 230                 235                 240

Ala Asp Arg Asn Val Val Asn Tyr Pro Ser Ile Leu His Pro Ile Asp
                245                 250                 255

His Ala Phe Asn Glu Tyr Phe Leu Gln His Gln Leu Val Glu Pro Leu
            260                 265                 270

Asn Asn Asp Ile Ile Phe Asn Tyr Ile Pro Glu Arg Ile Arg Asn Asp
        275                 280                 285

Val Asn Tyr Ile Leu Asn Met Asp Arg Asn Leu Pro Ser Thr Ala Arg

-continued

```
              290                 295                 300
Tyr Ile Arg Pro Asn Leu Leu Gln Asp Arg Leu Asn Leu His Asp Asn
305                 310                 315                 320

Phe Glu Ser Leu Trp Asp Thr Ile Thr Thr Ser Asn Tyr Ile Leu Ala
                    325                 330                 335

Arg Ser Val Val Pro Asp Leu Lys Glu Leu Val Ser Thr Glu Ala Gln
                    340                 345                 350

Ile Gln Lys Met Ser Gln Asp Leu Gln Leu Glu Ala Leu Thr Ile Gln
                355                 360                 365

Ser Glu Thr Gln Phe Leu Thr Gly Ile Asn Ser Gln Ala Ala Asn Asp
370                 375                 380

Cys Phe Lys Thr Leu Ile Ala Ala Met Leu Ser Gln Arg Thr Met Ser
385                 390                 395                 400

Leu Asp Phe Val Thr Thr Asn Tyr Met Ser Leu Ile Ser Gly Met Trp
                    405                 410                 415

Leu Leu Thr Val Val Pro Asn Asp Met Phe Ile Arg Glu Ser Leu Val
                    420                 425                 430

Ala Cys Gln Leu Ala Ile Ile Asn Thr Ile Ile Tyr Pro Ala Phe Gly
                435                 440                 445

Met Gln Arg Met His Tyr Arg Asn Gly Asp Pro Gln Thr Pro Phe Gln
                450                 455                 460

Ile Ala Glu Gln Gln Ile Gln Asn Phe Gln Val Ala Asn Trp Leu His
465                 470                 475                 480

Phe Val Asn Asn Asn Gln Phe Arg Gln Val Val Ile Asp Gly Val Leu
                    485                 490                 495

Asn Gln Val Leu Asn Asp Asn Ile Arg Asn Gly His Val Val Asn Gln
                    500                 505                 510

Leu Met Glu Ala Leu Met Gln Leu Ser Arg Gln Gln Phe Pro Thr Met
                515                 520                 525

Pro Val Asp Tyr Lys Arg Ser Ile Gln Arg Gly Ile Leu Leu Leu Ser
                530                 535                 540

Asn Arg Leu Gly Gln Leu Val Asp Leu Thr Arg Leu Leu Ala Tyr Asn
545                 550                 555                 560

Tyr Glu Thr Leu Met Ala Cys Ile Thr Met Asn Met Gln His Val Gln
                    565                 570                 575

Thr Leu Thr Thr Glu Lys Leu Gln Leu Thr Ser Val Thr Ser Leu Cys
                    580                 585                 590

Met Leu Ile Gly Asn Ala Thr Val Ile Pro Ser Pro Gln Thr Leu Phe
                595                 600                 605

His Tyr Tyr Asn Val Asn Val Asn Phe His Ser Asn Tyr Asn Glu Arg
610                 615                 620

Ile Asn Asp Ala Val Ala Ile Ile Thr Ala Ala Asn Arg Leu Asn Leu
625                 630                 635                 640

Tyr Gln Lys Lys Met Lys Ser Ile Val Glu Asp Phe Leu Lys Arg Leu
                    645                 650                 655

Gln Ile Phe Asp Ile Ser Arg Val Pro Asp Asp Gln Met Tyr Arg Leu
                    660                 665                 670

Arg Asp Arg Leu Arg Leu Leu Pro Val Glu Ile Arg Arg Leu Asp Ile
                675                 680                 685

Phe Asn Leu Ile Leu Met Asn Met Glu Gln Ile Glu Arg Ala Ser Asp
                690                 695                 700

Lys Ile Ala Gln Gly Val Ile Ile Ala Tyr Arg Asp Met Gln Leu Glu
705                 710                 715                 720
```

```
Arg Asp Glu Met Tyr Gly Tyr Val Asn Ile Ala Arg Asn Leu Asp Gly
            725                 730                 735

Phe Gln Gln Ile Asn Leu Glu Glu Leu Met Arg Thr Gly Asp Tyr Ala
            740                 745                 750

Gln Ile Thr Asn Met Leu Leu Asn Asn Gln Pro Val Gly Ala Leu
            755                 760                 765

Pro Phe Ile Thr Asp Ser Ser Val Ile Ser Leu Val Ala Lys Leu Asp
            770                 775                 780

Ala Thr Val Phe Ala Gln Ile Val Lys Leu Arg Lys Val Asp Thr Leu
785                 790                 795                 800

Lys Pro Ile Leu Tyr Lys Ile Asn Ser Asp Ser Asn Asp Phe Tyr Leu
            805                 810                 815

Val Ala Asn Tyr Asp Trp Val Pro Thr Ser Thr Thr Lys Val Tyr Lys
            820                 825                 830

Gln Ile Pro Gln Gln Phe Asp Phe Arg Ala Ser Met His Met Leu Thr
            835                 840                 845

Ser Asn Leu Thr Phe Thr Val Tyr Ser Asp Leu Leu Ala Phe Val Ser
            850                 855                 860

Ala Asp Thr Val Glu Pro Ile Asn Ala Val Ala Phe Asp Asn Met Arg
865                 870                 875                 880

Ile Met Asn Glu Leu
            885

<210> SEQ ID NO 17
<211> LENGTH: 831
<212> TYPE: PRT
<213> ORGANISM: Rotavirus

<400> SEQUENCE: 17

Met Lys Val Leu Ala Leu Arg His Gly Val Ala Gln Val Tyr Ala Asp
1               5                   10                  15

Thr Gln Ile Tyr Thr His Asp Asp Thr Lys Asp Ser Tyr Glu Asn Ala
            20                  25                  30

Phe Leu Ile Ser Asn Leu Thr Thr His Asn Ile Leu Tyr Leu Asn Tyr
            35                  40                  45

Ser Ile Lys Thr Leu Glu Ile Leu Asn Lys Ser Gly Ile Ala Ala Val
50                  55                  60

Glu Ile Gln Ser Leu Glu Glu Leu Phe Thr Leu Ile Arg Cys Asn Phe
65                  70                  75                  80

Thr Tyr Asp Tyr Glu Asn Asn Ile Ile Tyr Leu His Asp Tyr Ser Tyr
            85                  90                  95

Tyr Thr Asn Asn Glu Ile Arg Thr Asp Gln His Trp Val Thr Lys Thr
            100                 105                 110

Asp Ile Glu Glu Tyr Leu Leu Pro Gly Trp Lys Leu Thr Tyr Val Gly
            115                 120                 125

Tyr Asn Gly Ser Asp Thr Arg Gly His Tyr Asn Phe Ser Phe Thr Cys
            130                 135                 140

Gln Asn Ala Ala Thr Asp Asp Leu Ile Ile Glu Tyr Ile Tyr Ser
145                 150                 155                 160

Glu Ala Leu Asp Phe Gln Asn Phe Met Leu Lys Lys Ile Lys Glu Arg
            165                 170                 175

Met Thr Thr Ser Leu Pro Ile Ala Arg Leu Ser Asn Arg Val Phe Arg
            180                 185                 190

Asp Lys Leu Phe Pro Leu Leu Ser Glu Lys His Gln Arg Ile Val Asn
```

```
                195                 200                 205
Ile Gly Pro Arg Asn Glu Ser Met Phe Thr Phe Leu Asn Phe Pro Ser
210                 215                 220
Ile Lys Gln Phe Ser Asn Gly Pro Tyr Leu Val Lys Asp Thr Ile Lys
225                 230                 235                 240
Leu Lys Gln Glu Arg Trp Leu Gly Lys Arg Val Ser Gln Phe Asp Ile
                245                 250                 255
Gly Gln Tyr Lys Asn Met Met Asn Val Ile Thr Thr Val Tyr Tyr Tyr
                260                 265                 270
Tyr Asn Leu Tyr Gln Lys Lys Pro Ile Ile Tyr Met Val Gly Ser Ala
            275                 280                 285
Pro Ser Tyr Trp Ile Tyr Asp Val Lys Gln Tyr Ser Asp Phe Met Phe
290                 295                 300
Glu Thr Trp Asp Pro Leu Asp Thr Pro Tyr Ser Ser Val His His Lys
305                 310                 315                 320
Glu Leu Phe Phe Glu Lys Asp Ile Thr Arg Leu Lys Asp Asp Ser Ile
                325                 330                 335
Leu Tyr Ile Asp Ile Arg Thr Asp Arg Gly Asn Thr Asp Trp Lys Glu
            340                 345                 350
Trp Arg Lys Ile Val Glu Ala Gln Thr Ile Ser Asn Leu Lys Leu Ala
            355                 360                 365
Tyr Arg Tyr Leu Ser Gly Gly Lys Ser Lys Val Cys Cys Val Lys Met
        370                 375                 380
Thr Ala Met Asp Leu Glu Leu Pro Ile Ser Ala Lys Leu Leu His His
385                 390                 395                 400
Pro Thr Thr Glu Ile Arg Ser Glu Phe Tyr Leu Leu Leu Asp Ile Trp
                405                 410                 415
Asp Ile Ser Asn Val Lys Arg Phe Ile Pro Lys Gly Val Lys Phe Ile
                420                 425                 430
Asn Asn Val Thr Thr Glu Asn Val Phe Ile Gln Pro Pro Phe Lys Ile
            435                 440                 445
Lys Pro Phe Lys Asn Asp Tyr Ile Val Tyr Ala Leu Ser Asn Asp Phe
450                 455                 460
Asn Asp Arg Thr Asp Val Ile Asn Leu Ile Asn Asn Gln Lys Gln Ser
465                 470                 475                 480
Leu Ile Thr Val Arg Ile Asn Asn Thr Phe Lys Asp Glu Pro Lys Val
                485                 490                 495
Gly Phe Lys Asn Ile Tyr Asp Trp Thr Phe Leu Pro Thr Asp Phe Thr
                500                 505                 510
Thr Thr Asp Ala Ile Ile Thr Ser Tyr Asp Gly Cys Leu Gly Ile Phe
            515                 520                 525
Gly Leu Ser Ile Ser Leu Ala Ser Lys Pro Thr Gly Asn Asn His Leu
            530                 535                 540
Phe Ile Leu Asn Gly Thr Asp Lys Tyr Tyr Lys Leu Asp Gln Phe Ala
545                 550                 555                 560
Asn His Thr Gly Ile Ser Arg Arg Ser His Gln Ile Arg Phe Ser Glu
                565                 570                 575
Ser Ala Thr Ser Tyr Ser Gly Tyr Ile Phe Arg Asp Leu Ser Asn Asn
            580                 585                 590
Asn Phe Asn Leu Ile Gly Thr Asn Val Glu Asn Ser Val Ser Gly His
        595                 600                 605
Val Tyr Asn Ala Leu Ile Tyr Tyr Arg Tyr Asn Tyr Ser Phe Asp Leu
    610                 615                 620
```

```
Lys Arg Trp Ile Tyr Leu His Ser Ile Glu Lys Ala Asp Ile Glu Gly
625                 630                 635                 640

Gly Lys Tyr Tyr Glu His Ala Pro Ile Glu Leu Ile Tyr Ala Cys Arg
            645                 650                 655

Ser Ala Lys Glu Phe Ala Leu Leu Gln Asp Asp Leu Thr Val Leu Arg
            660                 665                 670

Tyr Ala Asn Glu Ile Glu Ser Tyr Ile Asn Lys Val Tyr Ser Ile Thr
            675                 680                 685

Tyr Ala Asp Asp Pro Asn Tyr Phe Ile Gly Ile Lys Phe Arg His Ile
690                 695                 700

Pro Tyr Glu Tyr Asp Val Lys Ile Pro His Leu Thr Phe Gly Val Leu
705                 710                 715                 720

Phe Ile Ser Asp Asn Met Ile Pro Asp Val Val Glu Ile Met Lys Ile
                725                 730                 735

Met Lys Lys Glu Leu Phe Glu Met Asp Ile Thr Thr Ser Tyr Thr Tyr
            740                 745                 750

Met Leu Ser Asp Gly Ile Tyr Val Ala Asn Val Ser Gly Val Leu Ala
            755                 760                 765

Thr Tyr Phe Lys Met Tyr Asn Leu Phe Tyr Lys Ser Gln Ile Thr Phe
770                 775                 780

Gly Gln Ser Arg Met Phe Ile Pro His Ile Thr Leu Ser Phe Ser Asn
785                 790                 795                 800

Asn Lys Thr Val Arg Ile Glu Ser Thr Arg Leu Lys Ile Ser Ser Ile
                805                 810                 815

Tyr Leu Arg Lys Ile Lys Gly Asp Thr Val Phe Asp Met Ser Glu
            820                 825                 830

<210> SEQ ID NO 18
<211> LENGTH: 776
<212> TYPE: PRT
<213> ORGANISM: Rotavirus

<400> SEQUENCE: 18

Met Ala Ser Leu Ile Tyr Arg Gln Leu Leu Thr Asn Ser Tyr Thr Val
1               5                   10                  15

Asp Leu Ser Asp Glu Ile Gln Glu Ile Gly Ser Thr Lys Thr Gln Asn
            20                  25                  30

Val Thr Ile Asn Leu Gly Pro Phe Ala Gln Thr Gly Tyr Ala Pro Val
            35                  40                  45

Asn Trp Gly Pro Gly Glu Thr Asn Asp Ser Thr Thr Val Glu Pro Val
        50                  55                  60

Leu Asp Gly Pro Tyr Gln Pro Thr Thr Phe Asn Pro Pro Val Asp Tyr
65                  70                  75                  80

Trp Met Leu Leu Ala Pro Thr Ala Ala Gly Val Val Val Glu Gly Thr
                85                  90                  95

Asn Asn Thr Asp Arg Trp Leu Ala Thr Ile Leu Val Glu Pro Asn Val
            100                 105                 110

Thr Ser Glu Thr Arg Ser Tyr Thr Leu Phe Gly Thr Gln Glu Gln Ile
        115                 120                 125

Thr Ile Ala Asn Ala Ser Gln Thr Gln Trp Lys Phe Ile Asp Val Val
    130                 135                 140

Lys Thr Thr Gln Asn Gly Ser Tyr Ser Gln Tyr Gly Pro Leu Gln Ser
145                 150                 155                 160

Thr Pro Lys Leu Tyr Ala Val Met Lys His Asn Gly Lys Ile Tyr Thr
```

-continued

```
                165                 170                 175
Tyr Asn Gly Glu Thr Pro Asn Val Thr Thr Lys Tyr Tyr Ser Thr Thr
                    180                 185                 190
Asn Tyr Asp Ser Val Asn Met Thr Ala Phe Cys Asp Phe Tyr Ile Ile
                195                 200                 205
Pro Arg Glu Glu Ser Thr Cys Thr Glu Tyr Ile Asn Asn Gly Leu
            210                 215                 220
Pro Pro Ile Gln Asn Thr Arg Asn Ile Val Pro Leu Ala Leu Ser Ala
225                 230                 235                 240
Arg Asn Ile Ile Ser His Arg Ala Gln Ala Asn Glu Asp Ile Val Val
                    245                 250                 255
Ser Lys Thr Ser Leu Trp Lys Glu Met Gln Tyr Asn Arg Asp Ile Thr
                260                 265                 270
Ile Arg Phe Lys Phe Ala Ser Ser Ile Val Lys Ser Gly Gly Leu Gly
                275                 280                 285
Tyr Lys Trp Ser Glu Ile Ser Phe Lys Pro Ala Asn Tyr Gln Tyr Thr
                290                 295                 300
Tyr Thr Arg Asp Gly Glu Glu Val Thr Ala His Thr Thr Cys Ser Val
305                 310                 315                 320
Asn Gly Met Asn Asp Phe Asn Phe Asn Gly Gly Ser Leu Pro Thr Asp
                    325                 330                 335
Phe Val Ile Ser Arg Tyr Glu Val Ile Lys Glu Asn Ser Tyr Val Tyr
                340                 345                 350
Val Asp Tyr Trp Asp Asp Ser Gln Ala Phe Arg Asn Met Val Tyr Val
                355                 360                 365
Arg Ser Leu Ala Ala Asn Leu Asn Ser Val Ile Cys Thr Gly Gly Asp
370                 375                 380
Tyr Ser Phe Ala Leu Pro Val Gly Gln Trp Pro Val Met Thr Gly Gly
385                 390                 395                 400
Ala Val Ser Leu His Ser Ala Gly Val Thr Leu Ser Thr Gln Phe Thr
                    405                 410                 415
Asp Phe Val Ser Leu Asn Ser Leu Arg Phe Arg Phe Arg Leu Thr Val
                420                 425                 430
Glu Glu Pro Ser Phe Ser Ile Thr Arg Thr Arg Val Ser Arg Leu Tyr
            435                 440                 445
Gly Leu Pro Ala Ala Asn Pro Asn Asn Gly Lys Glu Tyr Tyr Glu Val
            450                 455                 460
Ala Gly Arg Phe Ser Leu Ile Ser Leu Val Pro Ser Asn Asp Asp Tyr
465                 470                 475                 480
Gln Thr Pro Ile Thr Asn Ser Val Thr Val Arg Gln Asp Leu Glu Arg
                    485                 490                 495
Gln Leu Gly Glu Leu Arg Glu Glu Phe Asn Ala Leu Ser Gln Glu Ile
                500                 505                 510
Ala Met Ser Gln Leu Ile Asp Leu Ala Leu Leu Pro Leu Asp Met Phe
            515                 520                 525
Ser Met Phe Ser Gly Ile Lys Ser Thr Ile Asp Ala Ala Lys Ser Met
            530                 535                 540
Ala Thr Ser Val Met Lys Lys Phe Lys Lys Ser Gly Leu Ala Asn Ser
545                 550                 555                 560
Val Ser Thr Leu Thr Asp Ser Leu Ser Asp Ala Ala Ser Ser Ile Ser
                    565                 570                 575
Arg Gly Ala Ser Ile Arg Ser Val Gly Ser Ser Ala Ser Ala Trp Thr
                580                 585                 590
```

```
Asp Val Ser Thr Gln Ile Thr Asp Val Ser Ser Val Ser Ser Ile
            595                 600                 605
Ser Thr Gln Thr Ser Thr Ile Ser Arg Arg Leu Arg Leu Lys Glu Met
        610                 615                 620
Ala Thr Gln Thr Glu Gly Met Asn Phe Asp Asp Ile Ser Ala Ala Val
625                 630                 635                 640
Leu Lys Thr Lys Ile Asp Arg Ser Thr Gln Ile Ser Pro Asn Thr Leu
                645                 650                 655
Pro Asp Ile Val Thr Glu Ala Ser Glu Lys Phe Ile Pro Asn Arg Ala
            660                 665                 670
Tyr Arg Val Ile Asn Asn Asp Glu Val Phe Glu Ala Gly Thr Asp Gly
        675                 680                 685
Arg Phe Phe Ala Tyr Arg Val Glu Thr Phe Asp Glu Ile Pro Phe Asp
    690                 695                 700
Val Gln Lys Phe Ala Asp Leu Val Thr Asp Ser Pro Val Ile Ser Ala
705                 710                 715                 720
Ile Ile Asp Phe Lys Thr Leu Lys Asn Leu Asn Asp Asn Tyr Gly Ile
                725                 730                 735
Ser Arg Gln Gln Ala Phe Asn Leu Leu Arg Ser Asp Pro Arg Val Leu
            740                 745                 750
Arg Glu Phe Ile Asn Gln Asp Asn Pro Ile Ile Arg Asn Arg Ile Glu
        755                 760                 765
Gln Leu Ile Met Gln Cys Arg Leu
    770                 775

<210> SEQ ID NO 19
<211> LENGTH: 492
<212> TYPE: PRT
<213> ORGANISM: Rotavirus

<400> SEQUENCE: 19

Met Ala Thr Phe Lys Asp Ala Cys Phe His Tyr Arg Arg Val Thr Lys
1               5                   10                  15
Leu Asn Arg Glu Leu Leu Arg Ile Gly Ala Asn Ser Val Trp Thr Pro
            20                  25                  30
Val Ser Ser Asn Lys Ile Lys Ile Lys Gly Trp Cys Ile Glu Cys Cys
        35                  40                  45
Gln Leu Thr Gly Leu Thr Phe Cys His Gly Cys Ser Leu Ala His Val
    50                  55                  60
Cys Gln Trp Cys Ile Gln Asn Lys Arg Cys Phe Leu Asp Asn Glu Pro
65                  70                  75                  80
His Leu Leu Lys Leu Arg Thr Phe Glu Ser Pro Ile Thr Lys Glu Lys
                85                  90                  95
Leu Gln Cys Ile Ile Asn Leu Tyr Glu Leu Leu Phe Pro Ile Asn His
            100                 105                 110
Gly Val Ile Asn Lys Phe Lys Lys Thr Ile Lys Gln Arg Lys Cys Arg
        115                 120                 125
Asn Glu Phe Asp Lys Ser Trp Tyr Asn Gln Leu Leu Pro Ile Thr
    130                 135                 140
Leu Asn Ala Ala Val Phe Lys Phe His Ser Arg Asp Val Tyr Val Phe
145                 150                 155                 160
Gly Phe Tyr Glu Gly Ser Ser Pro Cys Ile Asp Leu Pro Tyr Arg Leu
                165                 170                 175
Val Asn Cys Ile Asp Leu Tyr Asp Lys Leu Leu Leu Asp Gln Val Asn
```

-continued

```
                180             185             190
Phe Glu Arg Met Ser Ser Leu Pro Asp Asn Leu Gln Ser Ile Tyr Ala
            195                 200                 205

Asn Lys Tyr Phe Lys Leu Ser Arg Leu Pro Ser Met Lys Leu Lys Arg
        210                 215                 220

Ile Tyr Tyr Ser Asp Phe Ser Lys Gln Asn Leu Ile Asn Lys Tyr Lys
225                 230                 235                 240

Thr Lys Ser Arg Ile Val Leu Arg Asn Leu Thr Glu Phe Thr Trp Asp
                245                 250                 255

Ser Gln Thr Asp Leu His His Asp Leu Ile Asn Asp Lys Asp Lys Ile
            260                 265                 270

Leu Ala Ala Leu Ser Thr Ser Ser Leu Lys Gln Phe Glu Thr His Asp
        275                 280                 285

Leu Asn Leu Gly Arg Ile Lys Ala Asp Ile Phe Glu Leu Gly His His
    290                 295                 300

Cys Lys Pro Asn Tyr Ile Ser Ser Asn His Trp Gln Pro Ala Ser Lys
305                 310                 315                 320

Ile Ser Lys Cys Lys Trp Cys Asn Val Lys Tyr Ala Phe Arg Asp Met
                325                 330                 335

Asp Trp Lys Met Glu Ser Met Tyr Asn Glu Leu Leu Ser Phe Ile Gln
            340                 345                 350

Ser Cys Tyr Lys Ser Asn Val Asn Val Gly His Cys Ser Ser Ile Glu
        355                 360                 365

Lys Ala Tyr Pro Leu Val Lys Asp Ile Leu Trp His Ser Ile Thr Glu
    370                 375                 380

Tyr Ile Asp Gln Thr Val Glu Lys Leu Phe Asn Thr Met Asn Pro Val
385                 390                 395                 400

Gln Val Asn Glu Gln Gln Val Ile Lys Phe Cys Trp Gln Ile Asp Ile
                405                 410                 415

Ala Leu Tyr Met His Ile Lys Met Ile Thr Glu Ala Leu Pro Phe Thr
            420                 425                 430

Phe Thr Leu Asn Gln Phe Asn Ser Ile Ile Lys Gly Ile Val Asn Gln
        435                 440                 445

Trp Cys Asp Val Ala Glu Leu Asp His Leu Pro Leu Cys Thr Glu Gln
    450                 455                 460

Thr Asp Ala Leu Val Lys Leu Glu Glu Glu Gly Lys Leu Ser Glu Glu
465                 470                 475                 480

Tyr Glu Leu Leu Ile Ser Asp Ser Glu Asp Asp
                485                 490

<210> SEQ ID NO 20
<211> LENGTH: 393
<212> TYPE: PRT
<213> ORGANISM: Rotavirus

<400> SEQUENCE: 20

Met Asp Val Lys Leu Ser Lys Thr Leu Lys Asp Ala Arg Asp Lys Ile
1               5                   10                  15

Val Glu Gly Thr Lys Asn Val Ser Asp Leu Ile Gln Gln Phe Asn Gln
            20                  25                  30

Met Ile Ile Thr Met Asn Gly Asn Glu Phe Gln Thr Gly Gly Ile Gly
        35                  40                  45

Asn Leu Pro Ile Arg Asn Trp Asn Phe Asp Phe Gly Leu Leu Gly Thr
    50                  55                  60
```

```
Thr Leu Leu Asn Leu Asp Ala Asn Tyr Val Glu Thr Ala Arg Asn Thr
 65                  70                  75                  80

Ile Asp Tyr Phe Val Asp Phe Val Asp Asn Val Cys Met Asp Glu Met
                 85                  90                  95

Val Arg Glu Ser Gln Arg Asn Gly Ile Ala Pro Gln Ser Asp Ser Leu
            100                 105                 110

Arg Lys Leu Ser Gly Ile Lys Phe Lys Arg Ile Asn Phe Asp Asn Ser
        115                 120                 125

Ser Glu Tyr Ile Glu Asn Trp Asn Leu Gln Asn Arg Arg Gln Arg Thr
    130                 135                 140

Gly Phe Thr Phe His Lys Pro Asn Ile Phe Pro Tyr Ser Ala Ser Phe
145                 150                 155                 160

Thr Leu Asn Arg Ser Gln Pro Ala His Asp Asn Leu Met Gly Thr Met
                165                 170                 175

Trp Leu Asn Ala Gly Ser Glu Ile Gln Val Ala Gly Phe Asp Tyr Ser
            180                 185                 190

Cys Ala Ile Asn Ala Pro Ala Asn Ile Gln Gln Phe Glu His Ile Val
        195                 200                 205

Gln Leu Arg Arg Val Leu Thr Thr Ala Thr Ile Thr Leu Leu Pro Asp
    210                 215                 220

Ala Glu Arg Phe Ser Phe Pro Arg Val Ile Asn Ser Ala Asp Gly Ala
225                 230                 235                 240

Ala Thr Trp Tyr Phe Asn Pro Val Ile Leu Arg Pro Asn Asn Val Glu
                245                 250                 255

Val Glu Phe Leu Leu Asn Gly Gln Ile Ile Asn Thr Tyr Gln Ala Arg
            260                 265                 270

Phe Gly Thr Ile Ile Ala Arg Asn Phe Asp Thr Ile Arg Leu Ser Phe
        275                 280                 285

Gln Leu Met Arg Pro Pro Asn Met Thr Pro Ala Val Ala Ala Leu Phe
    290                 295                 300

Pro Asn Ala Gln Pro Phe Glu His His Ala Thr Val Gly Leu Thr Leu
305                 310                 315                 320

Arg Ile Glu Ser Ala Val Cys Glu Ser Val Leu Ala Asp Ala Ser Lys
                325                 330                 335

Thr Met Leu Ala Asn Val Thr Ser Val Arg Gln Glu Tyr Ala Ile Pro
            340                 345                 350

Val Gly Pro Val Phe Pro Pro Gly Met Asn Trp Thr Asp Leu Ile Thr
        355                 360                 365

Asn Tyr Ser Pro Ser Arg Glu Asp Asn Leu Gln Arg Val Phe Thr Val
    370                 375                 380

Ala Ser Ile Arg Ser Met Leu Val Lys
385                 390

<210> SEQ ID NO 21
<211> LENGTH: 313
<212> TYPE: PRT
<213> ORGANISM: Rotavirus

<400> SEQUENCE: 21

Met Leu Lys Met Glu Ser Thr Gln Gln Met Ala Ser Ser Ile Ile Asn
 1               5                  10                  15

Ser Ser Phe Glu Ala Ala Val Val Ala Ala Thr Ser Thr Leu Glu Leu
                20                  25                  30

Met Gly Ile Gln Tyr Asp Tyr Asn Glu Val Tyr Thr Arg Val Lys Ser
            35                  40                  45
```

```
Lys Phe Asp Leu Val Met Asp Asp Ser Gly Val Lys Asn Asn Leu Ile
         50                  55                  60

Gly Lys Ala Ile Thr Ile Asp Gln Ala Leu Asn Gly Lys Phe Ser Ser
 65                  70                  75                  80

Ala Ile Arg Asn Arg Asn Trp Met Thr Asp Ser Arg Thr Val Ala Lys
                 85                  90                  95

Leu Asp Glu Asp Val Asn Lys Leu Arg Ile Met Leu Ser Ser Lys Gly
            100                 105                 110

Ile Asp Gln Lys Met Arg Val Leu Asn Ala Cys Phe Ser Val Lys Arg
        115                 120                 125

Ile Pro Gly Lys Ser Ser Ile Val Lys Cys Thr Arg Leu Met Lys
    130                 135                 140

Asp Lys Leu Glu Arg Gly Glu Val Glu Val Asp Ser Phe Val Glu
145                 150                 155                 160

Glu Lys Met Glu Val Asp Thr Ile Asp Trp Lys Ser Arg Tyr Glu Gln
                165                 170                 175

Leu Glu Lys Arg Phe Glu Ser Leu Lys His Arg Val Asn Glu Lys Tyr
            180                 185                 190

Asn His Trp Val Leu Lys Ala Arg Lys Val Asn Glu Asn Met Asn Ser
        195                 200                 205

Leu Gln Asn Val Ile Ser Gln Gln Ala His Ile Asn Glu Leu Gln
    210                 215                 220

Met Tyr Asn Asn Lys Leu Glu Arg Asp Leu Gln Ser Lys Ile Gly Ser
225                 230                 235                 240

Val Val Ser Ser Ile Glu Trp Tyr Leu Arg Ser Met Glu Leu Ser Asp
                245                 250                 255

Asp Val Lys Ser Asp Ile Glu Gln Gln Leu Asn Ser Ile Asp Gln Leu
            260                 265                 270

Asn Pro Val Asn Ala Ile Asp Asp Phe Glu Ser Ile Leu Arg Asn Leu
        275                 280                 285

Ile Ser Asp Tyr Asp Arg Leu Phe Ile Met Phe Lys Gly Leu Leu Gln
    290                 295                 300

Gln Cys Asn Tyr Thr Tyr Thr Tyr Glu
305                 310

<210> SEQ ID NO 22
<211> LENGTH: 317
<212> TYPE: PRT
<213> ORGANISM: Rotavirus

<400> SEQUENCE: 22

Met Ala Glu Leu Ala Cys Phe Cys Tyr Pro His Leu Glu Asn Asp Ser
 1               5                  10                  15

Tyr Arg Phe Ile Pro Phe Asn Ser Leu Ala Ile Lys Cys Met Leu Thr
                20                  25                  30

Ala Lys Val Asp Lys Lys Asp Gln Asp Lys Phe Tyr Asn Ser Ile Ile
            35                  40                  45

Tyr Gly Ile Ala Pro Pro Pro Gln Phe Lys Lys Arg Tyr Asn Thr Asn
        50                  55                  60

Asp Asn Ser Arg Gly Met Asn Tyr Glu Thr Pro Met Phe Asn Lys Val
 65                 70                  75                  80

Ala Val Leu Ile Cys Glu Ala Leu Asn Ser Ile Lys Val Thr Gln Ser
                85                  90                  95

Asp Val Ala Asn Val Leu Ser Lys Val Val Ser Val Arg His Leu Glu
```

```
                    100                 105                 110
Asn Leu Val Leu Arg Arg Glu Asn His Gln Asp Val Leu Phe His Ser
                115                 120                 125
Lys Glu Leu Leu Leu Lys Ser Val Leu Ile Ala Ile Gly His Ser Lys
            130                 135                 140
Glu Ile Glu Thr Thr Ala Thr Ala Glu Gly Gly Glu Ile Val Phe Gln
145                 150                 155                 160
Asn Ala Ala Phe Thr Met Trp Lys Leu Thr Tyr Leu Glu His Arg Leu
                165                 170                 175
Met Pro Ile Leu Asp Gln Asn Phe Ile Glu Tyr Lys Ile Thr Val Asn
            180                 185                 190
Glu Asp Lys Pro Ile Ser Glu Ser His Val Lys Glu Leu Ile Ala Glu
                195                 200                 205
Leu Arg Trp Gln Tyr Asn Lys Phe Ala Val Ile Thr His Gly Lys Gly
            210                 215                 220
His Tyr Arg Val Val Lys Tyr Ser Ser Val Ala Asn His Ala Asp Arg
225                 230                 235                 240
Val Tyr Ala Thr Phe Lys Ser Asn Asn Lys Asn Gly Asn Val Leu Glu
                245                 250                 255
Phe Asn Leu Leu Asp Gln Arg Val Ile Trp Gln Asn Trp Tyr Ala Phe
            260                 265                 270
Thr Ser Ser Met Lys Gln Gly Asn Thr Leu Glu Ile Cys Lys Lys Leu
                275                 280                 285
Leu Phe Gln Lys Met Lys Arg Glu Ser Asn Pro Phe Lys Gly Leu Ser
            290                 295                 300
Thr Asp Arg Lys Met Asp Glu Val Ser Gln Ile Gly Ile
305                 310                 315

<210> SEQ ID NO 23
<211> LENGTH: 326
<212> TYPE: PRT
<213> ORGANISM: Rotavirus

<400> SEQUENCE: 23

Met Tyr Gly Ile Glu Tyr Thr Thr Val Leu Thr Phe Leu Ile Ser Leu
 1               5                  10                  15
Ile Leu Leu Asn Tyr Ile Leu Lys Ser Leu Thr Arg Met Met Asp Phe
                20                  25                  30
Ile Ile Tyr Arg Phe Leu Phe Ile Val Val Ile Leu Ser Pro Leu Leu
            35                  40                  45
Lys Ala Gln Asn Tyr Gly Ile Asn Leu Pro Ile Thr Gly Ser Met Asp
 50                  55                  60
Thr Ala Tyr Ala Asn Ser Thr Gln Glu Glu Thr Phe Leu Thr Ser Thr
65                  70                  75                  80
Leu Cys Leu Tyr Tyr Pro Thr Glu Ala Ala Thr Glu Ile Asn Asp Asn
                85                  90                  95
Ser Trp Lys Asp Thr Leu Ser Gln Leu Phe Leu Thr Lys Gly Trp Pro
            100                 105                 110
Thr Gly Ser Val Tyr Phe Lys Glu Tyr Thr Asp Ile Ala Ser Phe Ser
                115                 120                 125
Val Asp Pro Gln Leu Tyr Cys Asp Tyr Asn Val Val Leu Met Lys Tyr
            130                 135                 140
Asp Ala Thr Leu Gln Leu Asp Met Ser Glu Leu Ala Asp Leu Ile Leu
145                 150                 155                 160
```

```
Asn Glu Trp Leu Cys Asn Pro Met Asp Ile Thr Leu Tyr Tyr Tyr Gln
                165                 170                 175

Gln Thr Asp Glu Ala Asn Lys Trp Ile Ser Met Gly Ser Ser Cys Thr
            180                 185                 190

Ile Lys Val Cys Pro Leu Asn Thr Gln Thr Leu Gly Ile Gly Cys Leu
        195                 200                 205

Thr Thr Asp Thr Ala Thr Phe Glu Glu Val Ala Thr Ala Glu Lys Leu
210                 215                 220

Val Ile Thr Asp Val Val Asp Gly Val Asn His Lys Leu Asp Val Thr
225                 230                 235                 240

Thr Ala Thr Cys Thr Ile Arg Asn Cys Lys Lys Leu Gly Pro Arg Glu
                245                 250                 255

Asn Val Ala Val Ile Gln Val Gly Gly Ser Asp Val Leu Asp Ile Thr
            260                 265                 270

Ala Asp Pro Thr Thr Ala Pro Gln Thr Glu Arg Met Met Arg Ile Asn
        275                 280                 285

Trp Lys Lys Trp Trp Gln Val Phe Tyr Thr Val Val Asp Tyr Val Asn
290                 295                 300

Gln Ile Ile Gln Ala Met Ser Lys Arg Ser Arg Ser Leu Asn Ser Ala
305                 310                 315                 320

Ala Phe Tyr Tyr Arg Ile
                325

<210> SEQ ID NO 24
<211> LENGTH: 175
<212> TYPE: PRT
<213> ORGANISM: Rotavirus

<400> SEQUENCE: 24

Met Glu Lys Leu Thr Asp Leu Asn Tyr Thr Leu Ser Val Val Thr Leu
1               5                   10                  15

Met Asn Asp Thr Leu His Thr Ile Met Glu Asp Pro Gly Met Ala Tyr
            20                  25                  30

Phe Pro Tyr Ile Ala Ser Val Leu Thr Val Leu Phe Thr Leu His Lys
        35                  40                  45

Ala Ser Val Pro Thr Met Lys Ile Ala Leu Lys Thr Ser Lys Cys Ser
    50                  55                  60

Tyr Lys Val Ile Lys Tyr Cys Ile Val Ser Ile Phe Asn Thr Leu Leu
65                  70                  75                  80

Lys Leu Ala Gly Tyr Lys Glu Gln Ile Thr Thr Lys Asp Glu Ile Glu
                85                  90                  95

Arg Gln Met Asp Arg Val Val Lys Glu Met Arg Arg Gln Leu Glu Met
            100                 105                 110

Ile Asp Lys Leu Thr Thr Arg Glu Ile Glu Gln Val Glu Leu Leu Lys
        115                 120                 125

Arg Ile His Asp Met Leu Ile Ile Lys Pro Val Asp Lys Ile Asp Met
    130                 135                 140

Ser Gln Glu Phe Asn Gln Lys Tyr Phe Lys Thr Leu Asn Asp Trp Ala
145                 150                 155                 160

Glu Gly Glu Asn Pro Tyr Glu Pro Lys Glu Val Thr Ala Ser Leu
                165                 170                 175

<210> SEQ ID NO 25
<211> LENGTH: 196
<212> TYPE: PRT
<213> ORGANISM: Rotavirus
```

```
<400> SEQUENCE: 25

Met Ser Leu Ser Ile Asp Val Thr Ser Leu Pro Ile Ser Ser Ser
1               5                   10                  15

Ile Tyr Lys His Glu Ser Ser Thr Thr Ser Thr Leu Ser Gly Lys
                20                  25                  30

Ser Ile Gly Arg Ser Glu Gln Tyr Val Ser Pro Asp Ala Glu Ala Phe
            35                  40                  45

Asn Lys Tyr Met Leu Ser Lys Ser Pro Glu Asp Ile Gly Pro Ser Asp
        50                  55                  60

Ser Asn Asp Pro Leu Thr Ser Phe Ser Ile Arg Ser Asn Ala Val Lys
65                  70                  75                  80

Thr Asn Ala Asp Ala Gly Val Ser Met Asp Ser Ser Thr Gln Ser Arg
                85                  90                  95

Pro Ser Ser Asn Val Gly Cys Asp Gln Val Asp Phe Ser Leu Ser Lys
            100                 105                 110

Gly Ile Lys Val Asn Ala Asn Leu Asp Ser Ser Ile Ser Val Ser Thr
        115                 120                 125

Val Ser Lys Lys Glu Lys Ser Lys Ser Asp His Lys Asn Arg Lys His
130                 135                 140

Tyr Pro Arg Ile Glu Ala Asp Ser Asp Ser Asp Glu Tyr Val Leu Asp
145                 150                 155                 160

Asp Ser Asp Ser Asp Asp Gly Lys Cys Lys Asn Cys Lys Tyr Lys Lys
                165                 170                 175

Lys Tyr Phe Ala Leu Arg Met Arg Met Lys Gln Val Ala Met Gln Leu
            180                 185                 190

Ile Glu Asp Leu
        195

<210> SEQ ID NO 26
<211> LENGTH: 322
<212> TYPE: PRT
<213> ORGANISM: Rotavirus

<400> SEQUENCE: 26

Met Tyr Gly Ile Glu Tyr Thr Thr Ile Leu Ile Phe Leu Ile Ser Ile
1               5                   10                  15

Ile Leu Leu Asn Tyr Ile Leu Lys Ser Val Thr Arg Ile Met Asp Tyr
                20                  25                  30

Ile Ile Tyr Arg Phe Leu Leu Ile Thr Val Phe Ala Leu Thr Arg Ala
            35                  40                  45

Gln Asn Tyr Gln Leu Pro Ile Thr Gly Ser Met Asp Ala Val Tyr Thr
        50                  55                  60

Asn Ser Thr Gln Glu Glu Val Phe Leu Thr Ser Thr Leu Cys Leu Tyr
65                  70                  75                  80

Tyr Pro Thr Glu Ala Ser Thr Gln Ile Asn Asp Gly Asp Trp Lys Asp
                85                  90                  95

Ser Leu Ser Gln Met Phe Leu Thr Lys Gly Trp Pro Thr Gly Ser Val
            100                 105                 110

Tyr Phe Lys Glu Tyr Ser Ser Ile Val Asp Phe Ser Val Asp Pro Gln
        115                 120                 125

Leu Tyr Cys Asp Tyr Asn Leu Val Leu Met Lys Tyr Asp Gln Ser Leu
        130                 135                 140

Glu Leu Asp Met Ser Glu Leu Ala Asp Leu Ile Leu Asn Glu Trp Leu
145                 150                 155                 160
```

```
Cys Asn Pro Met Asp Val Thr Leu Tyr Tyr Gln Gln Ser Gly Glu
            165                 170                 175

Ser Asn Lys Trp Ile Ser Met Gly Ser Ser Cys Thr Val Lys Val Cys
        180                 185                 190

Pro Leu Asn Thr Gln Thr Leu Gly Ile Gly Cys Gln Thr Thr Asn Val
            195                 200                 205

Asp Ser Phe Glu Met Ile Ala Glu Asn Glu Lys Leu Ala Ile Val Asp
            210                 215                 220

Val Val Asp Gly Ile Asn His Lys Ile Asn Leu Thr Thr Thr Cys
225                 230                 235                 240

Thr Ile Arg Asn Cys Lys Lys Leu Gly Pro Arg Glu Asn Val Ala Val
                245                 250                 255

Ile Gln Val Gly Gly Ser Asn Val Leu Asp Ile Thr Ala Asp Pro Thr
            260                 265                 270

Thr Asn Pro Gln Thr Glu Arg Met Met Arg Val Asn Trp Lys Lys Trp
            275                 280                 285

Trp Gln Val Phe Tyr Thr Ile Val Asp Tyr Ile Asn Gln Ile Val Gln
    290                 295                 300

Val Met Ser Lys Arg Ser Arg Ser Leu Asn Ser Ala Ala Phe Tyr Tyr
305                 310                 315                 320

Arg Val
```

<210> SEQ ID NO 27
<211> LENGTH: 326
<212> TYPE: PRT
<213> ORGANISM: Rotavirus

<400> SEQUENCE: 27

```
Met Tyr Gly Ile Glu Tyr Thr Thr Ile Leu Thr Ile Leu Ile Ser Ile
1               5                   10                  15

Ile Leu Leu Asn Tyr Ile Leu Lys Thr Ile Thr Asn Thr Met Asp Tyr
            20                  25                  30

Ile Ile Phe Arg Phe Leu Leu Leu Ile Ala Leu Ile Ser Pro Phe Val
        35                  40                  45

Arg Thr Gln Asn Tyr Gly Met Tyr Leu Pro Ile Thr Gly Ser Leu Asp
    50                  55                  60

Ala Val Tyr Thr Asn Ser Thr Ser Gly Glu Pro Phe Leu Thr Ser Thr
65                  70                  75                  80

Leu Cys Leu Tyr Tyr Pro Ala Glu Ala Lys Asn Glu Ile Ser Asp Asp
                85                  90                  95

Glu Trp Glu Asn Thr Leu Ser Gln Leu Phe Leu Thr Lys Gly Trp Pro
            100                 105                 110

Ile Gly Ser Val Tyr Phe Lys Asp Tyr Asn Asp Ile Asn Thr Phe Ser
        115                 120                 125

Val Asn Pro Gln Leu Tyr Cys Asp Tyr Asn Val Val Leu Met Arg Tyr
    130                 135                 140

Asp Asn Thr Ser Glu Leu Asp Ala Ser Glu Leu Ala Asp Leu Ile Leu
145                 150                 155                 160

Asn Glu Trp Leu Cys Asn Pro Met Asp Ile Ser Leu Tyr Tyr Tyr Gln
                165                 170                 175

Gln Ser Ser Glu Ser Asn Lys Trp Ile Ser Met Gly Thr Asp Cys Thr
            180                 185                 190

Val Lys Val Cys Pro Leu Asn Thr Gln Thr Leu Gly Ile Gly Cys Lys
        195                 200                 205
```

```
Thr Thr Asp Val Asn Thr Phe Glu Ile Val Ala Ser Ser Glu Lys Leu
    210                 215                 220

Val Ile Thr Asp Val Val Asn Gly Val Asn His Lys Ile Asn Ile Ser
225                 230                 235                 240

Ile Asn Thr Cys Thr Ile Arg Asn Cys Asn Lys Leu Gly Pro Arg Glu
                245                 250                 255

Asn Val Ala Ile Ile Gln Val Gly Gly Pro Asn Ala Leu Asp Ile Thr
            260                 265                 270

Ala Asp Pro Thr Thr Val Pro Gln Val Gln Arg Ile Met Arg Ile Asn
        275                 280                 285

Trp Lys Lys Trp Trp Gln Val Phe Tyr Thr Val Val Asp Tyr Ile Asn
    290                 295                 300

Gln Val Ile Gln Val Met Ser Lys Arg Ser Arg Ser Leu Asp Ala Ala
305                 310                 315                 320

Ala Phe Tyr Tyr Arg Ile
                325

<210> SEQ ID NO 28
<211> LENGTH: 326
<212> TYPE: PRT
<213> ORGANISM: Rotavirus

<400> SEQUENCE: 28

Met Tyr Gly Ile Glu Tyr Thr Thr Val Leu Phe Tyr Leu Ile Ser Phe
1               5                   10                  15

Val Leu Val Ser Tyr Ile Leu Lys Thr Ile Lys Ile Met Asp Tyr
            20                  25                  30

Ile Ile Tyr Arg Ile Thr Phe Val Ile Val Leu Ser Val Leu Ser
            35                  40                  45

Asn Ala Gln Asn Tyr Gly Ile Asn Leu Pro Ile Thr Gly Ser Met Asp
    50                  55                  60

Thr Ala Tyr Ala Asn Ser Thr Gln Asp Asn Asn Phe Leu Phe Ser Thr
65                  70                  75                  80

Leu Cys Leu Tyr Tyr Pro Ser Glu Ala Pro Thr Gln Ile Ser Asp Thr
                85                  90                  95

Glu Trp Lys Asp Thr Leu Ser Gln Leu Phe Leu Thr Lys Gly Trp Pro
            100                 105                 110

Thr Gly Ser Val Tyr Phe Asn Glu Tyr Ser Asn Val Leu Glu Phe Ser
        115                 120                 125

Ile Asp Pro Lys Leu Tyr Cys Asp Tyr Asn Val Val Leu Ile Arg Phe
    130                 135                 140

Val Ser Gly Glu Glu Leu Asp Ile Ser Glu Leu Ala Asp Leu Ile Leu
145                 150                 155                 160

Asn Glu Trp Leu Cys Asn Pro Met Asp Ile Thr Leu Tyr Tyr Tyr Gln
                165                 170                 175

Gln Thr Gly Glu Ala Asn Lys Trp Ile Ser Met Gly Ser Ser Cys Thr
            180                 185                 190

Val Lys Val Cys Pro Leu Asn Thr Gln Thr Leu Gly Ile Gly Cys Gln
        195                 200                 205

Thr Thr Asn Thr Ala Thr Phe Glu Thr Val Ala Asp Ser Glu Lys Leu
    210                 215                 220

Ala Ile Ile Asp Val Val Asp Ser Val Asn His Lys Leu Asn Ile Thr
225                 230                 235                 240

Ser Thr Thr Cys Thr Ile Arg Asn Cys Asn Lys Leu Gly Pro Arg Glu
```

```
                    245                 250                 255
Asn Val Ala Ile Ile Gln Val Gly Gly Ser Asn Ile Leu Asp Ile Thr
            260                 265                 270
Ala Asp Pro Thr Thr Ser Pro Gln Thr Glu Arg Met Met Arg Val Asn
        275                 280                 285
Trp Lys Lys Trp Trp Gln Val Phe Tyr Thr Val Val Asp Tyr Ile Asp
    290                 295                 300
Gln Ile Val Gln Val Met Ser Lys Arg Ser Arg Ser Leu Asp Leu Ser
305                 310                 315                 320
Ser Phe Tyr Tyr Arg Val
                325

<210> SEQ ID NO 29
<211> LENGTH: 27
<212> TYPE: DNA
<213> ORGANISM: Artificial Sequence
<220> FEATURE:
<223> OTHER INFORMATION: Primer

<400> SEQUENCE: 29
ggctattaaa gctgtacaat ggggaag                                        27

<210> SEQ ID NO 30
<211> LENGTH: 30
<212> TYPE: DNA
<213> ORGANISM: Artificial Sequence
<220> FEATURE:
<223> OTHER INFORMATION: Primer

<400> SEQUENCE: 30
ctaagcgttc taatcttgaa agaagtttgc                                     30

<210> SEQ ID NO 31
<211> LENGTH: 27
<212> TYPE: DNA
<213> ORGANISM: Artificial Sequence
<220> FEATURE:
<223> OTHER INFORMATION: Primer

<400> SEQUENCE: 31
ggctattaaa ggctcaatgg cgtacag                                        27

<210> SEQ ID NO 32
<211> LENGTH: 26
<212> TYPE: DNA
<213> ORGANISM: Artificial Sequence
<220> FEATURE:
<223> OTHER INFORMATION: Primer

<400> SEQUENCE: 32
ggtcatatct ccacaatggg gttggc                                         26

<210> SEQ ID NO 33
<211> LENGTH: 25
<212> TYPE: DNA
<213> ORGANISM: Artificial Sequence
<220> FEATURE:
<223> OTHER INFORMATION: Primer

<400> SEQUENCE: 33
ggctattaaa gcagtacgag tagtg                                          25

<210> SEQ ID NO 34
```

```
<211> LENGTH: 21
<212> TYPE: DNA
<213> ORGANISM: Artificial Sequence
<220> FEATURE:
<223> OTHER INFORMATION: Primer

<400> SEQUENCE: 34
ggtcacatca tgactagtgt g                                         21

<210> SEQ ID NO 35
<211> LENGTH: 21
<212> TYPE: DNA
<213> ORGANISM: Artificial Sequence
<220> FEATURE:
<223> OTHER INFORMATION: Primer

<400> SEQUENCE: 35
ggctataaaa tggcttcgct c                                         21

<210> SEQ ID NO 36
<211> LENGTH: 22
<212> TYPE: DNA
<213> ORGANISM: Artificial Sequence
<220> FEATURE:
<223> OTHER INFORMATION: Primer

<400> SEQUENCE: 36
ggtcacatcc tctggaaatt gc                                        22

<210> SEQ ID NO 37
<211> LENGTH: 29
<212> TYPE: DNA
<213> ORGANISM: Artificial Sequence
<220> FEATURE:
<223> OTHER INFORMATION: Primer

<400> SEQUENCE: 37
ggcttttttt tgaaatgtct tgtgttagc                                 29

<210> SEQ ID NO 38
<211> LENGTH: 24
<212> TYPE: DNA
<213> ORGANISM: Artificial Sequence
<220> FEATURE:
<223> OTHER INFORMATION: Primer

<400> SEQUENCE: 38
ggtcacagtt tttgctggct aggc                                      24

<210> SEQ ID NO 39
<211> LENGTH: 26
<212> TYPE: DNA
<213> ORGANISM: Artificial Sequence
<220> FEATURE:
<223> OTHER INFORMATION: Primer

<400> SEQUENCE: 39
ggcttttaaa cgaagtcttc aacatg                                    26

<210> SEQ ID NO 40
<211> LENGTH: 25
<212> TYPE: DNA
<213> ORGANISM: Artificial Sequence
<220> FEATURE:
<223> OTHER INFORMATION: Primer

<400> SEQUENCE: 40
```
ggtcacatcc tctcactata ccatc                                          25

<210> SEQ ID NO 41
<211> LENGTH: 25
<212> TYPE: DNA
<213> ORGANISM: Artificial Sequence
<220> FEATURE:
<223> OTHER INFORMATION: Primer

<400> SEQUENCE: 41
ggcatttaat gcttttcagt ggttg                                          25

<210> SEQ ID NO 42
<211> LENGTH: 22
<212> TYPE: DNA
<213> ORGANISM: Artificial Sequence
<220> FEATURE:
<223> OTHER INFORMATION: Primer

<400> SEQUENCE: 42
ggtcacataa cgcccctata gc                                             22

<210> SEQ ID NO 43
<211> LENGTH: 29
<212> TYPE: DNA
<213> ORGANISM: Artificial Sequence
<220> FEATURE:
<223> OTHER INFORMATION: Primer

<400> SEQUENCE: 43
ggcttttaaa gcgtctcagt cgccgttcg                                      29

<210> SEQ ID NO 44
<211> LENGTH: 23
<212> TYPE: DNA
<213> ORGANISM: Artificial Sequence
<220> FEATURE:
<223> OTHER INFORMATION: Primer

<400> SEQUENCE: 44
ggtcacataa gcgctttcta ttc                                            23

<210> SEQ ID NO 45
<211> LENGTH: 24
<212> TYPE: DNA
<213> ORGANISM: Artificial Sequence
<220> FEATURE:
<223> OTHER INFORMATION: Primer

<400> SEQUENCE: 45
ggctttaaaa gcgagaattt ccgt                                           24

<210> SEQ ID NO 46
<211> LENGTH: 22
<212> TYPE: DNA
<213> ORGANISM: Artificial Sequence
<220> FEATURE:
<223> OTHER INFORMATION: Primer

<400> SEQUENCE: 46
ggtcacatca tacatttcta ac                                             22

<210> SEQ ID NO 47
<211> LENGTH: 27
<212> TYPE: DNA

```
<213> ORGANISM: Artificial Sequence
<220> FEATURE:
<223> OTHER INFORMATION: Primer

<400> SEQUENCE: 47
ggtcacatcg aacaattcta atctaag                                          27

<210> SEQ ID NO 48
<211> LENGTH: 28
<212> TYPE: DNA
<213> ORGANISM: Artificial Sequence
<220> FEATURE:
<223> OTHER INFORMATION: Primer

<400> SEQUENCE: 48
ggtcacatcg aacaattctg accaaatc                                         28

<210> SEQ ID NO 49
<211> LENGTH: 27
<212> TYPE: DNA
<213> ORGANISM: Artificial Sequence
<220> FEATURE:
<223> OTHER INFORMATION: Primer

<400> SEQUENCE: 49
ggtcacatca tacatttcta ttttagg                                          27

<210> SEQ ID NO 50
<211> LENGTH: 27
<212> TYPE: DNA
<213> ORGANISM: Artificial Sequence
<220> FEATURE:
<223> OTHER INFORMATION: Primer

<400> SEQUENCE: 50 ggcttttttaa aagttctgtt ccgagag                                         27

<210> SEQ ID NO 51
<211> LENGTH: 23
<212> TYPE: DNA
<213> ORGANISM: Artificial Sequence
<220> FEATURE:
<223> OTHER INFORMATION: Primer

<400> SEQUENCE: 51
ggtcacatta agaccgttcc ttc                                              23

<210> SEQ ID NO 52
<211> LENGTH: 24
<212> TYPE: DNA
<213> ORGANISM: Artificial Sequence
<220> FEATURE:
<223> OTHER INFORMATION: Primer

<400> SEQUENCE: 52
ggcttttaaa gcgctacagt gatg                                             24

<210> SEQ ID NO 53
<211> LENGTH: 24
<212> TYPE: DNA
<213> ORGANISM: Artificial Sequence
<220> FEATURE:
<223> OTHER INFORMATION: Primer

<400> SEQUENCE: 53
ggtcacataa ctggagtggg gagc                                             24
```

<210> SEQ ID NO 54
<211> LENGTH: 33
<212> TYPE: DNA
<213> ORGANISM: Artificial Sequence
<220> FEATURE:
<223> OTHER INFORMATION: Primer

<400> SEQUENCE: 54
cccaagcttg tgtggcattc tctataacat cgc                               33

<210> SEQ ID NO 55
<211> LENGTH: 33
<212> TYPE: DNA
<213> ORGANISM: Artificial Sequence
<220> FEATURE:
<223> OTHER INFORMATION: Primer

<400> SEQUENCE: 55
cccggatccg gctcatggat aagcttattc tgc                               33

<210> SEQ ID NO 56
<211> LENGTH: 33
<212> TYPE: DNA
<213> ORGANISM: Artificial Sequence
<220> FEATURE:
<223> OTHER INFORMATION: Primer

<400> SEQUENCE: 56
cccaagcttc aaatctgctt ctagcggctt acc                               33

<210> SEQ ID NO 57
<211> LENGTH: 33
<212> TYPE: DNA
<213> ORGANISM: Artificial Sequence
<220> FEATURE:
<223> OTHER INFORMATION: Primer

<400> SEQUENCE: 57
cccggatcct aaaggaaaga taccagctgt cac                               33

<210> SEQ ID NO 58
<211> LENGTH: 33
<212> TYPE: DNA
<213> ORGANISM: Artificial Sequence
<220> FEATURE:
<223> OTHER INFORMATION: Primer

<400> SEQUENCE: 58
cccaagcttc cttttgagat agcactttct ctg                               33

<210> SEQ ID NO 59
<211> LENGTH: 33
<212> TYPE: DNA
<213> ORGANISM: Artificial Sequence
<220> FEATURE:
<223> OTHER INFORMATION: Primer

<400> SEQUENCE: 59
cccggatcca ccacaacaat ttgattttag agc                               33

<210> SEQ ID NO 60
<211> LENGTH: 24
<212> TYPE: DNA
<213> ORGANISM: Artificial Sequence
<220> FEATURE:

```
<223> OTHER INFORMATION: Primer

<400> SEQUENCE: 60 cttcttttg atgttcttcc ttag                                              24

<210> SEQ ID NO 61
<211> LENGTH: 24
<212> TYPE: DNA
<213> ORGANISM: Artificial Sequence
<220> FEATURE:
<223> OTHER INFORMATION: Primer

<400> SEQUENCE: 61
tgtagcgaat tatgactggg ttcc                                             24

<210> SEQ ID NO 62
<211> LENGTH: 33
<212> TYPE: DNA
<213> ORGANISM: Artificial Sequence
<220> FEATURE:
<223> OTHER INFORMATION: Primer

<400> SEQUENCE: 62
cccaagctta agaaatgcat tctcgtaact gtc                                   33

<210> SEQ ID NO 63
<211> LENGTH: 33
<212> TYPE: DNA
<213> ORGANISM: Artificial Sequence
<220> FEATURE:
<223> OTHER INFORMATION: Primer

<400> SEQUENCE: 63
cccggatccg tcaatctaga atgtttattc cac                                   33

<210> SEQ ID NO 64
<211> LENGTH: 24
<212> TYPE: DNA
<213> ORGANISM: Artificial Sequence
<220> FEATURE:
<223> OTHER INFORMATION: Primer

<400> SEQUENCE: 64
ttgaatctca acagctgcaa ttcc                                             24

<210> SEQ ID NO 65
<211> LENGTH: 24
<212> TYPE: DNA
<213> ORGANISM: Artificial Sequence
<220> FEATURE:
<223> OTHER INFORMATION: Primer

<400> SEQUENCE: 65
aaacgttagt ggagttctag cgac                                             24

<210> SEQ ID NO 66
<211> LENGTH: 33
<212> TYPE: DNA
<213> ORGANISM: Artificial Sequence
<220> FEATURE:
<223> OTHER INFORMATION: Primer

<400> SEQUENCE: 66
cccaagcttc ccagttaact ggagcataac ctg                                   33
```

```
<210> SEQ ID NO 67
<211> LENGTH: 33
<212> TYPE: DNA
<213> ORGANISM: Artificial Sequence
<220> FEATURE:
<223> OTHER INFORMATION: Primer

<400> SEQUENCE: 67
cccggatcca actgactctc cggtcatctc agc                         33

<210> SEQ ID NO 68
<211> LENGTH: 24
<212> TYPE: DNA
<213> ORGANISM: Artificial Sequence
<220> FEATURE:
<223> OTHER INFORMATION: Primer

<400> SEQUENCE: 68
gaacgttgtt ggttgataag gacc                                   24

<210> SEQ ID NO 69
<211> LENGTH: 24
<212> TYPE: DNA
<213> ORGANISM: Artificial Sequence
<220> FEATURE:
<223> OTHER INFORMATION: Primer

<400> SEQUENCE: 69
agtctttgaa gcgggaacag atgg                                   24

<210> SEQ ID NO 70
<211> LENGTH: 33
<212> TYPE: DNA
<213> ORGANISM: Artificial Sequence
<220> FEATURE:
<223> OTHER INFORMATION: Primer

<400> SEQUENCE: 70
cccaagctta ttgacaacac tcaatgcacc acc                         33

<210> SEQ ID NO 71
<211> LENGTH: 33
<212> TYPE: DNA
<213> ORGANISM: Artificial Sequence
<220> FEATURE:
<223> OTHER INFORMATION: Primer

<400> SEQUENCE: 71
cccggatccg aattagatca cttgccgtta tgc                         33

<210> SEQ ID NO 72
<211> LENGTH: 24
<212> TYPE: DNA
<213> ORGANISM: Artificial Sequence
<220> FEATURE:
<223> OTHER INFORMATION: Primer

<400> SEQUENCE: 72
gatgcaccac tgacaaacat gagc                                   24

<210> SEQ ID NO 73
<211> LENGTH: 24
<212> TYPE: DNA
<213> ORGANISM: Artificial Sequence
<220> FEATURE:
<223> OTHER INFORMATION: Primer
```

```
<400> SEQUENCE: 73
gatactggaa accgaggctc ttcc                                              24

<210> SEQ ID NO 74
<211> LENGTH: 33
<212> TYPE: DNA
<213> ORGANISM: Artificial Sequence
<220> FEATURE:
<223> OTHER INFORMATION: Primer

<400> SEQUENCE: 74
cccaagcttt cggcagatta ccaattcctc cag                                    33

<210> SEQ ID NO 75
<211> LENGTH: 33
<212> TYPE: DNA
<213> ORGANISM: Artificial Sequence
<220> FEATURE:
<223> OTHER INFORMATION: Primer

<400> SEQUENCE: 75
cccggatccc agcgtgtatt tacagtggct tcc                                    33

<210> SEQ ID NO 76
<211> LENGTH: 24
<212> TYPE: DNA
<213> ORGANISM: Artificial Sequence
<220> FEATURE:
<223> OTHER INFORMATION: Primer

<400> SEQUENCE: 76
acgggccgtt tcgacatagt tagc                                              24

<210> SEQ ID NO 77
<211> LENGTH: 24
<212> TYPE: DNA
<213> ORGANISM: Artificial Sequence
<220> FEATURE:
<223> OTHER INFORMATION: Primer

<400> SEQUENCE: 77
agaatacgcg ataccagttg gacc                                              24

<210> SEQ ID NO 78
<211> LENGTH: 33
<212> TYPE: DNA
<213> ORGANISM: Artificial Sequence
<220> FEATURE:
<223> OTHER INFORMATION: Primer

<400> SEQUENCE: 78
cccaagcttt caagagtaga agttgcagca acc                                    33

<210> SEQ ID NO 79
<211> LENGTH: 33
<212> TYPE: DNA
<213> ORGANISM: Artificial Sequence
<220> FEATURE:
<223> OTHER INFORMATION: Primer

<400> SEQUENCE: 79
cccggatcca aaggattatt gcagcaatgc aac                                    33

<210> SEQ ID NO 80
<211> LENGTH: 24
```

```
<212> TYPE: DNA
<213> ORGANISM: Artificial Sequence
<220> FEATURE:
<223> OTHER INFORMATION: Primer

<400> SEQUENCE: 80
actctttact ctagtatata cctc                                              24

<210> SEQ ID NO 81
<211> LENGTH: 24
<212> TYPE: DNA
<213> ORGANISM: Artificial Sequence
<220> FEATURE:
<223> OTHER INFORMATION: Primer

<400> SEQUENCE: 81
aaatcagaca ttgaacaaca gctg                                              24

<210> SEQ ID NO 82
<211> LENGTH: 27
<212> TYPE: DNA
<213> ORGANISM: Artificial Sequence
<220> FEATURE:
<223> OTHER INFORMATION: Primer

<400> SEQUENCE: 82
tagctacagt tcgagagtca gtcatcc                                           27

<210> SEQ ID NO 83
<211> LENGTH: 27
<212> TYPE: DNA
<213> ORGANISM: Artificial Sequence
<220> FEATURE:
<223> OTHER INFORMATION: Primer

<400> SEQUENCE: 83
caatagaatg gtatctaaga tcgatgg                                           27

<210> SEQ ID NO 84
<211> LENGTH: 33
<212> TYPE: DNA
<213> ORGANISM: Artificial Sequence
<220> FEATURE:
<223> OTHER INFORMATION: Primer

<400> SEQUENCE: 84
cccaagcttg aattgtggcg gtggtgcgat acc                                    33

<210> SEQ ID NO 85
<211> LENGTH: 33
<212> TYPE: DNA
<213> ORGANISM: Artificial Sequence
<220> FEATURE:
<223> OTHER INFORMATION: Primer

<400> SEQUENCE: 85
cccggatcca aaatgaagcg ggaaagtaat ccg                                    33

<210> SEQ ID NO 86
<211> LENGTH: 24
<212> TYPE: DNA
<213> ORGANISM: Artificial Sequence
<220> FEATURE:
<223> OTHER INFORMATION: Primer

<400> SEQUENCE: 86
```
cgcttcacaa attaacaccg ccac                                            24

<210> SEQ ID NO 87
<211> LENGTH: 24
<212> TYPE: DNA
<213> ORGANISM: Artificial Sequence
<220> FEATURE:
<223> OTHER INFORMATION: Primer

<400> SEQUENCE: 87
gaactggtat gcgtttacat cctc                                            24

<210> SEQ ID NO 88
<211> LENGTH: 33
<212> TYPE: DNA
<213> ORGANISM: Artificial Sequence
<220> FEATURE:
<223> OTHER INFORMATION: Primer

<400> SEQUENCE: 88
cccaagcttc gtatgcagtg tccattgaac cag                                  33

<210> SEQ ID NO 89
<211> LENGTH: 33
<212> TYPE: DNA
<213> ORGANISM: Artificial Sequence
<220> FEATURE:
<223> OTHER INFORMATION: Primer

<400> SEQUENCE: 89
cccggatccg cattaattgg aagaaatggt ggc                                  33

<210> SEQ ID NO 90
<211> LENGTH: 24
<212> TYPE: DNA
<213> ORGANISM: Artificial Sequence
<220> FEATURE:
<223> OTHER INFORMATION: Primer

<400> SEQUENCE: 90
tatttctgtt gcagcttcag ttgg                                            24

<210> SEQ ID NO 91
<211> LENGTH: 24
<212> TYPE: DNA
<213> ORGANISM: Artificial Sequence
<220> FEATURE:
<223> OTHER INFORMATION: Primer

<400> SEQUENCE: 91
gttggaggtt ctgatgttct cgac                                            24

<210> SEQ ID NO 92
<211> LENGTH: 33
<212> TYPE: DNA
<213> ORGANISM: Artificial Sequence
<220> FEATURE:
<223> OTHER INFORMATION: Primer

<400> SEQUENCE: 92
cccaagctta cctgaaaatt atgtagtcca tcg                                  33

<210> SEQ ID NO 93
<211> LENGTH: 33
<212> TYPE: DNA
<213> ORGANISM: Artificial Sequence

```
<220> FEATURE:
<223> OTHER INFORMATION: Primer

<400> SEQUENCE: 93
cccggatccc ccacaagttc aaagaatcat gcg                              33

<210> SEQ ID NO 94
<211> LENGTH: 24
<212> TYPE: DNA
<213> ORGANISM: Artificial Sequence
<220> FEATURE:
<223> OTHER INFORMATION: Primer

<400> SEQUENCE: 94
agcgtctagt gaccccgtta ttgg                                        24

<210> SEQ ID NO 95
<211> LENGTH: 24
<212> TYPE: DNA
<213> ORGANISM: Artificial Sequence
<220> FEATURE:
<223> OTHER INFORMATION: Primer

<400> SEQUENCE: 95
aattcaagtt ggtggaccga acgc                                        24

<210> SEQ ID NO 96
<211> LENGTH: 33
<212> TYPE: DNA
<213> ORGANISM: Artificial Sequence
<220> FEATURE:
<223> OTHER INFORMATION: Primer

<400> SEQUENCE: 96
cccaagcttt gtagtccatt attcgagtca ctg                              33

<210> SEQ ID NO 97
<211> LENGTH: 33
<212> TYPE: DNA
<213> ORGANISM: Artificial Sequence
<220> FEATURE:
<223> OTHER INFORMATION: Primer

<400> SEQUENCE: 97
cccggatccc aaactgagag aatgatgaga gtg                              33

<210> SEQ ID NO 98
<211> LENGTH: 24
<212> TYPE: DNA
<213> ORGANISM: Artificial Sequence
<220> FEATURE:
<223> OTHER INFORMATION: Primer

<400> SEQUENCE: 98
agcgtccatt gatcctgtta ttgg                                        24

<210> SEQ ID NO 99
<211> LENGTH: 24
<212> TYPE: DNA
<213> ORGANISM: Artificial Sequence
<220> FEATURE:
<223> OTHER INFORMATION: Primer

<400> SEQUENCE: 99
tgtagctgta atacaagttg gtgg                                        24
```

<210> SEQ ID NO 100
<211> LENGTH: 33
<212> TYPE: DNA
<213> ORGANISM: Artificial Sequence
<220> FEATURE:
<223> OTHER INFORMATION: Primer

<400> SEQUENCE: 100
cccaagcttg tatccataga tccagtaatt ggc                33

<210> SEQ ID NO 101
<211> LENGTH: 33
<212> TYPE: DNA
<213> ORGANISM: Artificial Sequence
<220> FEATURE:
<223> OTHER INFORMATION: Primer

<400> SEQUENCE: 101
cccggatcca atggtggcaa gtattctaca ctg                33

<210> SEQ ID NO 102
<211> LENGTH: 24
<212> TYPE: DNA
<213> ORGANISM: Artificial Sequence
<220> FEATURE:
<223> OTHER INFORMATION: Primer

<400> SEQUENCE: 102
aatttgagtt ggagcttctg atgg                          24

<210> SEQ ID NO 103
<211> LENGTH: 24
<212> TYPE: DNA
<213> ORGANISM: Artificial Sequence
<220> FEATURE:
<223> OTHER INFORMATION: Primer

<400> SEQUENCE: 103
aacagctgat cccacaactt ctcc                          24

<210> SEQ ID NO 104
<211> LENGTH: 28
<212> TYPE: DNA
<213> ORGANISM: Artificial Sequence
<220> FEATURE:
<223> OTHER INFORMATION: Primer

<400> SEQUENCE: 104
gtacagttag gacagaagca atgtatgg                      28

<210> SEQ ID NO 105
<211> LENGTH: 28
<212> TYPE: DNA
<213> ORGANISM: Artificial Sequence
<220> FEATURE:
<223> OTHER INFORMATION: Primer

<400> SEQUENCE: 105
atcggacctg atgactggtt gagaagcc                      28

<210> SEQ ID NO 106
<211> LENGTH: 33
<212> TYPE: DNA
<213> ORGANISM: Artificial Sequence
<220> FEATURE:
<223> OTHER INFORMATION: Primer -continued

<400> SEQUENCE: 106
cccaagcttt gaaacgtact gttcactcct acc                      33

<210> SEQ ID NO 107
<211> LENGTH: 33
<212> TYPE: DNA
<213> ORGANISM: Artificial Sequence
<220> FEATURE:
<223> OTHER INFORMATION: Primer

<400> SEQUENCE: 107
cccggatcct tgaagcagat tccgattcag acg                      33

<210> SEQ ID NO 108
<211> LENGTH: 33
<212> TYPE: DNA
<213> ORGANISM: Artificial Sequence
<220> FEATURE:
<223> OTHER INFORMATION: Primer

<400> SEQUENCE: 108
cccaagcttg tcgtttgaag cagaatcaga tgg                      33

<210> SEQ ID NO 109
<211> LENGTH: 33
<212> TYPE: DNA
<213> ORGANISM: Artificial Sequence
<220> FEATURE:
<223> OTHER INFORMATION: Primer

<400> SEQUENCE: 109
cccggatccg tatcaacagt ttccaagaag gag                      33

<210> SEQ ID NO 110
<211> LENGTH: 21
<212> TYPE: DNA
<213> ORGANISM: Artificial Sequence
<220> FEATURE:
<223> OTHER INFORMATION: Primer

<400> SEQUENCE: 110
gctgatatag aaggtggaaa g                                   21

<210> SEQ ID NO 111
<211> LENGTH: 21
<212> TYPE: DNA
<213> ORGANISM: Artificial Sequence
<220> FEATURE:
<223> OTHER INFORMATION: Primer

<400> SEQUENCE: 111
ggtcacatca tgactagtgt g                                   21

<210> SEQ ID NO 112
<211> LENGTH: 19
<212> TYPE: DNA
<213> ORGANISM: Artificial Sequence
<220> FEATURE:
<223> OTHER INFORMATION: Primer

<400> SEQUENCE: 112
gagcaccata gatgcagct                                      19

<210> SEQ ID NO 113

```
<211> LENGTH: 20
<212> TYPE: DNA
<213> ORGANISM: Artificial Sequence
<220> FEATURE:
<223> OTHER INFORMATION: Primer

<400> SEQUENCE: 113
ctgacagatg aagaaacatc                                                20

<210> SEQ ID NO 114
<211> LENGTH: 19
<212> TYPE: DNA
<213> ORGANISM: Artificial Sequence
<220> FEATURE:
<223> OTHER INFORMATION: Primer

<400> SEQUENCE: 114
gagcaccata gatgcagct                                                 19

<210> SEQ ID NO 115
<211> LENGTH: 20
<212> TYPE: DNA
<213> ORGANISM: Artificial Sequence
<220> FEATURE:
<223> OTHER INFORMATION: Primer

<400> SEQUENCE: 115
gagtcagtta ctagatctgc                                                20

<210> SEQ ID NO 116
<211> LENGTH: 29
<212> TYPE: DNA
<213> ORGANISM: Artificial Sequence
<220> FEATURE:
<223> OTHER INFORMATION: Primer

<400> SEQUENCE: 116 ggctttttttt tgaaatgtct tgtgttagc                                     29

<210> SEQ ID NO 117
<211> LENGTH: 20
<212> TYPE: DNA
<213> ORGANISM: Artificial Sequence
<220> FEATURE:
<223> OTHER INFORMATION: Primer

<400> SEQUENCE: 117
gtgcataacg gcaagtgatc                                                20

<210> SEQ ID NO 118
<211> LENGTH: 24
<212> TYPE: DNA
<213> ORGANISM: Artificial Sequence
<220> FEATURE:
<223> OTHER INFORMATION: Primer

<400> SEQUENCE: 118
ggctttaaaa gcgagaattt ccgt                                           24

<210> SEQ ID NO 119
<211> LENGTH: 27
<212> TYPE: DNA
<213> ORGANISM: Artificial Sequence
<220> FEATURE:
<223> OTHER INFORMATION: Primer

<400> SEQUENCE: 119
```
ggtcacatcg aacaattcta atctaag                                              27

<210> SEQ ID NO 120
<211> LENGTH: 26
<212> TYPE: DNA
<213> ORGANISM: Artificial Sequence
<220> FEATURE:
<223> OTHER INFORMATION: Primer

<400> SEQUENCE: 120
ggcttttaaa agttctgttc cgagag                                               26

<210> SEQ ID NO 121
<211> LENGTH: 23
<212> TYPE: DNA
<213> ORGANISM: Artificial Sequence
<220> FEATURE:
<223> OTHER INFORMATION: Primer

<400> SEQUENCE: 121
ggtcacatta agaccgttcc ttc                                                  23

<210> SEQ ID NO 122
<211> LENGTH: 19
<212> TYPE: DNA
<213> ORGANISM: Artificial Sequence
<220> FEATURE:
<223> OTHER INFORMATION: Primer

<400> SEQUENCE: 122
tatttaggtg acactatag                                                       19

<210> SEQ ID NO 123
<211> LENGTH: 20
<212> TYPE: DNA
<213> ORGANISM: Artificial Sequence
<220> FEATURE:
<223> OTHER INFORMATION: Primer

<400> SEQUENCE: 123
taatacgact cactataggg                                                      20

<210> SEQ ID NO 124
<211> LENGTH: 21
<212> TYPE: DNA
<213> ORGANISM: Artificial Sequence
<220> FEATURE:
<223> OTHER INFORMATION: Primer

<400> SEQUENCE: 124
gctgatatag aaggtggaaa g                                                    21

<210> SEQ ID NO 125
<211> LENGTH: 21
<212> TYPE: DNA
<213> ORGANISM: Artificial Sequence
<220> FEATURE:
<223> OTHER INFORMATION: Primer

<400> SEQUENCE: 125
ggtcacatca tgactagtgt g                                                    21

<210> SEQ ID NO 126
<211> LENGTH: 20
<212> TYPE: DNA

<213> ORGANISM: Artificial Sequence
<220> FEATURE:
<223> OTHER INFORMATION: Primer

<400> SEQUENCE: 126
gactgctatg gatttagagc                                                    20

<210> SEQ ID NO 127
<211> LENGTH: 20
<212> TYPE: DNA
<213> ORGANISM: Artificial Sequence
<220> FEATURE:
<223> OTHER INFORMATION: Primer

<400> SEQUENCE: 127
gataatgcgt ataatgccac                                                    20

<210> SEQ ID NO 128
<211> LENGTH: 27
<212> TYPE: DNA
<213> ORGANISM: Artificial Sequence
<220> FEATURE:
<223> OTHER INFORMATION: Primer

<400> SEQUENCE: 128
ggctattaaa gcagtacgag tagtgtg                                            27

<210> SEQ ID NO 129
<211> LENGTH: 20
<212> TYPE: DNA
<213> ORGANISM: Artificial Sequence
<220> FEATURE:
<223> OTHER INFORMATION: Primer

<400> SEQUENCE: 129
ctcaacagct gcaattcctg                                                    20

<210> SEQ ID NO 130
<211> LENGTH: 21
<212> TYPE: DNA
<213> ORGANISM: Artificial Sequence
<220> FEATURE:
<223> OTHER INFORMATION: Primer

<400> SEQUENCE: 130
gctgatatag aaggtggaaa g                                                  21

<210> SEQ ID NO 131
<211> LENGTH: 21
<212> TYPE: DNA
<213> ORGANISM: Artificial Sequence
<220> FEATURE:
<223> OTHER INFORMATION: Primer

<400> SEQUENCE: 131
ggtcacatca tgactagtgt g                                                  21

<210> SEQ ID NO 132
<211> LENGTH: 21
<212> TYPE: DNA
<213> ORGANISM: Artificial Sequence
<220> FEATURE:
<223> OTHER INFORMATION: Primer

<400> SEQUENCE: 132
gctgatatag aaggtggaaa g                                                  21

<210> SEQ ID NO 133
<211> LENGTH: 21
<212> TYPE: DNA
<213> ORGANISM: Artificial Sequence
<220> FEATURE:
<223> OTHER INFORMATION: Primer

<400> SEQUENCE: 133
ggtcacatca tgactagtgt g                                     21

<210> SEQ ID NO 134
<211> LENGTH: 27
<212> TYPE: DNA
<213> ORGANISM: Artificial Sequence
<220> FEATURE:
<223> OTHER INFORMATION: Primer

<400> SEQUENCE: 134
ggctattaaa gcagtacgag tagtgtg                               27

<210> SEQ ID NO 135
<211> LENGTH: 23
<212> TYPE: DNA
<213> ORGANISM: Artificial Sequence
<220> FEATURE:
<223> OTHER INFORMATION: Primer

<400> SEQUENCE: 135
cgtgctatcg gtaaagaagt agt                                   23

<210> SEQ ID NO 136
<211> LENGTH: 20
<212> TYPE: DNA
<213> ORGANISM: Artificial Sequence
<220> FEATURE:
<223> OTHER INFORMATION: Primer

<400> SEQUENCE: 136
gtctcagttc gacattggac                                       20

<210> SEQ ID NO 137
<211> LENGTH: 23
<212> TYPE: DNA
<213> ORGANISM: Artificial Sequence
<220> FEATURE:
<223> OTHER INFORMATION: Primer

<400> SEQUENCE: 137
gaatatggag tgtcaagtgg gtc                                   23

<210> SEQ ID NO 138
<211> LENGTH: 27
<212> TYPE: DNA
<213> ORGANISM: Artificial Sequence
<220> FEATURE:
<223> OTHER INFORMATION: Primer

<400> SEQUENCE: 138
ggctattaaa gcagtacgag tagtgtg                               27

<210> SEQ ID NO 139
<211> LENGTH: 23
<212> TYPE: DNA
<213> ORGANISM: Artificial Sequence
<220> FEATURE:

<223> OTHER INFORMATION: Primer

<400> SEQUENCE: 139
cgtgctatcg gtaaagaagt agt                                         23

<210> SEQ ID NO 140
<211> LENGTH: 19
<212> TYPE: DNA
<213> ORGANISM: Artificial Sequence
<220> FEATURE:
<223> OTHER INFORMATION: Primer

<400> SEQUENCE: 140
gagcaccata gatgcagct                                              19

<210> SEQ ID NO 141
<211> LENGTH: 20
<212> TYPE: DNA
<213> ORGANISM: Artificial Sequence
<220> FEATURE:
<223> OTHER INFORMATION: Primer

<400> SEQUENCE: 141
gagtcagtta ctagatctgc                                             20

<210> SEQ ID NO 142
<211> LENGTH: 22
<212> TYPE: DNA
<213> ORGANISM: Artificial Sequence
<220> FEATURE:
<223> OTHER INFORMATION: Primer

<400> SEQUENCE: 142
cagtaatgac tggcggagca gt                                          22

<210> SEQ ID NO 143
<211> LENGTH: 20
<212> TYPE: DNA
<213> ORGANISM: Artificial Sequence
<220> FEATURE:
<223> OTHER INFORMATION: Primer

<400> SEQUENCE: 143
ctgacagatg aagaaacatc                                             20

<210> SEQ ID NO 144
<211> LENGTH: 21
<212> TYPE: DNA
<213> ORGANISM: Artificial Sequence
<220> FEATURE:
<223> OTHER INFORMATION: Primer

<400> SEQUENCE: 144
ggctataaaa tggcttcgct c                                           21

<210> SEQ ID NO 145
<211> LENGTH: 19
<212> TYPE: DNA
<213> ORGANISM: Artificial Sequence
<220> FEATURE:
<223> OTHER INFORMATION: Primer

<400> SEQUENCE: 145
gtcacaaaat gctgtcatg                                              19

-continued

```
<210> SEQ ID NO 146
<211> LENGTH: 22
<212> TYPE: DNA
<213> ORGANISM: Artificial Sequence
<220> FEATURE:
<223> OTHER INFORMATION: Primer

<400> SEQUENCE: 146
cagtaatgac tggcggagca gt                                              22

<210> SEQ ID NO 147
<211> LENGTH: 20
<212> TYPE: DNA
<213> ORGANISM: Artificial Sequence
<220> FEATURE:
<223> OTHER INFORMATION: Primer

<400> SEQUENCE: 147
ctgacagatg aagaaacatc                                                 20

<210> SEQ ID NO 148
<211> LENGTH: 19
<212> TYPE: DNA
<213> ORGANISM: Artificial Sequence
<220> FEATURE:
<223> OTHER INFORMATION: Primer

<400> SEQUENCE: 148
gagcaccata gatgcagct                                                  19

<210> SEQ ID NO 149
<211> LENGTH: 20
<212> TYPE: DNA
<213> ORGANISM: Artificial Sequence
<220> FEATURE:
<223> OTHER INFORMATION: Primer

<400> SEQUENCE: 149
gagtcagtta ctagatctgc                                                 20

<210> SEQ ID NO 150
<211> LENGTH: 22
<212> TYPE: DNA
<213> ORGANISM: Artificial Sequence
<220> FEATURE:
<223> OTHER INFORMATION: Primer

<400> SEQUENCE: 150
cagtaatgac tggcggagca gt                                              22

<210> SEQ ID NO 151
<211> LENGTH: 20
<212> TYPE: DNA
<213> ORGANISM: Artificial Sequence
<220> FEATURE:
<223> OTHER INFORMATION: Primer

<400> SEQUENCE: 151
ctgacagatg aagaaacatc                                                 20

<210> SEQ ID NO 152
<211> LENGTH: 22
<212> TYPE: DNA
<213> ORGANISM: Artificial Sequence
<220> FEATURE:
<223> OTHER INFORMATION: Primer
```

```
<400> SEQUENCE: 152
cagtaatgac tggcggagca gt                                              22

<210> SEQ ID NO 153
<211> LENGTH: 22
<212> TYPE: DNA
<213> ORGANISM: Artificial Sequence
<220> FEATURE:
<223> OTHER INFORMATION: Primer

<400> SEQUENCE: 153
ggtcacatcc tctggaaatt gc                                              22

<210> SEQ ID NO 154
<211> LENGTH: 29
<212> TYPE: DNA
<213> ORGANISM: Artificial Sequence
<220> FEATURE:
<223> OTHER INFORMATION: Primer

<400> SEQUENCE: 154
ggcttttttt tgaaatgtct tgtgttagc                                       29

<210> SEQ ID NO 155
<211> LENGTH: 21
<212> TYPE: DNA
<213> ORGANISM: Artificial Sequence
<220> FEATURE:
<223> OTHER INFORMATION: Primer

<400> SEQUENCE: 155
gtctatatgg caaatctatg c                                               21

<210> SEQ ID NO 156
<211> LENGTH: 29
<212> TYPE: DNA
<213> ORGANISM: Artificial Sequence
<220> FEATURE:
<223> OTHER INFORMATION: Primer

<400> SEQUENCE: 156
ggcttttttt tgaaatgtct tgtgttagc                                       29

<210> SEQ ID NO 157
<211> LENGTH: 21
<212> TYPE: DNA
<213> ORGANISM: Artificial Sequence
<220> FEATURE:
<223> OTHER INFORMATION: Primer

<400> SEQUENCE: 157
gtctatatgg caaatctatg c                                               21

<210> SEQ ID NO 158
<211> LENGTH: 21
<212> TYPE: DNA
<213> ORGANISM: Artificial Sequence
<220> FEATURE:
<223> OTHER INFORMATION: Primer

<400> SEQUENCE: 158
ctcaaactga tttacatcat g                                               21

<210> SEQ ID NO 159
<211> LENGTH: 20
```

```
<212> TYPE: DNA
<213> ORGANISM: Artificial Sequence
<220> FEATURE:
<223> OTHER INFORMATION: Primer

<400> SEQUENCE: 159
gtgcataacg gcaagtgatc                                               20

<210> SEQ ID NO 160
<211> LENGTH: 21
<212> TYPE: DNA
<213> ORGANISM: Artificial Sequence
<220> FEATURE:
<223> OTHER INFORMATION: Primer

<400> SEQUENCE: 160
ctcaaactga tttacatcat g                                             21

<210> SEQ ID NO 161
<211> LENGTH: 20
<212> TYPE: DNA
<213> ORGANISM: Artificial Sequence
<220> FEATURE:
<223> OTHER INFORMATION: Primer

<400> SEQUENCE: 161
gtgcataacg gcaagtgatc                                               20

<210> SEQ ID NO 162
<211> LENGTH: 29
<212> TYPE: DNA
<213> ORGANISM: Artificial Sequence
<220> FEATURE:
<223> OTHER INFORMATION: Primer

<400> SEQUENCE: 162
ggcttttttt tgaaatgtct tgtgttagc                                     29

<210> SEQ ID NO 163
<211> LENGTH: 21
<212> TYPE: DNA
<213> ORGANISM: Artificial Sequence
<220> FEATURE:
<223> OTHER INFORMATION: Primer

<400> SEQUENCE: 163
gtctatatgg caaatctatg c                                             21

<210> SEQ ID NO 164
<211> LENGTH: 21
<212> TYPE: DNA
<213> ORGANISM: Artificial Sequence
<220> FEATURE:
<223> OTHER INFORMATION: Primer

<400> SEQUENCE: 164
cagaggaaat gtagaaatga g                                             21

<210> SEQ ID NO 165
<211> LENGTH: 20
<212> TYPE: DNA
<213> ORGANISM: Artificial Sequence
<220> FEATURE:
<223> OTHER INFORMATION: Primer

<400> SEQUENCE: 165
```

```
caatccatgt ctctgaatgc                                              20

<210> SEQ ID NO 166
<211> LENGTH: 21
<212> TYPE: DNA
<213> ORGANISM: Artificial Sequence
<220> FEATURE:
<223> OTHER INFORMATION: Primer

<400> SEQUENCE: 166
cagaggaaat gtagaaatga g                                            21

<210> SEQ ID NO 167
<211> LENGTH: 20
<212> TYPE: DNA
<213> ORGANISM: Artificial Sequence
<220> FEATURE:
<223> OTHER INFORMATION: Primer

<400> SEQUENCE: 167
caatccatgt ctctgaatgc                                              20

<210> SEQ ID NO 168
<211> LENGTH: 21
<212> TYPE: DNA
<213> ORGANISM: Artificial Sequence
<220> FEATURE:
<223> OTHER INFORMATION: Primer

<400> SEQUENCE: 168
ctcaaactga tttacatcat g                                            21

<210> SEQ ID NO 169
<211> LENGTH: 20
<212> TYPE: DNA
<213> ORGANISM: Artificial Sequence
<220> FEATURE:
<223> OTHER INFORMATION: Primer

<400> SEQUENCE: 169
gtgcataacg gcaagtgatc                                              20

<210> SEQ ID NO 170
<211> LENGTH: 21
<212> TYPE: DNA
<213> ORGANISM: Artificial Sequence
<220> FEATURE:
<223> OTHER INFORMATION: Primer

<400> SEQUENCE: 170
ctcaaactga tttacatcat g                                            21

<210> SEQ ID NO 171
<211> LENGTH: 20
<212> TYPE: DNA
<213> ORGANISM: Artificial Sequence
<220> FEATURE:
<223> OTHER INFORMATION: Primer

<400> SEQUENCE: 171
gtgcataacg gcaagtgatc                                              20

<210> SEQ ID NO 172
<211> LENGTH: 24
<212> TYPE: DNA
<213> ORGANISM: Artificial Sequence
```

```
<220> FEATURE:
<223> OTHER INFORMATION: Primer

<400> SEQUENCE: 172
ggctttaaaa gcgagaattt ccgt                                              24

<210> SEQ ID NO 173
<211> LENGTH: 27
<212> TYPE: DNA
<213> ORGANISM: Artificial Sequence
<220> FEATURE:
<223> OTHER INFORMATION: Primer

<400> SEQUENCE: 173
ggtcacatcg aacaattcta atctaag                                           27

<210> SEQ ID NO 174
<211> LENGTH: 24
<212> TYPE: DNA
<213> ORGANISM: Artificial Sequence
<220> FEATURE:
<223> OTHER INFORMATION: Primer

<400> SEQUENCE: 174
ggctttaaaa gcgagaattt ccgt                                              24

<210> SEQ ID NO 175
<211> LENGTH: 27
<212> TYPE: DNA
<213> ORGANISM: Artificial Sequence
<220> FEATURE:
<223> OTHER INFORMATION: Primer

<400> SEQUENCE: 175
ggtcacatcg aacaattcta atctaag                                           27

<210> SEQ ID NO 176
<211> LENGTH: 24
<212> TYPE: DNA
<213> ORGANISM: Artificial Sequence
<220> FEATURE:
<223> OTHER INFORMATION: Primer

<400> SEQUENCE: 176
ggctttaaaa gcgagaattt ccgt                                              24

<210> SEQ ID NO 177
<211> LENGTH: 20
<212> TYPE: DNA
<213> ORGANISM: Artificial Sequence
<220> FEATURE:
<223> OTHER INFORMATION: Primer

<400> SEQUENCE: 177
gtacatgatg atcccattga                                                   20

<210> SEQ ID NO 178
<211> LENGTH: 27
<212> TYPE: DNA
<213> ORGANISM: Artificial Sequence
<220> FEATURE:
<223> OTHER INFORMATION: Primer

<400> SEQUENCE: 178
ggctttttaa aagttctgtt ccgagag                                           27
```

<210> SEQ ID NO 179
<211> LENGTH: 23
<212> TYPE: DNA
<213> ORGANISM: Artificial Sequence
<220> FEATURE:
<223> OTHER INFORMATION: Primer

<400> SEQUENCE: 179
ggtcacatta agaccgttcc ttc                                              23

<210> SEQ ID NO 180
<211> LENGTH: 27
<212> TYPE: DNA
<213> ORGANISM: Artificial Sequence
<220> FEATURE:
<223> OTHER INFORMATION: Primer

<400> SEQUENCE: 180 ggcttttaa aagttctgtt ccgagag                                           27

<210> SEQ ID NO 181
<211> LENGTH: 23
<212> TYPE: DNA
<213> ORGANISM: Artificial Sequence
<220> FEATURE:
<223> OTHER INFORMATION: Primer

<400> SEQUENCE: 181
ggtcacatta agaccgttcc ttc                                              23

<210> SEQ ID NO 182
<211> LENGTH: 27
<212> TYPE: DNA
<213> ORGANISM: Artificial Sequence
<220> FEATURE:
<223> OTHER INFORMATION: Primer

<400> SEQUENCE: 182 ggcttttaa aagttctgtt ccgagag                                           27

<210> SEQ ID NO 183
<211> LENGTH: 23
<212> TYPE: DNA
<213> ORGANISM: Artificial Sequence
<220> FEATURE:
<223> OTHER INFORMATION: Primer

<400> SEQUENCE: 183
ggtcacatta agaccgttcc ttc                                              23

<210> SEQ ID NO 184
<211> LENGTH: 28
<212> TYPE: DNA
<213> ORGANISM: Artificial Sequence
<220> FEATURE:
<223> OTHER INFORMATION: Primer

<400> SEQUENCE: 184
cttatcaatc atttccagct gacgtctc                                         28

<210> SEQ ID NO 185
<211> LENGTH: 27
<212> TYPE: DNA
<213> ORGANISM: Artificial Sequence
<220> FEATURE:
<223> OTHER INFORMATION: Primer -continued

```
<400> SEQUENCE: 185
tccatatgaa ccaaaagagg tgactgc                                         27

<210> SEQ ID NO 186
<211> LENGTH: 39
<212> TYPE: DNA
<213> ORGANISM: Artificial Sequence
<220> FEATURE:
<223> OTHER INFORMATION: Primer

<400> SEQUENCE: 186
gttagtggag ttctagcgac atattttaaa atgtagaat                            39

<210> SEQ ID NO 187
<211> LENGTH: 21
<212> TYPE: DNA
<213> ORGANISM: Artificial Sequence
<220> FEATURE:
<223> OTHER INFORMATION: Primer

<400> SEQUENCE: 187
ggtcacatca tgactagtgt g                                               21
```

US 7,485,415 B2

SEQUENCE ANALYSIS OF THE TETRAVALENT ROTAVIRUS VACCINE

CROSS REFERENCES TO RELATED APPLICATIONS

This is a U.S. National Stage Application under 35 U.S.C. §371 of International Application No. PCT/US03/05172, filed on Feb. 19, 2003, which claims the benefit of U.S. Provisional Patent Application No. 60/359,960 filed on Feb. 27, 2002 The entire teachings of the above applications are incorporated herein by reference.

BACKGROUND OF THE INVENTION

Rotavirus is a segmented, double-stranded RNA virus that is the major cause of severe gastroenteritis in infants and young children. Profound fluid and electrolyte loss often leads to hospitalization for life-saving rehydration therapy. Where access to medical care is limited or unavailable, volume depletion, shock and death can occur. Annually, nearly one million childhood deaths in developing countries have been ascribed to inadequately treated rotavirus gastroenteritis. In the industrialized world, more than 30% of the children admitted to hospitals with acute gastroenteritis have rotavirus infections.

SUMMARY OF THE INVENTION

The invention is drawn to isolated nucleic acid molecules comprising a gene segment from a rhesus rotavirus (RRV) or from one of three rhesus: human reassortant viruses. In one embodiment, the isolated nucleic acid molecule has a sequence selected from the group consisting of: SEQ ID NO:1-14, inclusive. In another embodiment, the isolated nucleic acid molecule encodes a protein having a sequence selected from the group consisting of: SEQ ID NO:15-28, inclusive. In yet another embodiment, the isolated nucleic acid molecule is a variant of SEQ ID NO: 1, 2, 3, 4, 5, 6, 7, 10, 11, 12, or 14, such as one of the following: a nucleic acid molecule having the sequence of SEQ ID NO: 1 (gene 1) and having a nucleotide change to a G at nucleotide 2120; a nucleic acid molecule having the sequence of SEQ ID NO: 2 (gene 2) and having one or more of the following nucleotide changes: a C at nucleotide 493, and a T at nucleotide 947; a nucleic acid molecule having the sequence of SEQ ID NO:3 (gene 3) and having one or more of the following nucleotide changes: an A at nucleotide 169, a C at nucleotide 283, a C at nucleotide 448, a C at nucleotide 874, a C at nucleotide 1306, and a C at nucleotide 2388; a nucleic acid molecule having the sequence of SEQ ID NO:4 (gene 4) and having one or more of the following nucleotide changes: a C at nucleotide 119, a G at nucleotide 417, a G at nucleotide 809, a C at nucleotide 977, an A at nucleotide 1463, a C at nucleotide 1481, a C at nucleotide 1608, a C at nucleotide 1755, and an A at nucleotide 1953; a nucleic acid molecule having the sequence of SEQ ID NO:5 (gene 5) and having one or more of the following nucleotide changes: an A at nucleotide 75, a T at nucleotide 84, a C at nucleotide 347, a T at nucleotide 667, a C at nucleotide 1186, a G at nucleotide 1219, and an A at nucleotide 1204; a nucleic acid molecule having the sequence of SEQ ID NO: 6 (gene 6) and having one or more of the following nucleotide changes: a C at nucleotide 376, an A at nucleotide 756, an A at nucleotide 1008, and a G at nucleotide 1041; a nucleic acid molecule having the sequence of SEQ ID NO: 7 (gene 7) and having a nucleotide change to a G at nucleotide 387; a nucleic acid molecule having the sequence of SEQ D NO: 10 (gene 10) and having one or more of the following nucleotide changes: an A at nucleotide 92, an A at nucleotide 174, and a G at nucleotide 218; a nucleic acid molecule having the sequence of SEQ ID NO: 11 (gene 11) and having a nucleotide change to A at nucleotide 180; a nucleic acid molecule having the sequence of SEQ ID NO: 12 (DxRRV (serotype 1)) and having a nucleotide change to an A at nucleotide 556; and a nucleic acid molecule having the sequence of SEQ ID NO: 14 (ST3xRRV (serotype 4)) and having a nucleotide change to a G at nucleotide 263. Each gene variant can have one, more than one, or all of the nucleotide changes enumerated for that particular gene. Other variants of any one of nucleic acid molecules having SEQ D NO:1-14, or encoding a polypeptide of SEQ ID NO:15-28, are also included.

DETAILED DESCRIPTION OF THE INVENTION

Human rotavirus serotypes G1-G4 are the major causes of diarrheal gastroenteritis in humans (Gentsch, et al., 1995). The serotypes are determined by epitopic differences in the outer capsid of the virus particle encoded by the VP7 gene. The ROTAMUNE™ (ROTASHIELD™) vaccine is a live virus vaccine comprised of four different rotaviruses, each containing the outer capsid protein, VP7, of one of the major serotypes G1-G4 known to cause disease in humans. The foundation of this vaccine is a virus isolated from a rhesus macaque, rhesus rotavirus (RRV). The virus is sufficiently similar to human strains to permit limited replication in human intestinal tracts and thereby elicit protective immune responses to human rotaviruses. The ROTAMUNE™ vaccine includes RRV (serotype G3, for which VP7 is 96% homologous to VP7 from human serotype 3 viruses); and three rhesus:human reassortant viruses (serotypes G1, G2 and G4). The reassortants are comprised of the rhesus virus genetic background (10 gene segments), but replace the gene segment encoding VP7 with the corresponding gene segments from the human serotype 1 (D strain), 2 (DS1 strain) or 4 (ST3 strain) viruses. Applicants have, for the first time, identified the nucleic acid sequence of all 11 gene segments of each of the four virus strains, including the 10 common gene segments and the four independent gene segments (VP7 gene), for a total of 14 gene segments.

Nucleic Acids of the Invention

Accordingly, the invention pertains to an isolated nucleic acid molecule comprising a gene segment from the rhesus rotavirus (RRV) or from one of the three rhesus: human reassortant viruses. The term, "gene segment," as used herein, refers to a nucleotide sequence, preferably which encodes a polypeptide or protein, and preferably which contains regulatory, non-coding nucleotide sequence(s) present at the 3' and/or 5' end of each gene segment. In a preferred embodiment, the gene segment is selected from the group consisting of the nucleotide sequences shown in SEQ ID NO:1-14, inclusive, as described in Table 1, below.

TABLE 1

SEQ ID NO: 1-14, Nucleic Acids of the Invention

| SEQ ID NO: | Description |
| --- | --- |
| 1 | Gene 1 (RRV) - VP1 |
| 2 | Gene 2 (RRV) - VP2 |
| 3 | Gene 3 (RRV) - VP3 |
| 4 | Gene 4 (RRV) - VP4 |
| 5 | Gene 5 (RRV) - NSP1 |

TABLE 1-continued

SEQ ID NO: 1-14, Nucleic Acids of the Invention

| SEQ ID NO: | Description |
|---|---|
| 6 | Gene 6 (RRV) - VP6 |
| 7 | Gene 7 (RRV) - NSP3 |
| 8 | Gene 8 (RRV) - NSP2 |
| 9 | Gene 9 (RRV) (Serotype 3) - VP7 |
| 10 | Gene 10 (RRV) - NSP4 |
| 11 | Gene 11 (RRV) - NSP5 |
| 12 | Gene 9 (D × RRV) (Serotype 1) - VP7 |
| 13 | Gene 9 (DS1 × RRV) (Serotype 2) - VP7 |
| 14 | Gene 9 (ST3 × RRV) (Serotype 4) - VP7 |

Due to differences in electrophoretic mobility, numerical gene assignments differ among RRV and the reassortant viruses. These differences involve only genes 7, 8 and 9. For the purpose of comparison and discussion, segment 7 is designated as the segment coding for NSP3, segment 8 as the segment coding for NSP2 and segment 9 as the segment coding for outer capsid viral protein 7 (VP7).

The isolated nucleic acid molecules of the present invention can be RNA, for example, mRNA, or DNA, such as cDNA. The RNA or DNA molecules can be double-stranded or single-stranded; single stranded RNA or DNA can be either the coding, or sense, strand or the non-coding, or antisense, strand. The nucleic acid molecule can include all or a portion of the coding sequence of the gene segment and can further comprise additional non-coding sequences such as non-coding 3' and 5' sequences (including regulatory sequences, for example). Additionally, the nucleic acid molecule can be fused to a marker sequence, for example, a sequence that encodes a polypeptide to assist in isolation or purification of the protein. Such sequences include, but are not limited to, those which encode a glutathione-S-transferase (GST) fusion protein and those which encode a hemagglutinin A (HA) polypeptide marker from influenza.

An "isolated" nucleic acid molecule, as used herein, is one that is separated from nucleic acids which normally flank the gene or nucleotide sequence and/or has been completely or partially purified from other transcribed sequences (e.g., as in an RNA library). For example, an isolated nucleic acid of the invention may be substantially isolated with respect to the complex cellular milieu (e.g., the virus) in which it naturally occurs, or culture medium when produced by recombinant techniques, or chemical precursors or other chemicals when chemically synthesized. In some instances, the isolated material will form part of a composition (for example, a crude extract containing other substances), buffer system or reagent mix. In other circumstances, the material may be purified to essential homogeneity, for example as determined by PAGE or column chromatography such as BPLC. Preferably, an isolated nucleic acid molecule comprises at least about 50, 80 or 90% (on a molar basis) of all macromolecular species present.

The nucleic acid molecule can be fused to other coding or regulatory sequences and still be considered isolated. Thus, recombinant nucleic acid contained in a vector is included in the definition of "isolated" as used herein. Also, isolated nucleic acid molecules include recombinant nucleic acid molecules in heterologous host cells, as well as partially or substantially purified nucleic acid molecules in solution. "Isolated" nucleic acid molecules also encompass in vivo and in vitro RNA transcripts (e.g., of cDNA) of the present invention. An isolated nucleic acid molecule or nucleotide sequence can include a nucleic acid molecule or nucleotide sequence which is synthesized chemically or by recombinant means. Therefore, recombinant nucleic acids contained in a vector are included in the definition of "isolated" as used herein. Also, isolated nucleotide sequences include recombinant nucleic acid molecules in heterologous organisms, as well as partially or substantially purified nucleic acid molecules in solution. In viva and in vitro RNA transcripts of the DNA molecules (e.g., cDNA) of the present invention are also encompassed by "isolated" nucleotide sequences. Such isolated nucleotide sequences are useful in the manufacture of the encoded protein, to raise anti-protein antibodies using DNA immunization techniques, and as an antigen to raise anti-DNA antibodies or elicit immune responses, or for detecting expression of the gene in tissue (e.g., human tissue), such as by Northern blot analysis, indicating the presence of infection.

The present invention also pertains to nucleic acid molecules which are not necessarily found in nature but which encode a protein described herein. Thus, for example, nucleic acid molecules which comprise a sequence that is different from the naturally-occurring nucleotide sequence but which, due to the degeneracy of the genetic code, encode a protein that is the same as a protein encoded by a gene segment of the present invention, are also the subject of this invention (e.g., a nucleic acid molecule that encodes a protein having as a sequence any one of SEQ ID NO:15-28, as described in Table 2, below).

TABLE 2

SEQ ID NO: 15-28, Proteins Encoded by Nucleic Acids of the Invention

| SEQ ID NO: | Description | Illustrative Nucleic Acid Encoding the Protein |
|---|---|---|
| 15 | Protein 1 (RRV) - VP1 | 1 |
| 16 | Protein 2 (RRV) - VP2 | 2 |
| 17 | Protein 3 (RRV) - VP3 | 3 |
| 18 | Protein 4 (RRV) - VP4 | 4 |
| 19 | Protein 5 (RRV) - NSP1 | 5 |
| 20 | Protein 6 (RRV) - VP6 | 6 |
| 21 | Protein 7 (RRV) - NSP3 | 7 |
| 22 | Protein 8 (RRV) - NSP2 | 8 |
| 23 | Protein 9 (RRV) (Serotype 3) - VP7 | 9 |
| 24 | Protein 10 (RRV) - NSP4 | 10 |
| 25 | Protein 11 (RRV) - NSP5 | 11 |
| 26 | Protein 9 (D × RRV) (Serotype 1) - VP7 | 12 |
| 27 | Protein 9 (DS1 × RRV) (Serotype 2) - VP7 | 13 |
| 28 | Protein 9 (ST3 × RRV) (Serotype 4) - VP7 | 14 |

The invention also encompasses variants of certain nucleotide sequences of the invention. For example, in one embodiment, the variant nucleotide sequences of the invention comprise the nucleotide differences set forth in Table 4 or Table 8, below.

That is, representative variant embodiments include: a nucleic acid molecule having the sequence of SEQ ID NO: 1 (gene 1) and having a nucleotide change to a G at nucleotide 2120; a nucleic acid molecule having the sequence of SEQ ID NO: 2 (gene 2) and having one or more of the following nucleotide changes: a C at nucleotide 493, and a T at nucleotide 947; a nucleic acid molecule having the sequence of SEQ ID NO:3 (gene 3) and having one or more of the following nucleotide changes: an A at nucleotide 169, a C at nucleotide 283, a C at nucleotide 448, a C at nucleotide 874, a C at nucleotide 1306, and a C at nucleotide 2388; a nucleic acid molecule having the sequence of SEQ ID NO:4 (gene 4) and having one or more of the following nucleotide changes: a C at nucleotide 119, a G at nucleotide 417, a G at nucleotide 809, a C at nucleotide 977, an A at nucleotide 1463, a C at nucleotide 1481, a C at nucleotide 1608, a C at nucleotide 1755, and an A at nucleotide 1953; a nucleic acid molecule having the sequence of SEQ ID NO:5 (gene 5) and having one or more of the following nucleotide changes: an A at nucleotide 75, a T at nucleotide 84, a C at nucleotide 347, a T at nucleotide 667, a C at nucleotide 1186, a G at nucleotide 1219, and an A at nucleotide 1204; a nucleic acid molecule having the sequence of SEQ ID NO: 6 (gene 6) and having one or more of the following nucleotide changes: a C at nucleotide 376, an A at nucleotide 756, an A at nucleotide 1008, and a G at nucleotide 1041; a nucleic acid molecule having the sequence of SEQ ID NO: 7 (gene 7) and having a nucleotide change to a G at nucleotide 387; a nucleic acid molecule having the sequence of SEQ ID NO:10 (gene 10) and having one or more of the following nucleotide changes: an A at nucleotide 92, an A at nucleotide 174, and a G at nucleotide 218; a nucleic acid molecule having the sequence of SEQ ID NO: 11 (gene 11) and having a nucleotide change to A at nucleotide 180; a nucleic acid molecule having the sequence of SEQ ID NO: 12 (DxRRV (serotype 1)) and having a nucleotide change to an A at nucleotide 556; and a nucleic acid molecule having the sequence of SEQ ID NO: 14 (ST3xRRV (serotype 4)) and having a nucleotide change to a G at nucleotide 263. Each gene variant can have one of the nucleotide changes, or can have more than one, or all, of the nucleotide changes enumerated for that particular gene.

Such variants can be naturally-occurring, such as in the case of allelic variation or base substitution in a clinical isolate, or non-naturally-occurring, such as those induced by various mutagens and mutagenic processes. Other intended variations can also be included in any one of the isolated nucleic acids of the invention (e.g., in any one of SEQ ID NO: 1-14 or in a nucleic acid molecule encoding a polypeptide of any one of SEQ ID NO: 15-28); such intended variations include, but are not limited to, addition, deletion and substitution of one or more nucleotides which can result in conservative or non-conservative amino acid changes, including additions and deletions. Preferably the nucleotide (and/or resultant amino acid) changes are silent or conserved; that is, they do not alter the characteristics or activity of protein encoded by the gene segment of the invention.

Other alterations of the nucleic acid molecules of the invention can include, for example, labeling, methylation, internucleotide modifications such as uncharged linkages (e.g., methyl phosphonates, phosphotriesters, phosphoamidates, carbamates), charged linkages (e.g., phosphorothioates, phosphorodithioates), pendent moieties (e.g., polypeptides), intercalators (e.g., acridine, psoralen), chelators, alkylators, and modified linkages (e.g., alpha anomeric nucleic acids). Also included are synthetic molecules that mimic nucleic acid molecules in the ability to bind to designated sequences via hydrogen bonding and other chemical interactions. Such molecules include, for example, those in which peptide linkages substitute for phosphate linkages in the backbone of the molecule.

In a related aspect, the nucleic acid molecules of the invention are used as probes or primers in assays. “Probes” are oligonucleotides that hybridize in a base-specific manner to a complementary strand of nucleic acid molecules. Such probes include polypeptide nucleic acids, as described in Nielsen et al., *Science,* 254, 1497-1500 (1991). Typically, a probe comprises a region of nucleotide sequence that hybridizes under highly stringent conditions to at least about 15, typically about 20-25, and more typically about 40, 50 or 75, consecutive nucleotides of a nucleic acid molecule comprising a nucleotide sequence selected from SEQ ID NO: 1-14, and the complement of SEQ ID NO: 1-14. More typically, the probe further comprises a label, e.g., radioisotope, fluorescent compound, enzyme, or enzyme co-factor.

As used herein, the term “primer” refers to a single-stranded oligonucleotide which acts as a point of initiation of template-directed DNA synthesis using well-known methods (e.g., PCR, LCR) including, but not limited to those described herein. The appropriate length of the primer depends on the particular use, but typically ranges from about 15 to 30 nucleotides.

The nucleic acid molecules of the invention such as those described above can be identified and isolated using standard molecular biology techniques and the sequence information provided in SEQ ID NO: 1-14. For example, nucleic acid molecules can be amplified and isolated by the polymerase chain reaction using synthetic oligonucleotide primers designed based on one or more of the sequences provided in SEQ ID NO: 1-14 and/or the complement of SEQ ID NO: 1-14. See generally *PCR Technology: Principles and Applicationsfor DNA Amplification* (ed. H. A. Erlich, Freeman Press, NY, N.Y., 1992); *PCR Protocols: A Guide to Methods and Applications* (Eds. Innis, et al., Academic Press, San Diego, Calif., 1990); Mattila et al., *Nucleic Acids Res.,* 19:4967 (1991); Eckert et al., *PCR Methods and Applications,* 1:17 (1991); PCR (eds. McPherson et al., IRL Press, Oxford); and U.S. Pat. No. 4,683,202. The nucleic acid molecules can be amplified using cDNA, RNA, or mRNA as a template, cloned into an appropriate vector and characterized by DNA sequence analysis.

Other suitable amplification methods include the ligase chain reaction (LCR) (see Wu and Wallace, *Genomics,* 4:560 (1989), Landegren et al., *Science,* 241:1077 (1988), transcription amplification Kwoh et al., *Proc. Natl. Acad. Sci. USA,* 86:1173 (1989)), and self-sustained sequence replication (Guatelli et al., *Proc. Nat. Acad. Sci. USA,* 87:1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

Antisense nucleic acid molecules of the invention can be designed using the nucleotide sequences of SEQ ID NO: 1-14 and/or the complement of SEQ ID NO: 1-14, or a portion of the nucleotide sequence of SEQ ID NO: 1-14 and/or the complements thereof, and constructed using chemical synthesis and enzymatic ligation reactions using procedures known in the art. For example, an antisense nucleic acid molecule (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Alternatively, the antisense nucleic acid molecule can be produced biologically using an expression vector into which a nucleic acid molecule has been subcloned in an antisense orientation (i.e., RNA transcribed from the inserted nucleic acid molecule will be of an antisense orientation to a target nucleic acid of interest).

Another aspect of the invention pertains to nucleic acid constructs containing a nucleic acid molecule selected from the group consisting of SEQ ID NO: 1-14 and the complement of SEQ ID NO: 1-14 (or a portion thereof). The constructs comprise a vector (e.g., an expression vector) into which a sequence of the invention has been inserted in a sense or antisense orientation. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). In general, expression vectors of utility in recombinant DNA techniques are often in the form of plasmids. However, the invention is intended to include such other forms of expression vectors, such as viral vectors (e.g., replication defective retroviruses, adenoviruses and adeno-associated viruses, negative strand RNA virus vectors, VEE vectors) that serve equivalent functions.

Preferred recombinant expression vectors of the invention comprise a nucleic acid molecule of the invention in a form suitable for expression of the nucleic acid molecule in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed and the level of expression of protein desired. The expression vectors of the invention can be introduced into host cells to thereby produce proteins, including fusion proteins, encoded by nucleic acid molecules as described herein.

The recombinant expression vectors of the invention can be designed for expression of a protein described herein, in prokaryotic or eukaryotic cells, e.g., bacterial cells such as *E. coli*, insect cells (using baculovirus expression vectors), yeast cells or mammalian cells. Suitable host cells are discussed further in Goeddel, supra. Alternatively, the recombinant expression vector can be transcribed and translated in vitro, for example using T7 promoter regulatory sequences and T7 polymerase.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell but are still included within the scope of the term as used herein.

A host cell can be any prokaryotic or eukaryotic cell. For example, a nucleic acid molecule of the invention can be expressed in bacterial cells (e.g. *E. coli*), insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing a foreign nucleic acid molecule (e.g., DNA) into a host cell, including calcium phosphate or calcium chloride co-precipitation, DEAB-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those that confer resistance to drugs, such as G418, hygromycin and methotrexate. Nucleic acid molecules encoding a selectable marker can be introduced into a host cell on the same vector as the nucleic acid molecule of the invention or can be introduced on a separate vector. Cells stably transfected with the introduced nucleic acid molecule can be identified by drug selection (e.g., cells that have incorporated the selectable marker gene will survive, while the other cells die).

A host cell of the invention, such as a prokaryotic or eukaryotic host cell in culture, can be used to produce (i.e., express) a protein described herein. Accordingly, the invention further provides methods for producing a protein using the host cells of the invention. In one embodiment, the method comprises culturing the host cell of the invention (into which a recombinant expression vector encoding a protein described herein has been introduced) in a suitable medium such that the protein is produced. In another embodiment, the method further comprises isolating the protein from the medium or the host cell.

The invention will be further described by the following non-limiting examples. The teachings of all publications cited herein are incorporated herein by reference in their entirety.

EXAMPLES

Example 1

Consensus Sequencing

Materials and Methods

Viral Stocks

A rotavirus seed bank system was developed for the ROTAMUNE™ vaccine consisting of a Master Virus Seed (MVS) Bank, a Primary Virus Seed (PVS) Bank and a Manufacturer's Working Virus Seed (MWVS) Bank. The nucleotide sequence of all 11 gene segments of each of the four strains comprising the commercial virus seed (MWVS-5, 6, 7 and 8) were identified and the sequence identity (genetic equivalence) between the commercial virus seeds and the clinical virus seeds (MWVS-1, 2, 3, and 4) were demonstrated.

A subset of Manufacturer's Working Virus Seed (MWVS), representing clinical lots (MWVS 1-4) and commercial lots (MWVS 5-8), was used. The strains used in this study are:

| | | |
|---|---|---|
| 1) | D × RRV | Lot MWVS-5 Type-1 |
| 2) | DS1 × RRV | Lot MWVS-6 Type-2 |
| 3) | RRV | Lot MWVS-7 Type-3 |
| 4) | ST3 × RRV | Lot MWVS-8 Type-4 |
| 5) | RRV | Lot MWVS-1 |
| 6) | DS1 × RRV | Lot MWVS-2 |
| 7) | D × RRV | Lot MWVS-3 |
| 8) | ST3 × RRV | Lot MWVS-4 |

RNA Isolation

Genomic RNAs from the aliquots of each MWVS were extracted using Trizol-LS™ reagent (Life Technologies, Grand Island, N.Y.). RNA was resuspended in RNase-free water and used for all genomic amplifications.

Reverse Transcription-Polymerase Chain Reaction (RT-PCR) Amplification

RT-PCR amplifications spanning individual fall length RNA gene segments of the rotavirus genome were performed by using the GeneAmp XL RNA PCR Kit (Perkin-Elmer) and primer pairs specific to each individual rotavirus gene segment. Common RRV primers were used for all segments of the three reassortants, except for gene 9 where primers specific to gene 9 of the rhesus or of the different human rotavirus sequences (RRV, HRV-D, HRV-DS1 and GRV-ST3) were used. Primers are shown in Table 3A.

TABLE 3A

Primers Used For Amplification of Genomic Fragments

| Gene | Primer Name | Nucleotide | Sequence 5'→3' | SEQ ID |
|---|---|---|---|---|
| 1 | RRV-101 | 1-27 | GGCTATTAAAGCTGTACAATGGGGAAG | 29 |
|  | RRV-102 | 3265-3294 | CTAAGCGTTCTAATCTTGAAAGAAGTTTGC | 30 |
| 2 | RRV-201 | 1-27 | GGCTATTAAAGGCTCAATGGCGTACAG | 31 |
|  | RRV-202 | 2683-2708 | GGTCATATCTCCACAATGGGGTTGGC | 32 |
| 3 | *RRV-301A | 1-25 | GGCTATTAAAGCAGTACGAGTAGTG | 33 |
|  | *RRV-302A | 2571-2591 | GGTCACATCATGACTAGTGTG | 34 |
| 4 | RRV-401 | 1-21 | GGCTATAAAATGGCTTCGCTC | 35 |
|  | RRV-402 | 2341-2362 | GGTCACATCCTCTGGAAATTGC | 36 |
| 5 | *RRV-501A | 1-29 | GGCTTTTTTTGAAATGTCTTGTGTTAGC | 37 |
|  | *RRV-502A | 1576-1599 | GGTCACAGTTTTTGCTGGCTAGGC | 38 |
| 6 | RRV-601 | 1-26 | GGCTTTTAAACGAAGTCTTCAACATG | 39 |
|  | RRV-602 | 1332-1356 | GGTCACATCCTCTCACTATACCATC | 40 |
| 7 | RRV-701 | 1-25 | GGCATTTAATGCTTTTCAGTGGTTG | 41 |
|  | RRV-702 | 1056-1077 | GGTCACATAACGCCCCTATAGC | 42 |
| 8 | RRV-801 | 1-29 | GGCTTTTAAAGCGTCTCAGTCGCCGTTCG | 43 |
|  | RRV-802 | 1037-1059 | GGTCACATAAGCGCTTTCTATTC | 44 |
| 9 | **RRV-901 | 1-24 | GGCTTTAAAAGCGAGAATTTCCGT | 45 |
|  | RRV-902 | 1041-1062 | GGTCACATCATACATTTCTAAC | 46 |
|  | D-RRV-902 | 1036-1062 | GGTCACATCGAACAATTCTAATCTAAG | 47 |
|  | DS1-RRV-902 | 1035-1062 | GGTCACATCGAACAATTCTGACCAAATC | 48 |
|  | ST3-RRV-902 | 1036-1062 | GGTCACATCATACATTTCTATTTTAGG | 49 |
| 10 | RRV-1001 | 1-27 | GGCTTTTTAAAAGTTCTGTTCCGAGAG | 50 |
|  | RRV-1002 | 728-750 | GGTCACATTAAGACCGTTCCTTC | 51 |
| 11 | RRV-1101 | 1-24 | GGCTTTTAAAGCGCTACAGTGATG | 52 |
|  | RRV-1102 | 644-667 | GGTCACATAACTGGAGTGGGGAGC | 53 |

Primers named . . . 01 are (+) sense and primers named . . . 02 are (−) sense.
*Primers 301A, 302A, 501A, and 502A reflect the actual termini sequence as determined.
**Primer 901 was used to amplify all four serotypes, while primer 902 was designed specifically for each.

RT-PCR amplification steps were as follows:

| RT REACTION | |
|---|---|
| RNA (RNA + water) | 10 μl |
| RNase-free water | — |
| 5× XL RT buffer | 4 μl |
| dNTP mix (2.5 mM each dNTP) | 1.6 μl |
| rTth polymerase | 2.5 μl |
| 25 mM Mn(OAc2) | 0.88 μl |
| RT (downstream) primer (20 pmoles/μl) | 1 μl |
| TOTAL: | 20 μl |

RNA (100-500 ng per reaction) was mixed with water and 5× SL RT buffer in a Gene-amp tube. The mixture was denatured at 96° C. for 5-6 minutes in a pre-heated thermal cycler, and then placed on ice immediately for 3 minutes to quick cool. Samples were pulse-spun in microfuge to remove any condensation on caps, and the remaining ingredients were added. A drop of mineral oil was added to each tube, and samples were placed in pre-heated thermal cycler at 40° C. The RT thermal cycle was 40° C. for 60 minutes, followed by 45° C. for 60 minutes and then 4° C., soak. If several different fragments from the same RNA template were amplified, the entire reaction was scaled up in one tube, eliminating only the primer from the mix. One μl of the RT (+sense) primer was added to each reaction tube, and then 19 μl of the scaled-up RT mix were added.

| PCR REACTION | |
|---|---|
| RNase-free water | 58.8 μl |
| 5× XL Chelating Buffer | 16 μl |
| 25 mM Mg(OAc2) | 3.2 μl |
| PCR (upstream) primer (20 pmoles/μl) | 1.5 μl |
| RT (downstream) primer (20 pmoles/μl) | 0.5 μl |
| TOTAL | 80 μl |

The reagents were mixed for each sample; 80 μl PCR mix were added to the 20 μl RT reaction under the oil, and mixed by pipetting up and down several times. The samples were placed in pre-heated thermal cycler (hot-start) at 94° C. and cycled as follows: 94° C. denaturation for 3 minutes, followed by 40 cycles of denaturation at 94° C. for 1 minute, primer annealing at 40° C. for 30 seconds, and extension at 70° C. for five minutes. A final extension step was run at 70° C. for 10 minutes, followed by a soak cycle at 4° C.

Ten μl of reaction were run on agarose gel. Products were purified using Promega's Wizard PCR preps DNA purification system (Madison Wis.) either directly or using gel purification from low-melting agarose.

RNA Ligation RT-PCR to Determine Consensus Nucleotide Sequence of the Gene Termini The nucleotide sequence of the absolute 3' and 5' termini of the eleven RNA gene segments of the rotavirus vaccine stains was determined using an RNA ligation reverse transcription-PCR protocol modified from Sidhu et al. (*Virology* 193:66-72, 1993) for use on double-stranded RNA. Genomic RNA was extracted using Trizol-LS™ reagent (Life Technologies) and 2-3 μg was treated with Tobacco Acid Pyrophosphatase (TAP) at 37° C. for 1 hour in a 40 μl volume according to the manufacturer's directions (Epicentre Technologies). This step was used to remove the CAP structure on the 5' end of the plus strand of the genomic RNA segments, and leave behind a 5' monophosphate that was used for RNA ligation. The TAP-treated RNA was extracted with phenyl/chloroform/isoamyl alcohol (25:24:1) and ethanol-precipitated. The RNA pellet was air-dried and resuspended in 13.7 μl of RNase-free water. The double-stranded RNA was then denatured at 96° C. for 4 minutes and quick-chilled on ice for 2 minutes. The reagents required for RNA ligation in at 20 μl volume were then added. The final ligation reaction conditions were 1× RNA ligase buffer (New England Biolabs), 10% DMSO (Sigma D-2650), 20 U Promega RNasin, and 36 U NEB T4 RNA ligase. Ligation was performed at 16° C. overnight (approximately 16 hours). The ligated RNA was phenyl extracted and ethanol precipitated as described above, and the RNA pellet was resuspended in 15 μl of water. One μl of ligated RNA was seeded into each of 11 RT-PCR reactions containing rotavirus gene-specific primers (shown in Table 3B) designed to amplify across the ligated RNA junction.

TABLE 3B

Rotavirus Primers Used to Amplify across Ligated RNA Junctions (Gene Termini)

| Gene | Primer | Nucleotide | Sequence 5'→3' | SEQ ID |
|---|---|---|---|---|
| 1 | RRV-101T | 206-229 | CCCAAGCTTGTGTGGCATTCTCTATAACATCGC | 54 |
|   | RRV-102T | 3163-3186 | CCCGGATCCGGCTCATGGATAAGCTTATTCTGC | 55 |
|   | RRV-103T | 301-324 | CCCAAGCTTCAAATCTGCTTCTAGCGGCTTACC | 56 |
|   | RRV-104T | 3084-3107 | CCCGGATCCTAAAGGAAAGATACCAGCTGTCAC | 57 |
| 2 | RRV-201T | 147-170 | CCCAAGGTTCCTTTTGAGATAGCACTTTCTCTG | 58 |
|   | RRV-202T | 2524-2547 | CCCGGATCCACCACAACAATTTGATTTTAGAGC | 59 |
|   | RRV-203T | 270-293 | CTTCTTTTTGATGTTCTTCCTTAG | 60 |
|   | RRV-204T | 2470-2493 | TGTAGCGAATTATGACTGGGTTCC | 61 |
| 3 | RRV-301T | 128-151 | CCCAAGCTTAAGAAATGCATTCTCGTAACTGTC | 62 |
|   | RRV-302T | 2415-2438 | CCCGGATCCGTCAATCTAGAATGTTTATTCCAC | 63 |

TABLE 3B-continued

Rotavirus Primers Used to Amplify across
Ligated RNA Junctions (Gene Termini)

| Gene | Primer | Nucleotide | Sequence 5'→3' | SEQ ID |
|---|---|---|---|---|
| | RRV-303T | 227-250 | TTGAATCTCAACAGCTGCAATTCC | 64 |
| | RRV-304T | 2344-2367 | AAACGTTAGTGGAGTTCTAGCGAC | 65 |
| 4 | RRV-401T | 137-160 | CCCAAGCTTCCCAGTTAACTGGAGCATAACCTG | 66 |
| | RRV-402T | 2145-2168 | CCCGGATCCAACTGACTCTCCGGTCATCTCAGC | 67 |
| | RRV-403T | 208-231 | GAACGTTGTTGGTTGATAAGGACC | 68 |
| | RRV-404T | 2049-2072 | AGTCTTTGAAGCGGGAACAGATGG | 69 |
| 5 | RRV-501T | 155-178 | CCCAAGCTTATTGACAACACTCAATGCACCACC | 70 |
| | RRV-502T | 1396-1419 | CCCGGATCCGAATTAGATCACTTGCCGTTATGC | 71 |
| | RRV-503T | 214-237 | GATGCACCACTGACAAACATGAGC | 72 |
| | RRV-504T | 1302-1325 | GATACTGGAAACCGAGGCTCTTCC | 73 |
| 6 | RRV-601T | 166-189 | CCCAAGCTTTCGGCAGATTACCAATTCCTCCAG | 74 |
| | RRV-602T | 1170-1193 | CCCGGATCCCAGCGTGTATTTACAGTGGCTTCC | 75 |
| | RRV-603T | 246-269 | ACGGGCCGTTTCGACATAGTTAGC | 76 |
| | RRV-604T | 1076-1099 | AGAATACGCGATACCAGTTGGACC | 77 |
| 7 | RRV-705T | 94-117 | CCCAAGCTTTCAAGAGTAGAAGTTGCAGCAACC | 78 |
| | RRV-706T | 923-946 | CCCGGATCCAAAGGATTATTGCAGCAATGCAAC | 79 |
| | RRV-703T | 146-169 | ACTCTTTACTCTAGTCTAGTATATACCTC | 80 |
| | RRV-704T | 800-823 | AAATCAGACATTGAACAACAGCTG | 81 |
| | RRV-707T | 285-311 | TAGCTACAGTTCGAGAGTCAGTCATCC | 82 |
| | RRV-708T | 756-782 | CAATAGAATGGTATCTAAGATCGATGG | 83 |
| 8 | RRV-801T | 194-217 | CCCAAGCTTGAATTGTGGCGGTGGTGCGATACC | 84 |
| | RRV-802T | 920-943 | CCCGGATCCAAAATGAAGCGGGAAAGTAATCCG | 85 |
| | RRV-803T | 284-307 | CGCTTCACAAATTAACACCGCCAC | 86 |
| | RRV-804T | 847-870 | GAACTGGTATGCGTTTACATCCTC | 87 |
| 9 (RRV) | RRV-901T | 227-250 | CCCAAGCTTCGTATGCAGTGTCCATTGAACCAG | 88 |
| | RRV-902T | 905-928 | CCCGGATCCGCATTAATTGGAAGAAATGGTGGC | 89 |
| | RRV-903T | 304-327 | TATTTCTGTTGCAGCTTCAGTTGG | 90 |
| | RRV-904T | 835-858 | GTTGGAGGTTCTGATGTTCTCGAC | 91 |
| 9 (DSI) | DS1-901T | 134-157 | CCCAAGCTTACCTGAAAATTATGTAGTCCATCG | 92 |
| | DS1-902T | 882-905 | CCCGGATCCCCCACAAGTTCAAAGAATCATGCG | 93 |
| | DS1-903T | 220-243 | AGCGTCTAGTGACCCCGTTATTGG | 94 |
| | DS1-904T | 828-851 | AATTCAAGTTGGTGGACCGAACGC | 95 |
| 9 (D) | D-901T | 122-145 | CCCAAGCTTTGTAGTCCATTATTCGAGTCACTG | 96 |
| | D-902T | 886-909 | CCCGGATCCCAAACTGAGAGAATGATGAGAGTG | 97 |
| | D-903T | 220-243 | AGCGTCCATTGATCCTGTTATTGG | 98 |
| | D-904T | 819-842 | TGTAGCTGTAATACAAGTTGGTGG | 99 |

TABLE 3B-continued

Rotavirus Primers Used to Amplify across Ligated RNA Junctions (Gene Termini)

| Gene | Primer | Nucleotide | Sequence 5'→3' | SEQ ID |
|---|---|---|---|---|
| 9 (ST3) | ST3-901T | 219-242 | CCCAAGCTTGTATCCATAGATCCAGTAATTGGC | 100 |
| | ST3-902T | 920-943 | CCCGGATCCAATGGTGGCAAGTATTCTACACTG | 101 |
| | ST3-903T | 304-327 | AATTTGAGTTGGAGCTTCTGATGG | 102 |
| | ST3-904T | 861-884 | AACAGCTGATCCCACAACTTCTCC | 103 |
| 10 | RRV-1005T | 141-168 | GTACAGTTAGGACAGAAGCAATGTATGG | 104 |
| | RRV-1006T | 628-655 | ATCGGACCTGATGACTGGTTGAGAAGCC | 105 |
| | RRV-1007T | 359-386 | CTTATCAATCATTTCCAGCTGACGTCTC | 184 |
| | RRV-1008T | 533-559 | TCCATATGAACCAAAAGAGGTGACTGC | 185 |
| 11 | RRV-1101T | 124-147 | CCCAAGCTTTGAAACGTACTGTTCACTCCTACC | 106 |
| | RRV-1102T | 470-493 | CCCGGATCCTTGAAGCAGATTCCGATTCAGACG | 107 |
| | RRV-1103T | 205-228 | CCCAAGCTTGTCGTTTGAAGCAGAATCAGATGG | 108 |
| | RRV-1104T | 403-426 | CCCGGATCCGTATCAACAGTTTCCAAGAAGGAG | 109 |

Odd numbered primers are negative sense; Even numbered primers are positive sense.
Primers ending with 03, 04 or 07, 08 (genes 7 and 10) are used for reverse transcription and first round PCR.
Primers ending with 01, 02 or 05, 06 (genes 7 and 10) are used for second round (nested) PCR and sequencing.
Primers ending with 01 and 103T, 1103T, 705T contain 9 nucleotides at the 5' end that include a HindIII site.
Primers ending with 02 and 104T, 1104T, 706T contain 9 nucleotides at the 5' end that include a BamHI site.

The RT step and the first round of PCR was done using the Perkin-Elmer GeneAmp Thermostable rTth Reverse Transcriptase RNA PCR Kit (catalog #N808-0069) as per the manufacturer's specifications with modification.

RT mix for one reaction (multiply μl volumes by number of reactions needed)

| | |
|---|---|
| 10× RT buffer | 2 |
| 2.5 mM dNTP mix* | 1.6 |
| 10 mM MnCl2 | 2 |
| rTth DNA polymerase (2.5 U/μl) | 2 |
| RNase-free water | 7.4 |
| TOTAL: | 15 μl |

*prepared by mixing equal volumes of each 10 mM dNTP stock (dATP, dGTP, dCTP, dTTP).

Fifteen μl of RT mix were combined with 2 μl of upstream and 2 μl of downstream first round PCR primers (each are 20 pmoles/μl) and 1 μl of ligated RNA in a 0.5 ml thin-walled GeneAmp tube and overlaid with 2 drops of Sigma mineral oil. Since both plus and minus RNA strands of the genome have been ligated, each of the first round PCR primers could be used for cDNA synthesis during reverse transcription. For each different primer pair used, a negative control was set up that contained 1 μl of water in place of the ligated RNA. The 0.5 ml reaction tubes were loaded in the PE thermal cycler 480 at 4° C. and the cycler was quickly ramped to 80° C. and then ramped back to 45° C. RT was performed at 45° C. for 30 minutes, followed by 50° C. for 30 minutes. Following RT, 80 μl of first-round PCR mix was added to each RT reaction over the oil and the tubes were pulse spun in a microcentrifuge.

First Round PCR Mix for one reaction (multiply μl volumes by the number of reactions needed):

| | |
|---|---|
| 2.5 mM dNTP mix | 2.4 |
| 25 mM MgCl2 | 9 |
| 10× chelating buffer | 8 |
| RNase-free water | 60.0 |
| TOTAL | 80 μl |

Thermal cycling profile was as follows: 94° C. for 2 minutes; 40 cycles of 94° C. for 1 minute, 45° C. for 1 minute, 72° C. for 1 minute; 72° C., for 10 minutes; and 4° C., soak. Following each first round PCR, a second round (nested) PCR amplification was performed using Perkin-Elmer reagents and AmpliTaq Gold™ DNA polymerase (catalog #N808-0241).

Second Round (nested) PCR mix for one reaction (multiply μl volumes by the number of reactions needed)

| | |
|---|---|
| 10× PCR buffer II (catalog #N808-0010) | 10 |
| 25 mM MgCl2 | 8 |
| 2.5 mM dNTP mix | 8 |
| AmpliTaq Gold DNA polymerase (5 U/μl) | 0.5 |
| RNase-free water | 65.5 |
| TOTAL: | 92 μl |

The second round PCR mix (92 µl) was combined with 2 µl of upstream and 2 µl of downstream second round PCR primers (each are 20 pmoles/µl) and 4 µl of the first round PCR reaction (including negative controls). The reactions were overlaid with 2 drops of Sigma mineral oil and pulse spun. The thermal cycling profile was the same as for the first round PCR except the initial step at 94° C. for 2 minutes was extended to 12 minutes to activate the AmpliTaq Gold™ DNAP.

Second round PCR products (10 µl) were analyzed by agarose gel electrophoresis with ethidium bromide. The ligation PCR products were gel-purified using the Promega Wizard™ PCR preps DNA purification system. A consensus sequence for the PCR amplified products was determined. If necessary to resolve nucleotide sequence ambiguities, the PCR products were cloned using pGEM-T Easy Vector System I (Promega, Madison, Wis.) and multiple clones were sequenced.

DNA Sequencing

A consensus sequence for the PCR amplified products was generated by using, the Applied Biosystems-PRISM fluorescent dye terminator cycle sequencing kit with AmpliTaq DNA Polymerase-FS, and the Applied Biosystems 377 DNA sequencer (ABI-Perkin-Elmer). Over 100 primers spaced approximately 200 nucleotides apart on each strand were used for sequencing both strands of the PCR products. When needed, gel purified PCR products were cloned by using pGEM-T Easy Vector System I (Promega, Madison, Wis.). Positive clones were selected by T7/SP6 primer-specific PCR screening and the amplified PCR products of the positive clones were directly sequenced as described above. Sequences were analyzed by using MacVector gene analysis program (Oxford Molecular, Oxford, UK).

Results

Eleven full length gene segments were amplified for each virus strain using high fidelity RNA-PCR amplification reactions as described above. Both strands of the amplified products were sequenced directly by using RRV-specific primers, except for gene segment 9, for which strain specific primers were used. The sequences for each of the eleven RRV (MWVS-7) genes are SEQ ID NO:1-11, respectively as shown in Table 1 above. Gene segment 9 sequences for the three reassortants are SEQ ID NO:12 (DxRRV (MWVS-5)), SEQ ID NO:13 (DS1xRRV (MWVS-6)), and SEQ ID NO:14 (ST3 x RRV (MWVS-8)). The putative protein sequences for each of these are SEQ ID NO:15-28, respectively, as shown in Table 2 above.

Table 4 lists nucleotide differences identified between the parent RRV (MWVS-7) strain and the three reassortant viruses DxRRV (MWVS-5), DS1 x RRV MWVS-6), and ST3 x RRV (MWVS-8). These nucleotide differences were common to both clinical (MWVS 1-4) and commercial (MWVS 5-8) seeds.

TABLE 4

List of nucleotide changes identified in the gene segments of the three reassortants as compared to the progenitor RRV strain

| Gene | Nucleotide Position | MWVS-5 & MWVS-3 (D × RRV) | MWVS-6 & MWVS-2 (DS1 × RRV) | MWVS-8 & MWVS-4 (STS × RRV) | Amino Acid |
|---|---|---|---|---|---|
| 1 | 2120 | A→G | — | — | Lys→Arg |
| 2 | 493* | — | — | A→C | silent |
|  | 947 | C→T | — | — | Leu→Phe |
| 4 | 119 | T→C | T→C | — | Leu→Pro |
|  | 809 | A→G | A→G | — | Tyr→Cys |
|  | 977 | T→C | — | — | Met→Thr |
|  | 1463 | — | — | C→A | Thr→Asn |
|  | 1755 | T→C | — | — | silent |
| 5 | 84 | C→T | — | — | silent |
|  | 347 | — | T→C | — | Leu→Ser |
| 6 | 376 | — | — | A→C | Lys→Thr |
|  | 756 | G→A | G→A | G→A | Ala→Thr |
|  | 1008 | G→A | — | — | Ala→Thr |
|  | 1041 | A→G | — | — | Lys→Glu |
| 7 | 387 | — | A→G | A→G | Asn→Ser |
| 10 | 174 | G/A mix† | — | G/A mix† | Ala/Thr mix |
|  | 218 | A→G | — | — | silent |
| 11 | 180 | G→A | — | — | silent |

— Identical to RRV.
†Position 174 is an 'A' in RRV (MWVS-1 and MWVS-7).

Example 2

Clonal Analysis

Materials and Methods

Viral Stocky

Viral stocks were from the Wyeth Laboratories, Inc., in Marietta, Pa., USA, rotavirus seed bank system. The strains used in this study are:

Working virus seeds for commercial vaccine production:

| 1) | D × RRV | Lot MWVS-5 Type-1, Serotype G1 |
| 2) | DS1 × RRV | Lot MWVS-6 Type-2, Serotype G1 |
| 3) | RRV | Lot MWVS-7 Type-3, Serotype G3 |
| 4) | ST3 × RRV | Lot MWVS-8 Type-4, Serotype G4 |

Working virus seeds for clinical vaccine production:

| 5) | RRV | Lot MWVS-1 (ST3), Serotype G3 |
| 6) | DS1 × RRV | Lot MWVS-2 (TS2), Serotype G2 |

-continued

| 7) | D × RRV | Lot MWVS-3 (ST1), Serotype G1 |
| 8) | ST3 × RRV | Lot MWVS-4 (ST4), Serotype G4 |

Commercial vaccine lots used in clonal analysis were as follows:
Serotype G1: I973020, I973017, I983003, I983026
Serotype G2: I973030, I973029, I983008, I983037
Serotype G3: I973026, I983021, I983032
Serotype G4: I97003, I973040, I983030, I973034.

All clinical isolates were plaque purified three times, except for isolates 37 and 38 (purified twice).
  Serotype G1 clinical isolates: clones 1, 16, 22 and 29
  Serotype G2 clinical isolates: clones 3, 4, 8, 9 and 19
  Serotype G3 clinical isolates: clones 5, 6, 10, 11, 12, 20, 21 and 25
  Serotype G4 clinical isolates: clones 37 and 38.

RNA Isolation

Total RNA was extracted from clinical samples, aliquots of virus seed or aliquots of vaccine virus using Trizol-LS™ reagent (Life Technologies, Grand Island, N.Y.). RNA was resuspended in nuclease-free water and used for all RT/PCR amplifications.

Reverse Transcription-Polymerase Chain Reaction (RT-PCR) Amplification

Clonal analysis was carried out to determine the following: 1) the micro-heterogeneity in MWVS-1, 2, 3 and 4 at the 7 nucleotide positions (position 2388 in gene 3, positions 1674 and 1953 in gene 4, positions 75, 667 and 1204 in gene 5, and position 556 in gene 9) which were found to differ from consensus sequence in more than one clinical isolate; 2) the micro-heterogeneity in the four seed strains (MWVS-1, 2, 3 and 4) at position 174 in gene 10, found to contain abase mixture in serotypes G1 and G4 by consensus sequencing; and 3) the micro-heterogeneity in genes 3 and 10 at nucleotide positions 2388 and 174, respectively, in the commercial vaccine lots and their seeds (MWVS-5, 6, 7 and 8).

A portion of each gene spanning the nucleotide position(s) of interest was amplified by RT-PCR using the GeneAmp XL RNA PCR Kit (Perkin-Elmer) and primer pairs listed in Table 5.

TABLE 5

Primer Pairs Used in RT/PCR Amplification of Clinical and Commercial Seeds for Clonal Analysis

| Gene | Nucleotide Of Interest | Primer Name | Primer Sequence (5'→3') | SEQ ID |
|---|---|---|---|---|
| 3 | 2388 | RRV-307 | GCTGATATAGAAGGTGGAAAG | 110 |
|   |   | RRV-302A | GGTCACATCATGACTAGTGTG | 111 |
| 4 | 1674 | RRV-406 | GAGCACCATAGATGCAGCT | 112 |
|   |   | RRV-409 | CTGACAGATGAAGAAACATC | 113 |
|   | 1953 | RRV-406 | GAGCACCATAGATGCAGCT | 114 |
|   |   | RRV-408 | GAGTCAGTTACTAGATCTGC | 115 |
| 5 | 75, 667, 1204 | RRV-501A | GGCTTTTTTTTGAAATGTCTTGTGTTAGC | 116 |
|   |   | RRV-507 | GTGCATAACGGCAAGTGATC | 117 |
| 9 (G1) | 556 | RRV-901 | GGCTTTAAAAGCGAGAATTTCCGT | 118 |
|   |   | DxRRV-902 | GGTCACATCGAACAATTCTAATCTAAG | 119 |
| 10 | 174 | RRV-1001 | GGCTTTTAAAAGTTCTGTTCCGAGAG | 120 |
|   |   | RRV-1002 | GGTCACATTAAGACCGTTCCTTC | 121 |

Primers common to all four serotypes were used for RT-PCR amplification of fragments from all genes except gene 9 where primers specific to gene 9 of human rotavirus serotype G1 (HRV-D) were used. RT-PCR amplification was carried out as follows:

| RT REACTION | |
|---|---|
| RNA (RNA + water) | 10 μl |
| RNase-free water | — |
| 5× XL RT buffer | 4 μl |
| dNTP mix (2.5 mM each dNTP) | 1.6 μl |
| rTth polymerase | 2.5 μl |
| 25 mM Mn(OAc)2 | 0.88 μl |
| RT (downstream) primer (20 pmoles/μl) | 1 μl |
| TOTAL: | 20 μl |

RNA (100-500 ng per reaction) was mixed with water and 5× SL RT buffer in a Gene-amp tube. The mixture was denatured at 96° C. for 4 minutes in a pre-heated thermal cycler, and then placed on ice immediately for 3 minutes to quick cool. Samples were pulse-spun in microfuge to remove any condensation on caps, and the remaining ingredients were added. A drop of mineral oil was added to each tube, and samples were placed in pre-heated thermal cycler at 40° C. The RT thermal cycle was 40° C. for 60 minutes, followed by 45° C. for 60 minutes and then 4° C., soak. If several different fragments from the same RNA template were amplified, the entire reaction was scaled up in one tube, eliminating only the primer from the mix. One µl of the RT (+sense) primer was added to each reaction tube, and then 19 µof the scaled-up RT mix were added.

| PCR REACTION | |
|---|---|
| RNase-free water | 58.8 µl |
| 5× XL Chelating Buffer | 16 µl |
| 25 mM Mg(OAc2) | 3.2 µl |
| PCR (upstream) primer (20 pmoles/µl) | 1.5 µl |
| RT (downstream) primer (20 pmoles/µl) | 0.5 µl |
| TOTAL | 80 µl. |

The reagents were mixed for each sample; 80 µl PCR mix were added to the 20 µl RT reaction under the oil, and mixed by pipetting up and down several times. The samples were placed in pre-heated thermal cycler (hot-start) at 94° C. and cycled as follows: 94° C. denaturation for 3 minutes, followed by 40 cycles of denaturation at 94° C. for 1 minute, primer annealing at 40° C. for 30 seconds, and extension at 70° C. for two minutes. A final extension step was run at 70° C. for 10 minutes, followed by a soak cycle at 4° C.

Ten µl of reaction were run on 1% agarose gel. Products were purified using Promega's Wizard PCR preps DNA purification system (Madison Wis.) either directly or using gel purification from low-melting agarose.

Cloning of RT-PCR Products

The RT-PCR products from genes 3, 4, 5, 9 and 10 of MWVS-1, 2, 3 and 4 were cloned into the appropriate restriction endonuclease sites of either pGEM-3Zf(+)™, pGEM-5Zf(+)™, or pGEM T-Easy™ (T/A cloning) plasmid vectors using standard cloning methods.

Screening for Positive Clones

Approximately 40-100 colonies from each plasmid construct were screened for the presence of cloned RRV sequences by PCR using primers specific to the SP6 and T7 promoter sequences (SP6:5'TATTTAGGTGACAC-TATAG3') (SEQ ID NO.:122) (T7:5'TAATACGACTCAC-TATAGGG3') (SEQ ID NO.:123) flanking the cloning sites of each vector as follows: a single colony was transferred to 10 µl of water in a 0.5 ml Gene-Amps® tube using a sterile inoculating needle, and overlaid with a drop of mineral oil. The tubes were placed in a pre-heated thermal cycler at 96° C. for 10 minutes to lyse bacterial cells, and cooled to 4° C. for 3-4 minutes. Then, 40 µl PCR mix was added to each tube underneath the oil and pipetted several times to mix the sample.

PCR Mix (50 Reactions):

| | |
|---|---|
| 10× PCR buffer with $MgCl_2$ (Perkin-Elmer) | 200 µl |
| dNTP mix (2.5 mM each dNTP) (Perkin-Elmer) | 250 µl |
| SP6 promoter primer (20 pmole/µl) | 50 µl |
| T7 promoter primer (20 pmole/µl) | 50 µl |
| Nuclease-free water | 1438 µl |
| Taq DNA polymerase (Perkin-Elmer) 5 U/µl | 12 µl |
| TOTAL | 2000 µl |

The mixture was placed in a pre-heated thermal cycler (hot-start) at 94° C. and cycled as follows: initial 94° C. denaturation for 3 minutes, followed by 40 cycles of denaturation at 94° C. for 1 minute, primer annealing at 42° C. for 1 minute, and extension at 72° C. for 2 minutes, terminating with a soak file at 4° C. Each PCR product (10 µl) was run on a 1% agarose gel to confirm the presence of an insert of the appropriate size.

Sequence Determination of Positive Clones

PCR products from 25-30 positive clones were directly purified from the PCR reaction using the PCR Preps Kit (Promega) and eluted in 25 µl nuclease-free water. Three µl of the purified product were then sequenced using Taq Cycle Sequencing terminator mix, FS (ABI) and primers specific for the SP6 and 17 promoters which flank the MCS of each plasmid vector.

Sequence Confirmation of Clinical Virus Isolates

RNA was extracted from 400 µL of each clinical virus isolate as previously described. For each virus, a fragment containing the nucleotide position(s) of interest was amplified from 200-600 ng of RNA using the GeneAmp XL RNA PCR Kit (Perkin-Elmer) and primer pairs shown in Table 6. Consensus sequence of the resulting RT/PCR product, including the nucleotide of interest, was determined using Taq cycle sequencing and the ABI 377 DNA sequencer with primers denoted in Table 6.

TABLE 6

Primers Used for RT/PCR Amplification and Sequence Confirmation of Clinical Virus Isolates

| Gene # | Clone # (Sero-type) | NT # | Primer Pairs For RT/PCR and Sequencing | | | |
|---|---|---|---|---|---|---|
| 3 | 3 (G2) | 283 | 301A→GGCTATAAAGCAGTACGAGTAGTGTG | SID | 313→CGTGCTATCGGTAAAGAAGTAGT | SID |
| | 4 (G2) | 2288 | 307→GCTGATATAGAAGGTGGAAAG | 124 | 302A→GGTCACATCATGACTAGTGTG | 125 |
| | 5 (G3) | 1306 | 305→GACTGCTATGGATTTAGAGC | 126 | 311→GATAATGCGTATAATGCCAC | 127 |
| | 6 (G3) | 169 | 301A→GGCTATTAAAGCAGTACGAGTAGTGTG | 128 | 314→CTCAACAGCTGCAATTCCTG | 129 |
| | 9 (G2) | 2388 | 307→GCTGATATAGAAGGTGGAAAG | 130 | 302A→GGTCACATCATGACTAGTGTG | 131 |

TABLE 6-continued Primers Used for RT/PCR Amplification and Sequence Confirmation of Clinical Virus Isolates

| Gene # | Clone # (Sero-type) | NT # | Primer Pairs For RT/PCR and Sequencing | | | |
|---|---|---|---|---|---|---|
| | 21 (G3) | 2388 | 307→GCTGATATAGAAGGTGGAAAG | 132 | 302A→GGTCACATCATGACTAGTGTG | 133 |
| | 25 (G3) | 308 | 301A→GGCTATTAAAGCAGTACGAGTAGTGTG | 134 | 313→CGTGCTATCGGTAAAGAAGTAGT | 135 |
| | 29 (G1) | 874 | 304→GTCTCAGTTCGACAATGGAC | 136 | 312→GAATATGGAGTGTCAAGTGGGTC | 137 |
| | 38 (G4) | 448 | 301A→GGCTATTAAAGCAGTACGAGTAGTGTG | 138 | 313→CGTGCTATCGGTAAAGAAGTAGT | 139 |
| 4 | 1 (G1) | 1953 | 406→GAGCACCATAGATGCAGCT | 140 | 408→GAGTCAGTTACTAGATCTGC | 141 |
| | 6 (G3) | 1608 | 405→CAGTAATGACTGGCGGAGCAGT | 142 | 409→CTGACAGATGAAGAAACATC | 143 |
| | 11 (G3) | 417 | 401→GGCTATAAAATGGCTTCGCTC | 144 | 412→GTCACAAAATGCTGTCATG | 145 |
| | 12 (G3) | 1481 | 405→CAGTAATGACTGGCGGAGCAGT | 146 | 409→CTGACAGATGAAGAAACATC | 147 |
| | 16 (G1) | 1953 | 406→GAGCACCATAGATGCAGCT | 148 | 408→GAGTCAGTTACTAGATCTGC | 149 |
| | 19 (G2) | 1674 | 405→CAGTAATGACTGGCGGAGCAGT | 150 | 409→CTGACAGATGAAGAAACATC | 151 |
| | 20 (G3) | 1674 | 405→CAGTAATGACTGGCGGAGCAGT | 152 | 402→GGTCACATCCTCTGGAAATTGC | 153 |
| 5 | 6 (G3) | 75 | 501A→GGCTTTTTTTTGAAATGTCTTGTGTTAGC | 154 | 509→GTCTATATGGCAAATCTATGC | 155 |
| | 20 (G3) | 75 | 501A→GGCTTTTTTTTGAAATGTCTTGTGTTAGC | 156 | 509→GTCTATATGGCAAATCTATGC | 157 |
| | 3 (G2) | 1204 | 504→CTCAAACTGATTTACATCATG | 158 | 507→GTGCATAACGGCAAGTGATC | 159 |
| | 4 (G2) | 1204 | 504→CTCAAACTGATTTACATCATG | 160 | 507→GTGCATAACGGCAAGTGATC | 161 |
| | 5 (G3) | 394 | 501A→GGCTTTTTTTTGAAATGTCTTGTGTTAGC | 162 | 509→GTCTATATGGCAAATCTATGC | 163 |
| | 8 (G2) | 667 | 503→CAGAGGAAATGTAGAAATGAG | 164 | 508→CAATCCATGTCTCTGAATGC | 165 |
| | 9 (G2) | 667 | 503→CAGAGGAAATGTAGAAATGAG | 166 | 508→CAATCCATGTCTCTGAATGC | 167 |
| | 10 (G3) | 1186 | 504→CTCAAACTGATTTACATCATG | 168 | 507→GTGCATAACGGCAAGTGATC | 169 |
| | 29 (G1) | 1219 | 504→CTCAAACTGATTTACATCATG | 170 | 507→GTGCATAACGGCAAGTGATC | 171 |
| 9 | 22 (G1) | 556 | 901→GGCTTTAAAAGCGAGAATTTCCGT | 172 | D-902→GGTCACATCGAACAATTCTAATCTAAG | 173 |
| | 29 (G1) | 556 | 901→GGCTTTAAAAGCGAGAATTTCCGT | 174 | D-902→GGTCACATCGAACAATTCTAATCTAAG | 175 |
| | 37 (G4) | 263 | 901→GGCTTTAAAAGCGAGAATTTCCGT | 176 | ST3-905→GTACATGATGATCCCATTGA | 177 |
| 10 | 22 (G1) | 92 | 1001→GGCTTTTTAAAAGTTCTGTTCCGAGAG | 178 | 1002→GGTCACATTAAGACCGTTCCTTC | 179 |
| | 22 (G1) | 174 | 1001→GGCTTTTTAAAAGTTCTGTTCCGAGAG | 180 | 1002→GGTCACATTAAGACCGTTCCTTC | 181 |
| | 22 (G1) | 218 | 1001→GGCTTTTTAAAAGTTCTGTTCCGAGAG | 182 | 1002→GGTCACATTAAGACCGTTCCTTC | 183 |

Results

Analysis of Micro-Heterogeneity in Clinical Virus Seeds (MWVS-1, 2, 3 and 4)

Sequence analysis of genes 3, 4, 5, 9 and 10 of the 19 clinical viral isolates obtained from the stools of ROTA-MUNE™ recipients had heterogeneity at 24 nucleotide positions when compared to consensus sequence of the clinical seeds (MWVS-1, 2, 3 and 4). One of these sites, nucleotide position 174 of gene 10, contains a base mixture in the serotype G1 and G4 viruses. In addition, 7 of the 24 nucleotide base substitutions identified in the clinical virus isolates (i.e., position 2388 in gene 3; positions 1674 and 1953 in gene 4; positions 75, 667 and 1204 in gene 5; and position 556 in gene 9) were observed in more than one virus sample. To establish the precise level of microheterogeneity present at nucleotide position 174 of gene 10, as well as to determine whether the seven nucleotide base substitutions found in more than one clinical virus isolate were the result of sequence micro-heterogeneity in the clinical virus seeds, clonal analysis was carried out on each of the four seeds at these eight nucleotide positions.

The clonal analysis revealed micro-heterogeneity at position 2388 in gene 3 of the G2 clinical seed (MWVS-2), and at position 174 in gene 10 of the G1, G21 and G4 virus seeds (MWVS-3, 2 and 4, respectively). Twenty-six percent of the viral genomes in the G2 clinical seed were found to contain minor species C at position 2388 of gene 3, while the remaining 74% of the genomes contained T at this position. As predicted by consensus sequence, heterogeneity (i.e., G>A) was observed for position 174 of gene 10 in the G1 (MVS-3) and G4 (MWVS-4) clinical seeds, where the minor species A was found in 12% and 7% of the genomes, respectively. In contrast, the genomes of the RRV parental strain contained solely A at this position. The analysis also revealed a minor population of 5% G at the same position in the G2 virus seed (MWVS-2) which was not detected by consensus sequencing.

The remainder of the nucleotide substitutions which occur in more than one of the clinical isolates (i.e., positions 1674 and 1953 of gene 4; positions 75, 667 and 1204 of gene 5; and position 556 of gene 9) apparently do not result from measurable sequence micro-heterogeneity within the virus seeds, since mixtures of bases were not found at these positions by clinical (MWVS-1, 2, 3 and 4) vaccine seeds at positions 2388 and 174 in genes 3 and 10, respectively. By clonal analysis, 15% of the minor species (C) was observed at nucleotide position 2388 in the G2 commercial virus seed (MWVS-2), compared to 26% C in the G2 clinical virus seed (MWVS-2), as Serotype 1=MWVS-3=DxRRV; Serotype 2=MWVS-2=DS1xRRV;

Serotype 3=MWVS-1=RRV; Serotype 4=MWVS4=ST3xRRV

TABLE 7

Micro-Heterogeneity within clinical virus seeds (MWVS 1, 2, 3 and 4)

| Gene | Serotype (Virus Seed) | Genomic Nucleotide Position | Nucleotide Representing Consensus (% population) | Nucleotide Representing Minor Variant (% population) | Number of Clones Sequenced |
|---|---|---|---|---|---|
| 3 | 1 (MWVS-3) | 2388 | T (100%) | C (0%) | 28 |
|   | 2 (MWVS-2) |  | T (74%) | C (26%) | 27 |
|   | 3 (MWVS-1) |  | T (100%) | C (0%) | 60 |
|   | 4 (MWVS-4) |  | T (100%) | C (0%) | 26 |
| 4 | 1 (MWVS-3) | 1674 | A (100%) | G (0%) | 26 |
|   | 2 (MWVS-2) |  | A (100%) | G (0%) | 24 |
|   | 3 (MWVS-1) |  | A (100%) | G (0%) | 33 |
|   | 4 (MWVS-4) |  | A (100%) | G (0%) | 31 |
|   | 1 (MWVS-3) | 1953 | C (100%) | A (0%) | 28 |
| 5 | 1 (MWVS-3) | 75 | C (100%) | A (0%) | 25 |
|   | 2 (MWVS-2) |  | C (100%) | A (0%) | 20 |
|   | 3 (MWVS-1) |  | C (100%) | A (0%) | 20 |
|   | 4 (MWVS-4) |  | C (100%) | A (0%) | 20 |
|   | 1 (MWVS-3) | 667 | C (100%) | T (0%) | 26 |
|   | 2 (MWVS-2) |  | C (100%) | T (0%) | 19 |
|   | 3 (MWVS-1) |  | C (100%) | T (0%) | 20 |
|   | 4 (MWVS-4) |  | C (100%) | T (0%) | 20 |
|   | 1 (MWVS-3) | 1204 | G (100%) | A (0%) | 26 |
|   | 2 (MWVS-2) |  | G (100%) | A (0%) | 20 |
|   | 3 (MWVS-1) |  | G (100%) | A (0%) | 20 |
|   | 4 (MWVS-4) |  | G (100%) | A (0%) | 21 |
| 9 | 1 (MWVS-3) | 556 | G (100%) | A (0%) | 41 |
| 10 | 1 (MWVS-3) | 174 | *G (88%) | *A (12%) | 26 |
|   | 2 (MWVS-2) |  | A (95%) | G (5%) | 22 |
|   | 3 (MWVS-1) |  | A (100%) | G (0%) | 21 |
|   | 4 (MWVS-4) |  | *G (93%) | *A (7%) | 28 |

*Mixed base depicted in MWVS-3 and MWVS-4 by consensus sequencing (see Table 4).

clonal analysis. Table 7 summarizes the micro-heterogeneity found in the clinical virus seeds (MWVS-1, 2, 3 and 4) at the variable nucleotide positions. The micro-heterogeneity at these positions may exist at levels below the detection limits, or the substitutions observed in the clinical isolates may represent adaption within the human gastrointestinal tract.

Sequence Confirmation of Clinical Virus Isolates

The sequence of the clinical virus isolates at each of the 24 nucleotide positions where the sequence had been found to diverge from consensus was re-examined. Table 8 lists the 24 nucleotide positions of heterogeneity.

Analysis of the Genetic Stability of RRV at Positions 2388 and 174 in Genes 3 and 10, Respectively Consensus sequencing of the commercial seeds (MWVS-5, 6, 7 and 8) revealed heterogeneity at positions 2388 and 174 in genes 3 and 10, respectively. To compare the precise levels of micro-heterogeneity in the clinical and commercial virus seeds at these positions, as well as to analyze the genetic stability of these nucleotide positions during vaccine manufacture, clonal analysis of these positions was carried out in the commercial virus seeds and several vaccine lots generated from them.

The data showed that a similar level of micro-heterogeneity existed in the commercial MWVS-5, 6, 7 and 8) and

TABLE 8

Nucleotide Sequence Differences Between Clinical Virus Isolates and Consensus Sequence of MWVS.

| Gene # | Clone # (Serotype) | NT # | NT Change | AA # | AA Change |
|---|---|---|---|---|---|
| Gene 3 | 3 (G2) | 283 | TGC (TGT)[1] |  |  |
|  | 4 (G2) | 2288 | No change[3] | 747 |  |
|  | 5 (G3) | 1306 | AGC (AGT) |  |  |
|  | 6 (G3) | 169 | ACA (ACG) |  |  |
|  | 9 (G2) | 2388 | TCA (TTA) | 780 | Phe (Leu)[2] |
|  | 21 (G3) | 2388 | No change | 780 |  |
|  | 25 (G3) | 308 | No change | 87 |  |
|  | 29 (G1) | 874 | TTC (TTA) |  |  |
|  | 38 (G4) | 448 | GAC (GAT) |  |  |
| Gene 4 | 1 (G1) | 1953 | TCA (TCC) |  |  |
|  | 6 (G3) | 1608 | GGC (GGT) |  |  |
|  | 11 (G3) | 417 | ACG (ACA) |  |  |
|  | 12 (G3) | 1481 | ACA (AGA) | 501 | Thr (Arg) |
|  | 16 (G1) | 1953 | TCA (TCC) |  |  |
|  | 19 (G2) | 1674 | No change |  |  |
|  | 20 (G3) | 1674 | No change |  |  |
| Gene 5 | 6 (G3) | 75 | AAA (ACA) | 22 | Lys (Thr) |
|  | 20 (G3) | 75 | AAA (ACA) | 22 | ys (Thr) |

TABLE 8-continued

Nucleotide Sequence Differences Between Clinical
Virus Isolates and Consensus Sequence of MWVS.

| Gene # | Clone # (Serotype) | NT # NT Change | AA # AA Change |
|---|---|---|---|
|  | 3 (G2) | 1204 GAA (GAG) |  |
|  | 4 (G2) | 1204 GAA (GAG) |  |
|  | 5 (G3) | 394 No change |  |
|  | 8 (G2) | 667 TTT (TTC) |  |
|  | 9 (G2) | 667 TTT (TTC) |  |
|  | 10 (G3) | 1186 TAC (TAT) |  |
|  | 29 (G1) | 1219 ACG (ACA) |  |
| Gene 9 | 22 (G1) | 556 ATA (GTA) | 170 Ile (Val) |
|  | 29 (G1) | 556 ATA (GTA) | 170 Ile (Val) |
|  | 37 (G4) | 263 CGA (CAA) | 72 Arg (Gln) |
| Gene 10 | 22 (G1) | 92 ATA (ATG) | 17 Ile (Met) |
|  | 22 (G1) | 174 ACA (GCA) | 45 Thr (Ala) |
|  | 22 (G1) | 218 AAG (AAA) |  |

[1]Underlined nucleotide is different in the clinical isolate when compared to the Manufacture's Working Virus Seed (MWVS). Triplet in parentheses is the consensus sequence of MWVS.
[2]Amino acid (aa) in parentheses is present in the relevant MWVS.
[3]Initial clonal sequence analysis had indicated heterogeneity at the positions listed as "No change". Consensus sequence analysis of these isolates revealed sequence identity with the corresponding MWVS.
Boldface type indicates that the nucleotide change was identified in more than one clinical isolate.

shown in Table 9. Analysis of the micro-heterogeneity present in the commercial seeds at nucleotide position 174 in gene 10 revealed 25% and 23% of the minor species (A) in the G1 and G4 viruses, respectively, as shown in Table 10; these were similar to the levels observed in the clinical virus seed bank (12% and 7% respectively). As observed in the clinical seeds, the RRV G3 commercial seed strain (MWVS-7) contained solely A at nucleotide position 174. The G2 strain of the commercial seed bank (MWVS-6), however, did not retain the same minor population observed in the G2 clinical strain (5% G), but instead, resembled the G3 RRV strain at this position, harboring 100% A at this site by clonal analysis.

Determination of the heterogeneity at nucleotides 2388 and 174 of genes 3 and 10, respectively, in several vaccine lots produced from the commercial manufacturer's working virus seed allowed the monitoring of the genetic stability of these positions after passage in vitro. Four vaccine lots of each serotype, generated from the commercial virus seeds (MWVS-5, 6, 7 and 8) were analyzed by clonal analysis. Four G2 vaccine lots (I973029, I983008, I983037 and I973030) were analyzed for heterogeneity at nucleotide position 2388 in gene 3, and in each case, the level of the minor variant (4%, 8%, 8% and 16% C) was found to be similar to the 15% observed in the G2 commercial seed (MWVS-6) (Table 9). For nucleotide 174 in gene 10, each of the four G1 and G4 vaccine lots contained the minor species (A) at a level similar to that seen in its corresponding commercial seed. The four G1 vaccine lots (I973020, I973017, I983026 and I983003) contained 22%, 6%, 33% and 4% A, respectively, at nucleotide position 174 compared to the 25% A observed in the G1 commercial (MWVS-5) seed. Likewise, the G4 vaccine lots (I973034, I973004, I973030 and I983030) retained 9%, 14%, 19% and 23% A, respectively, at this position, similar to the 23% A found in the G4 (MWVS-8) seed (Table 10). These data indicate that conditions used in the vaccine manufacturing process preserve the identity of the four RRV vaccine strains as reflected in their genomic nucleotide sequence.

TABLE 9

Base Composition at Nucleotide 2388 in Gene 3 for Serotype 2 Manufacturer's Working Virus Seed and Vaccine Concentrates

| | Nucleotide representing consensus/variant (% population) | | | | |
|---|---|---|---|---|---|
| Serotype | Manufacturer's Working Virus Seed- Commercial (MWVS-6) | RRV Commercial Vaccine Concentrates and Harvests | | | |
| | | Lot #I973030 | Lot #I973029 | Lot #I983008 | Lot #I983037 |
| 2 | T/C (85/15) | T/C (84/16) | T/C (96/4) | T/C (92/8) | T/C (92/8) |

TABLE 10

Base Composition at Nucleotide 174 in Gene 10 for Manufacturer's Working Virus Seeds and Vaccine Concentrates

| | Nucleotide Representing Consensus/Variant (% Population) | | | | |
|---|---|---|---|---|---|
| Serotype | Manufacturer's Working Virus Seeds | RRV Commercial Vaccine Concentrates and Harvests* | | | |
| 1 | G/A (75/25) [24] | G/A (78/22) [23] | G/A (94/6) [32] | G/A (67/33) [24] | G/A (96/4) [24] |
| 2 | A/G (100/0) [29] | A/G (100/0) [26] | A/G (100/0) [21] | A/G (100/0) [21] | A/G (100/0) [24] |
| 3 | A/G (100/0) [30] | A/G (100/0) [43] | A/G (100/0) [23] | A/G (100/0) [37] | Not Determined |
| 4 | G/A (77/23) [30] | G/A (91/9) [23] | G/A (86/14) [28] | G/A (81/19) [21] | G/A (77/23) [71] |

Manufacturer's Working Virus Seeds = MWVS-5, 6, 7 and 8 for Serotypes 1, 2, 3 and 4, respectively.
*Vaccine Concentrates and Harvests:
Serotype 1 - Lot # I973020, I973017, I983026 and I983003, respectively.
Serotype 2 - Lot # I973030, I973029, I983008 and I983037, respectively.
Serotype 3 - Lot # I973026, I983021 and I983032, respectively.
Serotype 4 - Lot # I973034, I973004, I973040 and I983030, respectively.

Superscripts denote the number of clones sequenced for each virus lot.

Example 3

Mutant Analysis by PCR and Restriction Enzyme Cleavage (MAPREC)

A sensitive and direct method to monitor the levels of micro-heterogeneity at nucleotide 2388 of gene 3, Mutant Analysis by PCR and Restriction Enzyme Cleavage (MAPREC), was developed.

Materials

The following materials were used: Life Technologies (Gibco-BRL) SuperScript™ Preamplification for First Strand cDNA Synthesis kit; RNase-free water; RRV Serotype 2 total RNA; Gene 3 nucleotide 2388 100% T DNA control template (1/30 dilution of stock); Gene 3 nucleotide 2388 100% C DNA control template (1/30 dilution of stock); Perkin Elmer Thermal Cycler PE 480; primer RRV-G3-EcoRI (20 pmole/µl); primer RRV-302A-flourescein (20 pmole/µl); Perkin-Elmer Taq DNA polymerase; mineral oil (Sigma), molecular biology grade 5; Perkin-Elmer 0.5 ml Gene-Amp reaction tubes; Pharmacia G40 AutoSeq spin columns; restriction endonuclease Eco RI (10 U/µl) (Roche Molecular Biochemicals); glycerol; bromophenyl blue; xylene cyanol; Bio-Rad 40% acrylamide:bis-acrylamide (38:2) liquid; distilled water; 10× TBE (Gibco-BRL); TEMED; ammonium persulfate; two 20×20 cm vertical polyacrylamide gel electrophoresis apparatus with 0.75 mm, 20-well combs and 0.75 mm spacers; flat head gel loading pipet tips; Molecular Dynamics Flourimager 595.

Reverse Transcription

For each sample, 500-1000 ng RNA and water were added to a 0.5 ml microfuge tube for a final volume of 11 µl. It was preferable to use 1000 ng RNA per reaction if the RNA is concentrated enough; however, 500 ng per reaction was usually sufficient to generate product. The RNA and water mixture was heated in a pre-heated thermal cycler at 96° C. for 4 minutes, and then immediately placed on ice for 2-3 minutes. During that time, the RT mix was made as follows:

| | |
|---|---|
| 10× PCR Buffer (Superscript II kit) | 2 µl |
| 25 mM Magnesium chloride (Superscript II kit) | 2 µl |
| 10 mM dNTP mix (Superscript II kit) | 1 µl |
| 0.1 M DTT (Superscript II kit) | 2 µl |
| RV-302A-Flourescein primer (20 pmole/µl) | 1 µl |
| TOTAL: | 8 µl. |

After cooling, the chilled RNA and water mixture was briefly centrifuged to spin down any condensation on the tube cap. Then 8 µl RT mix (above) was added to each tube of RNA and water mixture, and mixed by pipeting up and down several times. A drop of mineral oil was overlaid in the reaction tube, and the tube was then incubated in a pre-heated thermal cycler at 50° C. for 5 minutes. Subsequently, 1 µl Superscript II Reverse Transcriptase 200 U/µl (kit) was added to each reaction tube underneath the oil layer. The reverse transcription process was allowed to proceed at 50° C., for 60 minutes, followed by 70° C. for 15 minutes to inactivate the RT; the mixture was then soaked at 4° C. One µl RNase H (Superscript II kit) was added to each reaction underneath the oil, and the reaction was incubated in a thermal cycler at 37° C. for 20 minutes. The first-strand cDNA resulting from this procedure could either be transferred to 4° C. and used directly in the PCR reaction, or stored at −20° C.

PCR Step

It should be noted that in addition to the vaccine samples, each assay must be accompanied by two DNA control reactions containing either 100% T or 100% C DNA templates, to validate each assay.

PCR mix was prepared as follows:

| | |
|---|---|
| 10× PCR Buffer (Superscript II kit) | 5 µl |
| 25 mM magnesium chloride (Superscript II kit) | 3 µl |
| 10 mM dNTP mix (Superscript II kit) | 1 µl |
| RRV-302A-Flouroscein primer (20 pmole/µl) | 1.5 µl |
| RRV-G3-EcoRI primer (20 pmole/µl) | 1.5 µl |
| Taq DNA polymerase (Perkin-Elmer) | 0.5 µl |
| Nuclease-free water | 35 µl |
| TOTAL: | 47.5 µl. |

The PCR mix was aliquoted to a fresh 0.5 ml tube for each sample. Three µl of the first strand cDNA (from the RT reaction), 3 µl of 1/30 dilution of 100% T DNA, or 3 µl of 1/40 dilution of 100% C DNA were added to each PCR reaction as a template, and the reaction was then overlaid with a drop of mineral oil. The reaction was placed in a pre-heated thermal cycler, and cycled for 94° C. for 1 minutes (1 cycle), followed by 94° C. for 30 seconds and 60° C. for 3 minutes (40 cycles), and then a 4° C. soak.

Since the PCR products being generated are fluorescent, their exposure to light should be minimized by placing a piece of aluminum foil over the thermal cycler cover during cycling. Storage of the PCR products should always be in light tight containers.

Purification and Digestion of PCR Products

A Pharmacia G40 spin column was prepared for use in the purification of each PCR product. Each column was vortexed for 2-3 seconds to thoroughly resuspend the Sephadex beads; the screw cap was loosened one-half turn; the bottom of the column was snapped off and discarded, and then the screw cap was removed and discarded as well. Each column was placed in an empty 1.5 ml Eppendorf tube and spun in an Eppendorf microfuge at 3200 rpm (approximately 200×g) for 1 minute. Columns were then used immediately to avoid drying of the resin. The PCR reaction described above was removed from each tube, being careful to transfer as little oil as possible. The G-50 spin column was removed from its tube, and the entire 50 µl PCR reaction was slowly loaded onto the center of the angled resin in the column. The loaded column was then placed into a fresh, labeled 1.5 ml Eppendorf microfuge tube. The tubes were spun at 3200 rpm for 1 minute to collect the effluent containing the purified PCR product, and column was discarded. This purification step allows subsequent digestion of the PCR product with EcoRI to take place in a proper restriction enzyme buffer, as digestion with EcoRI in other buffers results in non-specific digestion of PCR products. Eight µL of each purified PCR reaction was removed to a new 0.5 ml Gene-amp tube, and 1 µl of Restriction Buffer H (Roche Mol. Biochemicals) provided with the EcoRI enzyme was added. One µl of EcoRI restriction enzyme (10 U/µl) was added to each sample and pipetted up and down several times to thoroughly mix reaction contents. The reaction tubes were then placed in a thermal cycler at 37° C. for 3-4 hours. The reactions were spun down by pulsing in microfuge to spin down any condensation on the tube cap, and 2 µl of 6× loading dye (40% glycerol, 0.05% Bromophenyl Blue, 0.05% Xylene Cyanol) were added to each digested sample, and then the samples were stored at 4° C. in light tight containers until loaded onto the gel.

Polyacrylamide Gel Electrophoresis of Digested PCR Products

During the final hour of the digestion step (above), polyacrylamide gels were prepared for analyses of the digested PCR products. Gel plates were washed with Alconox detergent, followed by a final rinse with ethanol, and allowed to air dry. The plates were assembled, and a 6% non-denaturing polyacrylamide gel mixture was prepared as follows:

| Distilled water | 45 ml |
|---|---|
| 10× TBE | 6 ml |
| 40% acrylamide:bis (38:2) | 9 ml |
| TOTAL: | 60 ml |

(This gel recipe was sufficient to pour two 20×20 cm gels; each gel accommodated nine samples.)

For polymerization, 50 µl TEMED and 500 µl freshly prepared 10% ammonium persulfate were added to the gel mixture, swirling gently to mix reagents. The gel was immediately poured, the comb inserted, and clamps placed on the wells. Polymerization was allowed to occur for approximately one hour, after which the comb was removed and the wells rinsed with 1× TBE. The bottom buffer chamber was filled with 1× TBE. An entire 12 µl of each sample was loaded onto the gel, and the gel was run at 200-220 volts until the xylene cyanol was approximately 2 cm from the bottom of the gel (approximately 3 hours).

Quantitation of Undigested and Digested Band Density by Flourimaging

The gels were transferred to an overhead transparency, and then to a glass sample plate on the Flourimager. The gel was scanned on the Flourimager with the following settings: voltage (PMI)=600; filter 1=530 dF30 agarose; wavelength=488 nm. Once the gel was scanned, the image could be modified and quantitated using ImageQuant2 software. The percent C at nucleotide 2388 was then calculated:

a) Corrected volume of undigested product (CU)=undigested band volume−background volume.
b) Corrected volume of digested product (CD)=digested band volume−background volume.
c) Percent 2388 "C" =[CD/(CD+CU)]×100.

To ensure validity of each individual determination, all of the following conditions were met: 1) the value of % 2388 C in the 100% C DNA control sample must have been≧905; 2) the value of % 2388 C in the 100% T DNA control sample must have been less than 1.5%; and 3) the total bands of fluorescence (indicated by the volume) present in the undigested and digested bands must have been≧500,000.

Results

RNA was extracted as described above from each of 15 serotype G2 commercial vaccine lots, and for each vaccine lot, 5 individual determinations of the level of variant "C" at nucleotide position 2388 were carried out. The RNA from each virus sample was used to synthesize first strand cDNA (reverse transcription) in two independent experiments carried out on separate days. Three independent determinations of % C at nucleotide position 2388 were made using cDNA derived from the first reverse transcription reaction as PCR template, while the remaining two independent determinations were carried out using cDNA derived from the second reverse transcription reaction. For each sample, the Mean and Standard Deviation of the five determinations was calculated.

Following the protocols described above, a short region of gene 3 of RRV serotype G2 virus, encompassing nucleotide position 2388, was amplified by RT/PCR using the Superscript Pre-amplification System for First Strand cDNA synthesis (Life Technologies, Rockville, Md.). One of the primers used for amplification was homologous to the sequence immediately upstream of nucleotide 2388 and was designed to create an Eco RI restriction enzyme site if a cytosine residue was present at position 2388 (RRV-G3-EcoRI primer, GTTAGTGGAGTTCTAGCGACATATTT-TAAAATGTAGAAT (SEQ ID NO: 186), corresponding to plus sense nucleotides 2347-2386). The second primer (RRV-302A-5'Flourescein, GGTCACATCATGACTAGTGTG (SEQ ID NO: 187), corresponding to negative sense nucleotides 2571-2591) was labeled with Flourescein (at the 5' end), enabling the resulting PCR product to be visualized and quantitated using polyacrylamide gel electrophoresis and flourimaging techniques.

Following amplification, the PCR product was purified and digested. PCR products derived from genomes containing cytidine (C) at nucleotide position 2388 were digested, resulting in 34 and 207 bp digested fragments; of these two fragments, only the 207 bp fragment retains the flourescein tag and was detected by PAGE). Those genomes containing thymidine (T) at nucleotide position 2388 did not generate an EcoRI site, and thus yielded a 244 bp uncleaved product. The products were separated on a 6% polyacrylamide gel, and the relative densities of bands representing the undigested and digested products were quantitated using the Flourimager 595 (Molecular Dynamics), and a measurement of background fluorescence was taken. The percentage of viral genomes in the sample containing "C" at nucleotide 2388 was then calculated.

Base mixtures at nucleotide position 2388 in gene 3 and nucleotide position 174 in gene 10 were consistently detected in vaccine virus at the master working virus seed (MWVS) and vaccine monopool bulk concentrate stages. Thus, measurement of the inherent heterogeneity at these positions in the vaccine virus lots can be used as the foundation for a product consistency assay. The MAPREC analysis was used to determine the base composition at nucleotide 2388. The low level of variation observed in the fifteen G2 commercial vaccine lots at this nucleotide position demonstrates, not only the stability of the subpopulation containing C at nucleotide, but also the consistency of the vaccine manufacturing process. The average percentage of C at nucleotide position 2388 ranged from 2/75% to 6.68%, resulting in a variation of no more than 3.92% when any of the fifteen vaccine lots were compared (Table 11). The first three MAPREC determinations, revealed slightly higher levels of the minor species (C) compared to the remaining twelve G2 vaccine lots. However, three additional determinations carried out from a new RT reaction yielded levels of C consistent with those observed in the other twelve lots. Reanalyzing the data to exclude the first three MAPREC determinations, the range of variation observed for the fifteen vaccine lots was significantly reduced (i.e., a low of 2.76% and a high of 4.90%, equivalent to a variation of just 2.14%). In each case, excluding the three aberrant determinations, the standard deviation observed across five MAPREC determinations of the percentage C at nucleotide position 2388 of gene 3 in the commercial vaccine lots fell well below 1%, with over 50% of the samples resulting in standard deviations less than 0.5%. Taking into account that the variation observed was nearly 4 times greater by clonal analyses

TABLE 11

MAPREC Analysis of % C at Nucleotide Position 2388 in RRV Gene 3

| Sample Name | Trial#1 | Trial#2 | Trial#3 | Trial#4 | ^Trial#5 | *Trial#5B | ^Trial#6 | Average | Standard Duration |
|---|---|---|---|---|---|---|---|---|---|
| 100% T-DNA Control | 1.13 | 1.04 | 0.85 | 0.47 | 0.86 | | | 0.87 | 0.25 |
| 100% C-DNA Control | 92.24 | 93.38 | 93.85 | 93.94 | 93.33 | | | 93.35 | 0.68 |
| Serotype 2-I97328 | 3.60 | 4.16 | 3.56 | 4.88 | 4.20 | 3.12 | 3.11 | 3.80 | 0.64 |
| Serotype 2-I973029 | 3.38 | 3.08 | 4.16 | 5.20 | 4.97 | 3.39 | 3.17 | 3.91 | 0.88 |
| Serotype 2-I973030 | 4.06 | 3.11 | 4.72 | 3.38 | 4.62 | 4.04 | 3.38 | 3.90 | 0.63 |
| Serotype 2-I973032 | 4.16 | 4.60 | 3.82 | 3.32 | 3.23 | 2.58 | 3.76 | 3.64 | 0.66 |
| Serotype 2-I983005 | 7.69 | 5.38 | 12.31 | 4.97 | 5.41 | | 4.34 | 6.68 | 2.98 |
| Serotype 2-I983006 | 6.67 | 4.33 | 9.00 | 4.12 | 5.25 | | 5.11 | 5.75 | 1.83 |
| Serotype 2-I983007 | 6.68 | 5.20 | 6.11 | 4.14 | 4.04 | | 4.31 | 5.08 | 1.11 |
| Serotype 2-I983008 | 2.97 | 3.97 | 3.46 | 2.79 | 2.85 | | 3.65 | 3.28 | 0.48 |
| Serotype 2-I983009 | 3.76 | 3.72 | 3.63 | 3.06 | 3.46 | | 3.60 | 3.54 | 0.26 |
| Serotype 2-I983011 | 3.65 | 4.36 | 3.83 | 4.01 | 4.13 | | 3.81 | 3.97 | 0.26 |
| Serotype 2-I983012 | 3.14 | 3.52 | 3.30 | 2.82 | 2.95 | | 2.76 | 3.08 | 0.29 |
| Serotype 2-I983013 | 3.32 | 3.99 | 3.55 | 3.48 | 2.55 | | 3.72 | 3.44 | 0.49 |
| Serotype 2-I983037 | 3.36 | 3.35 | 3.82 | | 3.83 | | 3.97 | 3.67 | 0.29 |
| Serotype 2-I983038 | 4.16 | 4.67 | 4.76 | | 4.05 | | 4.56 | 4.44 | 0.32 |
| Serotype 2-I983039 | 4.88 | 3.75 | 3.84 | | 3.38 | | 4.49 | 4.07 | 0.61 |

*A second digestion sample taken from the PCR rxn generated in trial 5. (A digestion duplicate)
^Trials 5 and 6 were PCR rxns. seeded from the same RT rxn. and carried out on the same day.

than was found using MAPREC (8% vs 2.14%, respectively), the levels of the minor species (C) in the G2 vaccine pools as measured by either method are comparable (average of 4% for MAPREC vs 8% for clonal analysis). These data indicate that MAPREC analyses of base composition at nucleotide 2388 in gene 3 of RRV were both accurate and reproducible.

While this invention has been particularly shown and described with reference to preferred embodiments thereof, it will be understood by those skilled in the art that various changes in form and details may be made therein without departing from the spirit and scope of the invention as defined by the appended claims.

What is claimed is:

1. An isolated nucleic acid molecule having the sequence of SEQ ID NO:3.

2. An isolated nucleic acid molecule having the sequence of SEQ ID NO:3 with a C replacing a T at nucleotide 2388.

3. A vector comprising an isolated nucleic acid of claim 1 or claim 2.

4. A recombinant host cell comprising a vector of claim 3.

5. A method for producing a polypeptide encoded by an isolated nucleic acid molecule, comprising culturing the recombinant hose cell of claim 4 under conditions suitable for expression of said nucleic acid molecule.

6. A method for determining the stability of a manufactured reassortant rotavirus composition, comprising the determination of the micro-heterogeneity at nucleotide position 2388 of gene 3 encoding the polypeptide having the sequence of SEQ ID NO: 17 of the rotavirus in a plurality of lots of the manufactured ressortant rotavirus composition, wherein the level of C at nucleotide position 2388 of gene 3 found in the plurality of lots is consistent, thereby indicating that the manufactured ressortant rotavirus composition is stable.

7. The method according to claim 6, wherein micro-heterogeneity is determined by clonal analysis or PCR.

8. The method according to claim 7, wherein determining the level of micro-heterogeneity at nucleotide 2388 of gene 3 by PCR, comprises:

a) isolating the RNA from a sample of the reassortant rotavirus culture;

b) producing a first-strand cDNA by reverse transcription with a primer sequence from upstream of nucleotide 2388;

c) amplifying the first-strand cDNA by PCR with a primer sequence from upstream of nucleotide 2388 and a primer sequence from downstream of nucleotide 2388;

d) quantitating the ratio of T versus C at nucleotide position 2388.

9. The method according to claim 8, wherein the primer sequence upstream of nucleotide 2388 is SEQ ID NO: 187.

10. The method according to claim 8, wherein the primer sequence downstream of nucleotide 2388 is SEQ ID NO: 186.

11. The method according to claim 8, wherein the primers are labeled.

12. The method according to claim 11, wherein the primer label is fluorescent.

* * * * *